(12) United States Patent
Lee et al.

(10) Patent No.: US 8,017,398 B2
(45) Date of Patent: Sep. 13, 2011

(54) METHOD FOR ASSAYING PROTEIN-PROTEIN INTERACTION

(75) Inventors: Kevin J. Lee, New York, NY (US); Richard Axel, NY, NY (US); Walter Strapps, NY, NY (US); Gilad Barnea, NY, NY (US)

(73) Assignees: Life Technologies Corporation, Carlsbad, CA (US); The Trustees of Columbia University in the City of New York, New York, NY (US)

( * ) Notice: Subject to any disclaimer, the term of this patent is extended or adjusted under 35 U.S.C. 154(b) by 772 days.

(21) Appl. No.: 11/346,759

(22) Filed: Feb. 2, 2006

(65) Prior Publication Data

US 2006/0147975 A1 Jul. 6, 2006

Related U.S. Application Data

(62) Division of application No. 10/888,313, filed on Jul. 9, 2004, now Pat. No. 7,049,076.

(60) Provisional application No. 60/566,113, filed on Apr. 27, 2004, provisional application No. 60/511,918, filed on Oct. 15, 2003, provisional application No. 60/485,968, filed on Jul. 9, 2003.

(51) Int. Cl.
  C12N 15/09 (2006.01)
  C12N 15/00 (2006.01)
  C12N 1/21 (2006.01)
  C12N 15/85 (2006.01)

(52) U.S. Cl. .................... 435/455; 435/252.3; 435/325; 435/69.7

(58) Field of Classification Search .................. None
See application file for complete search history.

(56) References Cited

U.S. PATENT DOCUMENTS

| | | | |
|---|---|---|---|
| 4,468,390 A | 8/1984 | Kitano | |
| 5,168,062 A | 12/1992 | Stinski | |
| 5,283,173 A | 2/1994 | Fields et al. | |
| 5,284,746 A | 2/1994 | Sledziewski et al. | |
| 5,385,839 A | 1/1995 | Stinski | |
| 5,439,924 A | 8/1995 | Miller | |
| 5,464,758 A | 11/1995 | Gossen et al. | |
| 5,468,614 A | 11/1995 | Fields et al. | |
| 5,491,084 A | 2/1996 | Chalfie et al. | |
| 5,667,973 A | 9/1997 | Fields et al. | |
| 5,773,422 A | 6/1998 | Komer | |
| 5,814,618 A | 9/1998 | Builard et al. | |
| 5,874,103 A | 2/1999 | Moore et al. | |
| 5,891,646 A | 4/1999 | Barak et al. | |
| 6,110,693 A | 8/2000 | Barak et al. | |
| 6,117,639 A * | 9/2000 | Germann et al. | 435/6 |
| 6,165,987 A | 12/2000 | Harvey | |
| 6,333,167 B1 | 12/2001 | Quinet et al. | |
| 6,455,300 B1 | 9/2002 | Htun et al. | |
| 6,482,425 B1 | 11/2002 | Huet et al. | |
| 6,528,271 B1 | 3/2003 | Bohn et al. | |
| 6,800,445 B2 | 10/2004 | Palmer et al. | |
| 6,893,827 B1 * | 5/2005 | Palmer et al. | 435/7.1 |
| 7,049,076 B2 | 5/2006 | Lee | |
| 7,192,737 B2 * | 3/2007 | Horwitz | 435/69.1 |
| 7,297,503 B2 * | 11/2007 | Loomis et al. | 435/7.2 |
| 2002/0028433 A1 | 3/2002 | Palmer et al. | |
| 2002/0106698 A1 | 8/2002 | Manfredi | |
| 2002/0106739 A1 | 8/2002 | Oakley et al. | |
| 2002/0132327 A1 | 9/2002 | Hay et al. | |
| 2003/0013137 A1 | 1/2003 | Barak et al. | |
| 2003/0049712 A1 | 3/2003 | Haugwitz | |
| 2003/0055089 A1 | 3/2003 | Sirinyan et al. | |
| 2003/0082642 A1 | 5/2003 | Htun et al. | |
| 2003/0143626 A1 | 7/2003 | Colas et al. | |
| 2003/0157553 A1 | 8/2003 | Berstein | |
| 2003/0236203 A1 | 12/2003 | Freehauf et al. | |
| 2004/0002119 A1 | 1/2004 | Iannone et al. | |
| 2004/0033564 A1 | 2/2004 | Seong et al. | |
| 2005/0084864 A1 | 4/2005 | Rossner et al. | |

FOREIGN PATENT DOCUMENTS

| | | |
|---|---|---|
| DE | 2221621 A | 2/1990 |
| EP | 04756784.7 | 1/2005 |
| WO | WO-99/24455 | 5/1999 |
| WO | WO-03/076932 A2 | 9/2003 |
| WO | WO-03076932 A2 | 9/2003 |
| WO | WO-2005/007822 | 1/2005 |

OTHER PUBLICATIONS

Giam et al. In vivo and in vitro autoprocessing of human immunodeficiency virus protease expressed in *Escherichia coli*. J Biol Chem. Oct. 15, 1988;263(29):14617-20.*

Tsukaguchi et al. Binding-, intracellular transport-, and biosynthesis-defective mutants of vasopressin type 2 receptor in patients with X-linked nephrogenic diabetes insipidus. J Clin Invest. Oct. 1995;96(4):2043-50.*

Phan et al. Structural basis for the substrate specificity of tobacco etch virus protease. J Biol Chem. Dec. 27, 2002;277(52):50564-72.*

Ferguson et al. Molecular mechanisms of G protein-coupled receptor desensitization and resensitization. Life Sci. 1998;62(17-18):1561-5.*

Parales et al. Enzyme specificity of 2-nitrotoluene 2,3-dioxygenase from *Pseudomonas* sp. strain JS42 is determined by the C-terminal region of the alpha subunit of the oxygenase component. J Bacteriol. Mar. 1998;180(5):1194-9.*

Hirowatari et al. A novel method for analysis of viral proteinase activity encoded by hepatitis C virus in cultured cells. Anal Biochem. Feb. 10, 1995;225(1):113-20.*

(Continued)

*Primary Examiner* — Michele Joike

(57) ABSTRACT

The invention relates to a method for determining if a test compound, or a mix of compounds, modulates the interaction between two proteins of interest. The determination is made possible via the use of two recombinant molecules, one of which contains the first protein a cleavage site for a proteolytic molecules, and an activator of a gene. The second recombinant molecule includes the second protein and the proteolytic molecule. If the test compound binds to the first protein, a reaction is initiated whereby the activator is cleaved, and activates a reporter gene.

23 Claims, 11 Drawing Sheets

OTHER PUBLICATIONS

White, M.A. The yeast two-hybrid system: forward and reverse. Proc Natl Acad Sci U S A. Sep. 17, 1996; 93(19): 10001-10003.*

Chalfie et al. Green fluorescent protein as a marker for gene expression. Science. Feb. 11, 1994;263(5148):802-5.*

EP06771518.5, "European Search Report mailed on Sep. 14, 2009", 5.

Fang, Y. et al., "Fabrication and Application of G Protein-Coupled Receptor Microarrays", *Methods in Molecular Biology* Human Press Inc, NJ, US, vol. 264 Jan. 1, 2004, 233-243.

PCT/US06/20810, "PCT Search Report mailed on Oct. 2, 2006", 5.

* cited by examiner

SEQUENCE LISTING

<160> NUMBER OF SEQ ID NOS: 101

<210> SEQ ID NO 1
<211> LENGTH: 2015
<212> TYPE: DNA
<213> ORGANISM: Homo sapiens

<400> SEQUENCE: 1

```
actgcgaagc ggcttcttca gagcacgggc tggaactggc aggcaccgcg agccctagc      60 acccgacaag ctgagtgtgc aggacgagtc cccaccacac ccacaccaca gccgctgaat     120
gaggcttcca ggcgtccgct cgcggcccgc agagcccgc cgtgggtccg cccgctgagg     180
cgcccccagc cagtgcgctt acctgccaga ctgcgcgcca tggggcaacc cgggaacggc     240
agcgccttct tgctggcacc caatagaagc catgcgccgg accacgacgt cacgcagcaa     300
agggacgagg tgtgggtggt gggcatgggc atcgtcatgt ctctcatcgt cctggccatc     360
gtgtttggca atgtgctggt catcacagcc attgccaagt cgagcgtct gcagacggtc     420 accaactact tcatcacttc actggcctgt gctgatctgg tcatgggcct ggcagtggtg     480
ccctttgggg ccgcccatat tcttatgaaa atgtggactt ttggcaactt ctggtgcgag     540
ttttggactt ccattgatgt gctgtgcgtc acggccagca ttgagaccct gtgcgtgatc     600
gcagtggatc gctactttgc cattacttca cctttcaagt accagagcct gctgaccaag     660
aataaggccc gggtgatcat tctgatggtg tggattgtgt caggccttac ctccttcttg     720
cccattcaga tgcactggta ccgggccacc caccaggaag ccatcaactg ctatgccaat     780
gagacctgct gtgacttctt cacgaaccaa gcctatgcca ttgcctcttc catcgtgtcc     840
ttctacgttc cctggtgat catggtcttc gtctactcca gggtctttca ggaggccaaa     900
```

-continued

```
aggcagctcc agaagattga caaatctgag ggccgcttcc atgtccagaa ccttagccag    960
gtggagcagg atgggcggac ggggcatgga ctccgcagat cttccaagtt ctgcttgaag   1020
gagcacaaag ccctcaagac gttaggcatc atcatgggca cttcacccct ctgctggctg   1080
cccttcttca tcgttaacat tgtgcatgtg atccaggata acctcatccg taaggaagtt   1140
tacatcctcc taaattggat aggctatgtc aattctggtt tcaatcccct tatctactgc   1200
cggagcccag atttcaggat tgccttccag gagcttctgt gcctgcgcag gtcttctttg   1260
aaggcctatg ggaatggcta ctccagcaac ggcaacacag gggagcagag tggatatcac   1320
gtggaacagg agaaagaaaa taaactgctg tgtgaagacc tcccaggcac ggaagacttt   1380
gtgggccatc aaggtactgt gcctagcgat aacattgatt cacaagggag gaattgtagt   1440
acaaatgact cactgctgta aagcagtttt tctacttta aagacccccc cccccccaac   1500
agaacactaa acagactatt taacttgagg gtaataaaact tagaataaaa ttgtaaaaat   1560
tgtatagaga tatgcagaag gaagggcatc cttctgcctt ttttattttt ttaagctgta   1620
aaaagagaga aaacttattt gagtgattat ttgttatttg tacagttcag ttcctctttg   1680
catggaattt gtaagtttat gtctaaagag ctttagtcct agaggacctg agtctgctat   1740
attttcatga cttttccatg tatctacctc actattcaag tattagggt aatatattgc    1800 tgctggtaat ttgtatctga aggagatttt ccttcctaca cccttggact tgaggatttt   1860
gagtatctcg gacctttcag ctgtgaacat ggactcttcc cccactcctc ttatttgctc   1920
acacggggta ttttaggcag ggatttgagg agcagcttca gttgttttcc cgagcaaagg   1980
tctaaagttt acagtaaata aaatgtttga ccatg                              2015
```

```
<210> SEQ ID NO 2
<211> LENGTH: 26
<212> TYPE: DNA
<213> ORGANISM: Homo Sapiens

<400> SEQUENCE: 2
gattgaagat ctgccttctt gctggc                                          26

<210> SEQ ID NO 3
<211> LENGTH: 27
<212> TYPE: DNA
<213> ORGANISM: Homo Sapiens

<400> SEQUENCE: 3
gcagaacttg gaagacctgc ggagtcc                                         27

<210> SEQ ID NO 4
<211> LENGTH: 27
<212> TYPE: DNA
<213> ORGANISM: Homo Sapiens

<400> SEQUENCE: 4
ggactccgca ggtcttccaa gttctgc                                         27

<210> SEQ ID NO 5
<211> LENGTH: 27
<212> TYPE: DNA
<213> ORGANISM: Homo Sapiens

<400> SEQUENCE: 5
ttcggatcct agcagtgagt catttgt                                         27
```

```
<210> SEQ ID NO 6
<211> LENGTH: 7
<212> TYPE: PRT
<213> ORGANISM: Homo Sapiens

<400> SEQUENCE: 6

Glu Asn Leu Tyr Phe Gln Ser
              5

<210> SEQ ID NO 7
<211> LENGTH: 32
<212> TYPE: DNA
<213> ORGANISM: Homo Sapiens

<400> SEQUENCE: 7
ccggatcctc tagattagat aaaagtaaag tg                              32

<210> SEQ ID NO 8
<211> LENGTH: 35
<212> TYPE: DNA
<213> ORGANISM: Homo Sapiens

<400> SEQUENCE: 8
gactcgagct agcagtatcc tcgcgccccc taccc                           35

<210> SEQ ID NO 9
<211> LENGTH: 18
<212> TYPE: DNA
<213> ORGANISM: Homo Sapiens

<400> SEQUENCE: 9
gagaacctgt acttccag                                              18

<210> SEQ ID NO 10
<211> LENGTH: 33
<212> TYPE: DNA
<213> ORGANISM: Homo Sapiens

<400> SEQUENCE: 10
ggatccgaga acctgtactt ccagtacaga tta                             33

<210> SEQ ID NO 11
<211> LENGTH: 30
<212> TYPE: DNA
<213> ORGANISM: Homo Sapiens

<400> SEQUENCE: 11
ctcgagagat cctcgcgccc cctacccacc                                 30

<210> SEQ ID NO 12
<211> LENGTH: 7
<212> TYPE: PRT
<213> ORGANISM: Homo Sapiens

<400> SEQUENCE: 12

Glu Asn Leu Tyr Phe Gln Tyr
              5

<210> SEQ ID NO 13
<211> LENGTH: 33
<212> TYPE: DNA
<213> ORGANISM: Homo Sapiens

<400> SEQUENCE: 13
ggatccgaga acctgtactt ccagctaaga tta                             33
```

<210> SEQ ID NO 14
<211> LENGTH: 7
<212> TYPE: PRT
<213> ORGANISM: Homo Sapiens

<400> SEQUENCE: 14

Glu Asn Leu Tyr Phe Gln Leu
            5

<210> SEQ ID NO 15
<211> LENGTH: 33
<212> TYPE: DNA
<213> ORGANISM: Homo Sapiens

<400> SEQUENCE: 15
gcggccgcca ccatgaacgg taccgaaggc cca                                33

<210> SEQ ID NO 16
<211> LENGTH: 21
<212> TYPE: DNA
<213> ORGANISM: Homo Sapiens

<400> SEQUENCE: 16
ctggtgggtg gcccggtacc a                                            21

<210> SEQ ID NO 17
<211> LENGTH: 1936
<212> TYPE: DNA
<213> ORGANISM: Homo sapiens

<400> SEQUENCE: 17
ccccgcgtgt ctgctaggag agggcgggca gcgccgcggc gcgcgcgatc cggctgacgc      60
atctggcccc ggttccccaa gaccagagcg gggccgggag ggaggggaa gaggcgagag     120
cgcggagggc gcgcgtgcgc attggcgcgg ggaggagcag ggatcttggc agcgggcgag    180
gaggctgcga gcgagccgcg aaccgagcgg gcggcgggcg cgcgcaccat ggggagaaa    240
cccgggacca gggtcttcaa gaagtcgagc cctaactgca agctcaccgt gtacttgggc    300
aagcggggact tcgtagatca cctggacaaa gtggaccctg tagatggcgt ggtgcttgtg    360
gaccctgact acctgaagga ccgcaaagtg tttgtgaccc tcacctgcgc cttccgctat    420
ggccgtgaag acctggatgt gctgggcttg tccttccgca agacctgtt catcgccacc    480
taccaggcct cccccccggt gcccaaccca ccccggcccc ccaccgcct gcaggaccgg    540
ctgctgagga agctgggcca gcatgcccac cccttcttct tcaccatacc ccagaatctt    600
ccatgctccg tcacactgca gccaggccca gaggatacag gaaaggcctg cggcgtagac    660
tttgagattc gagccttctg tgctaaatca ctagaagaga aaagccacaa aaggaactct    720
gtgcggctgg tgatccgaaa ggtgcagttc gccccggaga acccggcc cagccttca    780
gccgaaacca cacgccactt cctcatgtct gaccggtccc tgcacctcga ggcttccctg    840
gacaaggagc tgtactacca tggggagccc ctcaatgtaa atgtccacgt caccaacaac    900
tccaccaaga ccgtcaagaa gatcaaagtc tctgtgagac agtacgccga catctgcctc    960
ttcagcaccg cccagtacaa gtgtcctgtg gctcaactcg aacaagatga ccaggtatct   1020
cccagctcca cattctgtaa ggtgtacacc ataaccccac tgctcagcga caaccgggag   1080
aagcggggtc tcgccctgga tgggaaactc aagcacgagg acaccaacct ggcttccagc   1140
accatcgtga aggagggtgc caacaaggag gtgctgggaa tcctggtgtc ctacagggtc   1200

-continued

```
aaggtgaagc tggtggtgtc tcgaggcggg gatgtctctg tggagctgcc ttttgttctt    1260
atgcacccca agccccacga ccacatcccc ctccccagac cccagtcagc cgctccggag    1320
acagatgtcc ctgtggacac caacctcatt gaatttgata ccaactatgc cacagatgat    1380
gacattgtgt ttgaggactt tgcccggctt cggctgaagg ggatgaagga tgacgactat    1440
gatgatcaac tctgctagga agcggggtgg gaagaaggga ggggatgggg ttgggagagg    1500
tgagggcagg attaagatcc ccactgtcaa tggggattg tcccagcccc tcttcccttc     1560
ccctcacctg gaagcttctt caaccaatcc cttcacactc tctcccccat cccccaaga    1620 tacacactgg accctctctt gctgaatgtg ggcattaatt ttttgactgc agctctgctt    1680
ctccagcccc gccgtgggtg gcaagctgtg ttcatacctt aattttctgg aaggggacag    1740
tgaaaagagg agtgacagga gggaaagggg gagacaaaac tcctactctc aacctcacac    1800
caacacctcc cattatcact ctctctgccc ccattccttc aagaggagac cctttgggga    1860
caaggccgtt tctttgtttc tgagcataaa gaagaaaata aatctttac taagcatgaa     1920 aaaaaaaaaa aaaaaa                                                    1936

<210> SEQ ID NO 18
<211> LENGTH: 35
<212> TYPE: DNA
<213> ORGANISM: Homo Sapiens

<400> SEQUENCE: 18
caggatcctc tggaatgggg gagaaacccg ggacc                                35

<210> SEQ ID NO 19
<211> LENGTH: 30
<212> TYPE: DNA
<213> ORGANISM: Homo Sapiens

<400> SEQUENCE: 19
ggatccgcag agttgatcat catagtcgtc                                      30

<210> SEQ ID NO 20
<211> LENGTH: 9
<212> TYPE: PRT
<213> ORGANISM: Homo Sapiens

<400> SEQUENCE: 20

Tyr Pro Tyr Asp Val Pro Asp Tyr Ala
                5

<210> SEQ ID NO 21
<211> LENGTH: 28
<212> TYPE: DNA
<213> ORGANISM: Homo Sapiens

<400> SEQUENCE: 21
agatctagct tgtttaaggg accacgtg                                        28

<210> SEQ ID NO 22
<211> LENGTH: 62
<212> TYPE: DNA
<213> ORGANISM: Homo Sapiens

<400> SEQUENCE: 22
gcggccgctc aagcgtaatc tggaacatca tatgggtacg agtacaccaa ttcattcatg    60
ag                                                                    62
```

<210> SEQ ID NO 23
<211> LENGTH: 1809
<212> TYPE: DNA
<213> ORGANISM: Homo sapiens

<400> SEQUENCE: 23

```
agaagatcct gggttctgtg catccgtctg tctgaccatc cctctcaatc ttccctgccc      60
aggactggcc atactgccac cgcacacgtg cacacacgcc aacaggcatc tgccatgctg     120
gcatctctat aagggctcca gtccagagac cctgggccat tgaacttgct cctcaggcag     180
aggctgagtc cgcacatcac ctccaggccc tcagaacacc tgccccagcc ccaccatgct     240
catggcgtcc accacttccg ctgtgcctgg gcatccctct ctgcccagcc tgcccagcaa     300
cagcagccag gagaggccac tggacacccg ggacccgctg ctagcccggg cggagctggc     360
gctgctctcc atagtctttg tggctgtggc cctgagcaat ggcctggtgc tggcggccct     420
agctcggcgg ggccggcggg gccactgggc acccatacac gtcttcattg gccacttgtg     480
cctggccgac ctggccgtgg ctctgttcca agtgctgccc cagctggcct ggaaggccac     540
cgaccgcttc cgtgggccag atgccctgtg tcgggccgtg aagtatctgc agatggtggg     600
catgtatgcc tcctcctaca tgatcctggc catgacgctg accgccacc gtgccatctg     660
ccgtcccatg ctggcgtacc gccatggaag tggggctcac tggaaccggc cggtgctagt     720
ggcttgggcc ttctcgctcc ttctcagcct gccccagctc ttcatcttcg cccagcgcaa     780
cgtggaaggt ggcagcgggg tcactgactg ctgggcctgc tttgcggagc cctggggccg     840
tcgcacctat gtcacctgga ttgccctgat ggtgttcgtg gcacctaccc tgggtatcgc     900
cgcctgccag gtgctcatct ccgggagat tcatgccagt ctggtgccag gccatcaga     960
gaggcctggg gggcgccgca ggggacgccg gacaggcagc cccggtgagg agcccacgt    1020
gtcagcagct gtggccaaga ctgtgaggat gacgctagtg attgtggtcg tctatgtgct    1080
gtgctgggca cccttcttcc tggtgcagct gtgggccgcg tgggaccggg aggcacctct    1140
ggaagggcg ccctttgtgc tactcatgtt gctggccagc ctcaacagct gcaccaaccc    1200
ctggatctat gcatctttca gcagcagcgt gtcctcagag ctgcgaagct tgctctgctg    1260
tgcccgggga cgcaccccac ccagcctggg tccccaagat gagtcctgca ccaccgccag    1320
ctcctcctg gccaaggaca cttcatcgtg aggagctgtt gggtgtcttg cctctagagg    1380
ctttgagaag ctcagctgcc ttcctggggc tggtcctggg agccactggg aggggaccc    1440
gtggagaatt ggccagagcc tgtggccccg aggctgggac actgtgtggc cctgacaag    1500
ccacagcccc tgcctgggtc tccacatccc cagctgtatg aggagagctt caggccccag    1560
gactgtgggg gccctcagg tcagctcact gagctgggtg taggagggc tgcagcagag    1620
gcctgaggag tggcaggaaa gagggagcag gtgcccccag gtgagacagc ggtcccaggg    1680
gcctgaaaag gaaggaccag gctggggcca gggaccttc ctgtctccgc ctttctaatc    1740
cctccctcct cattctctcc ctaataaaaa ttggagctct tttccacatg gcaagggtc    1800
tccttggaa                                                          1809
```

<210> SEQ ID NO 24
<211> LENGTH: 26
<212> TYPE: DNA
<213> ORGANISM: Homo Sapiens

<400> SEQUENCE: 24

```
gaattcatgc tcatggcgtc caccac                                         26
```

<210> SEQ ID NO 25
<211> LENGTH: 27
<212> TYPE: DNA
<213> ORGANISM: Homo Sapiens

<400> SEQUENCE: 25
ggatcccgat gaagtgtcct tggccag                                           27

<210> SEQ ID NO 26
<211> LENGTH: 1266
<212> TYPE: DNA
<213> ORGANISM: Homo sapiens

<400> SEQUENCE: 26

```
atggatgtgc tcagccctgg tcagggcaac aacaccacat caccaccggc tcccttttgag    60
accggcggca acactactgg tatctccgac gtgaccgtca gctaccaagt gatcacctct   120
ctgctgctgg gcacgctcat cttctgcgcg gtgctgggca tgcgtgcgt ggtggctgcc    180
atcgccttgg agcgctccct gcagaacgtg gccaattatc ttattggctc tttggcggtc   240
accgacctca tggtgtcggt gttggtgctg cccatggccg cgctgtatca ggtgctcaac   300
aagtggacac tgggccaggt aacctgcgac ctgttcatcg ccctcgacgt gctgtgctgc   360
acctcatcca tcttgcacct gtgcgccatc gcgctggaca ggtactgggc catcacggac   420
cccatcgact acgtgaacaa gaggacgccc cggccgcgtg cgctcatctc gctcacttgg   480
cttattggct tcctcatctc tatcccgccc atcctgggct ggcgcacccc ggaagaccgc   540
tcggaccccg acgcatgcac cattagcaag gatcatggct acactatcta ttccaccttt   600
ggagctttct acatcccgct gctgctcatg ctggttctct atgggcgcat attccgagct   660
gcgcgcttcc gcatccgcaa gacggtcaaa aaggtggaga agaccggagc ggacacccgc    720
catggagcat ctcccgcccc gcagcccaag aagagtgtga atggagagtc ggggagcagg   780
aactggaggc tgggcgtgga gagcaaggct gggggtgctc tgtgcgccaa tggcgcggtg   840
aggcaaggtg acgatggcgc cgccctggag gtgatcgagg tgcaccgagt gggcaactcc   900
aaagagcact tgcctctgcc cagcgaggct ggtcctaccc cttgtgcccc cgcctctttc   960
gagaggaaaa atgagcgcaa cgccgaggcg aagcgcaaga tggccctggc ccgagagagg  1020
aagacagtga gacgctggg catcatcatg ggcaccttca tcctctgctg gctgcccttc   1080
ttcatcgtgg ctcttgttct gcccttctgc gagagcagct gccacatgcc caccctgttg   1140
ggcgccataa tcaattggct gggctactcc aactctctgc ttaacccgt catttacgca   1200
tacttcaaca aggactttca aaacgcgttt aagaagatca ttaagtgtaa cttctgccgc   1260
cagtga                                                              1266
```

<210> SEQ ID NO 27
<211> LENGTH: 26
<212> TYPE: DNA
<213> ORGANISM: Homo Sapiens

<400> SEQUENCE: 27
gaattcatgg atgtgctcag ccctgg                                            26

<210> SEQ ID NO 28
<211> LENGTH: 25
<212> TYPE: DNA
<213> ORGANISM: Homo Sapiens

<400> SEQUENCE: 28
ggatccctgg cggcagaact tacac                                             25

<210> SEQ ID NO 29
<211> LENGTH: 1401
<212> TYPE: DNA
<213> ORGANISM: Homo Sapiens

<400> SEQUENCE: 29

| | | | | | |
|---|---|---|---|---|---|
| atgaataact | caacaaactc | ctctaacaat | agcctggctc | ttacaagtcc | ttataagaca | 60 |
| tttgaagtgg | tgtttattgt | cctggtggct | ggatccctca | gtttggtgac | cattatcggg | 120 |
| aacatcctag | tcatggtttc | cattaaagtc | aaccgccacc | tccagaccgt | caacaattac | 180 |
| tttttattca | gcttggcctg | tgctgacctt | atcataggtg | ttttctccat | gaacttgtac | 240 |
| accctctaca | ctgtgattgg | ttactggcct | ttgggacctg | tggtgtgtga | cctttggcta | 300 |
| gccctggact | atgtggtcag | caatgcctca | gttatgaatc | tgctcatcat | cagctttgac | 360 |
| aggtacttct | gtgtcacaaa | acctctgacc | tacccagtca | agcggaccac | aaaaatggca | 420 |
| ggtatgatga | ttgcagctgc | ctgggtcctc | tctttcatcc | tctgggctcc | agccattctc | 480 |
| ttctggcagt | tcattgtagg | ggtgagaact | gtggaggatg | gggagtgcta | cattcagttt | 540 |
| ttttccaatg | ctgctgtcac | ctttggtacg | gctattgcag | ccttctattt | gccagtgatc | 600 |
| atcatgactg | tgctatattg | gcacatatcc | gagccagca | agagcaggat | aaagaaggac | 660 |
| aagaaggagc | ctgttgccaa | ccaagacccc | gtttctccaa | gtctggtaca | aggaaggata | 720 |
| gtgaagccaa | acaataacaa | catgcccagc | agtgacgatg | gcctggagca | caacaaaatc | 780 |
| cagaatggca | aagcccccag | ggatcctgtg | actgaaaact | gtgttcaggg | agaggagaag | 840 |
| gagagctcca | atgactccac | ctcagtcagt | gctgttgcct | ctaatatgag | agatgatgaa | 900 |
| ataacccagg | atgaaaacac | agtttccact | tccctgggcc | attccaaaga | tgagaactct | 960 |
| aagcaaacat | gcatcagaat | tggcaccaag | accccaaaaa | gtgactcatg | taccccaact | 1020 |
| aataccaccg | tggaggtagt | ggggtcttca | ggtcagaatg | agatgaaaa | gcagaatatt | 1080 |
| gtagcccgca | agattgtgaa | gatgactaag | cagcctgcaa | aaagaagcc | tcctccttcc | 1140 |
| cgggaaaaga | aagtcaccag | gacaatcttg | gctattctgt | tggctttcat | catcacttgg | 1200 |
| gccccataca | atgtcatggt | gctcattaac | accttttgtg | caccttgcat | ccccaacact | 1260 |
| gtgtggacaa | ttggttactg | gctttgttac | atcaacagca | ctatcaaccc | tgcctgctat | 1320 |
| gcactttgca | atgccacctt | caagaagacc | tttaaacacc | ttctcatgtg | tcattataag | 1380 |
| aacataggcg | ctacaaggta | a | | | | 1401 |

<210> SEQ ID NO 30
<211> LENGTH: 27
<212> TYPE: DNA
<213> ORGANISM: Homo Sapiens

<400> SEQUENCE: 30
gaattcatga ataactcaac aaactcc         27

<210> SEQ ID NO 31
<211> LENGTH: 25
<212> TYPE: DNA
<213> ORGANISM: Homo Sapiens

<400> SEQUENCE: 31
agatctcctt gtagcgccta tgttc         25

<210> SEQ ID NO 32
<211> LENGTH: 3655

<212> TYPE: DNA
<213> ORGANISM: Homo sapiens

<400> SEQUENCE: 32

```
cttcagatag attatatctg gagtgaagga tcctgccacc tacgtatctg gcatagtatt      60
ctgtgtagtg ggatgagcag agaacaaaaa caaaataatc cagtgagaaa agcccgtaaa     120
taaaccttca gaccagagat ctattctcca gcttatttta agctcaactt aaaaagaaga     180
actgttctct gattcttttc gccttcaata cacttaatga tttaactcca ccctccttca     240
aaagaaacag catttcctac ttttatactg tctatatgat tgatttgcac agctcatctg     300
gccagaagag ctgagacatc cgttcccta caagaaactc tccccgggtg aacaagatg      360
gattatcaag tgtcaagtcc aatctatgac atcaattatt atacatcgga gccctgccaa     420
aaaatcaatg tgaagcaaat cgcagcccgc ctcctgcctc cgctctactc actggtgttc     480
atctttggtt ttgtgggcaa catgctggtc atcctcatcc tgataaactg caaaaggctg     540
aagagcatga ctgacatcta cctgctcaac ctggccatct ctgacctgtt tttccttctt     600
actgtcccct tctgggctca ctatgctgcc gcccagtggg actttggaaa tacaatgtgt     660
caactcttga cagggctcta ttttataggc ttcttctctg gaatcttctt catcatcctc     720
ctgacaatcg ataggtacct ggctgtcgtc catgctgtgt tgctttaaa agccaggacg     780
gtcacctttg gggtggtgac aagtgtgatc acttgggtgg tggctgtgtt tgcgtctctc     840
ccaggaatca tctttaccag atctcaaaaa gaaggtcttc attacacctg cagctctcat     900
tttccataca gtcagtatca attctggaag aatttccaga cattaaagat agtcatcttg     960
gggctggtcc tgccgctgct tgtcatggtc atctgctact cgggaatcct aaaaactctg    1020
cttcggtgtc gaaatgagaa gaagaggcac agggctgtga ggcttatctt caccatcatg    1080
attgtttatt ttctcttctg ggctccctac aacattgtcc ttctcctgaa caccttccag    1140
gaattctttg gcctgaataa ttgcagtagc tctaacaggt tggaccaagc tatgcaggtg    1200
acagagactc ttgggatgac gcactgctgc atcaacccca tcatctatgc ctttgtcggg    1260
gagaagttca gaaactacct cttagtcttc ttccaaaagc acattgccaa acgcttctgc    1320
aaatgctgtt ctatttttcca gcaagaggct cccgagcgag caagctcagt ttacacccga    1380
tccactgggg agcaggaaat atctgtgggc ttgtgcacg gactcaagtg gctggtgac     1440
ccagtcagag ttgtgcacat ggcttagttt tcatacacag cctgggctgg gggtggggtg    1500
ggagaggtct tttttaaaag gaagttactg ttatagaggg tctaagattc atccattat     1560
ttggcatctg tttaaagtag attagatctt ttaagcccat caattataga aagccaaatc    1620
aaaatatgtt gatgaaaaat agcaaccttt ttatctcccc ttcacatgca tcaagttatt    1680
gacaaactct cccttcactc cgaaagttcc ttatgtatat ttaaaagaaa gcctcagaga    1740
attgctgatt cttgagttta gtgatctgaa cagaaatacc aaaattattt cagaaatgta    1800
caactttta cctagtacaa ggcaacatat aggttgtaaa tgtgtttaaa acaggtcttt     1860
gtcttgctat ggggagaaaa gacatgaata tgattagtaa agaaatgaca cttttcatgt    1920
gtgatttccc ctccaaggta tggttaataa gtttcactga cttagaacca ggcgagagac    1980
ttgtggcctg ggagagctgg ggaagcttct taaatgagaa ggaatttgag ttggatcatc    2040
tattgctggc aaagacagaa gcctcactgc aagcactgca tgggcaagct tggctgtaga    2100
aggagacaga gctggttggg aagacatggg gaggaaggac aaggctagat catgaagaac    2160
cttgacggca ttgctccgtc taagtcatga gctgagcagg gagatcctgg ttggtgttgc    2220
agaaggttta ctctgtggcc aaaggagggt caggaaggat gagcatttag ggcaaggaga    2280
```

```
ccaccaacag ccctcaggtc agggtgagga tggcctctgc taagctcaag gcgtgaggat      2340
gggaaggagg gaggtattcg taaggatggg aaggagggag gtattcgtgc agcatatgag      2400
gatgcagagt cagcagaact ggggtggatt tggtttggaa gtgagggtca gagaggagtc      2460
agagagaatc cctagtcttc aagcagattg gagaaaccct tgaaaagaca tcaagcacag      2520
aaggaggagg aggaggttta ggtcaagaag aagatggatt ggtgtaaaag gatgggtctg      2580
gtttgcagag cttgaacaca gtctcaccca gactccaggc tgtctttcac tgaatgcttc      2640
tgacttcata gatttccttc ccatcccagc tgaaatactg aggggtctcc aggaggagac      2700
tagatttatg aatacacgag gtatgaggtc taggaacata cttcagctca cacatgagat      2760
ctaggtgagg attgattacc tagtagtcat ttcatgggtt gttgggagga ttctatgagg      2820
caaccacagg cagcatttag cacatactac acattcaata agcatcaaac tcttagttac      2880
tcattcaggg atagcactga gcaaagcatt gagcaaaggg gtcccatata ggtgagggaa      2940
gcctgaaaaa ctaagatgct gcctgcccag tgcacacaag tgtaggtatc atttctgca       3000 tttaaccgtc aataggcaaa gggggggaagg gacatattca tttggaaata agctgccttg      3060
agccttaaaa cccacaaaag tacaatttac cagcctccgt atttcagact gaatgggggt      3120
ggggggggcg ccttaggtac ttattccaga tgccttctcc agacaaacca gaagcaacag      3180
aaaaaatcgt ctctccctcc ctttgaaatg aatatacccc ttagtgtttg ggtatattca      3240
tttcaaaggg agagagagag gttttttttct gttctttctc atatgattgt gcacatactt      3300
gagactgttt tgaatttggg ggatggctaa aaccatcata gtacaggtaa ggtgagggaa      3360
tagtaagtgg tgagaactac tcagggaatg aaggtgtcag aataataaga ggtgctactg      3420
actttctcag cctctgaata tgaacggtga gcattgtggc tgtcagcagg aagcaacgaa      3480
gggaaatgtc tttcctttttg ctcttaagtt gtggagagtg caacagtagc ataggaccct      3540
accctctggg ccaagtcaaa gacattctga catcttagta tttgcatatt cttatgtatg      3600
tgaaagttac aaattgcttg aaagaaaata tgcatctaat aaaaaacacc ttcta          3655
```

<210> SEQ ID NO 33
<211> LENGTH: 31
<212> TYPE: DNA
<213> ORGANISM: Homo Sapiens

<400> SEQUENCE: 33

```
gcggccgcat ggattatcaa gtgtcaagtc c                                     31
```

<210> SEQ ID NO 34
<211> LENGTH: 25
<212> TYPE: DNA
<213> ORGANISM: Homo Sapiens

<400> SEQUENCE: 34

```
ggatccctgg cggcagaact tacac                                            25
```

<210> SEQ ID NO 35
<211> LENGTH: 33
<212> TYPE: DNA
<213> ORGANISM: Homo Sapiens

<400> SEQUENCE: 35

```
ggtctccaat tcatggatta tcaagtgtca agt                                   33
```

<210> SEQ ID NO 36
<211> LENGTH: 21

<212> TYPE: DNA
<213> ORGANISM: Homo Sapiens

<400> SEQUENCE: 36

```
gacgacagcc aggtacctat c                                       21
```

<210> SEQ ID NO 37
<211> LENGTH: 2643
<212> TYPE: DNA
<213> ORGANISM: Homo sapiens

<400> SEQUENCE: 37

```
ggcagccgtc cggggccgcc actctcctcg gccggtccct ggctcccgga ggcggccgcg    60
cgtggatgcg gcgggagctg aagcctcaa gcagccggcg ccgtctctgc cccggggcgc   120
cctatggctt gaagagcctg ccacccagt ggctccaccg ccctgatgga tccactgaat   180
ctgtcctggt atgatgatga tctggagagg cagaactgga gccggccctt caacgggtca   240
gacgggaagg cggacagacc ccactacaac tactatgcca cactgctcac cctgctcatc   300
gctgtcatcg tcttcggcaa cgtgctggtg tgcatggctg tgtcccgcga aaggcgctg   360
cagaccacca ccaactacct gatcgtcagc ctcgcagtgg ccgacctcct cgtcgccaca   420
ctggtcatgc cctgggttgt ctacctggag gtggtaggtg agtggaaatt cagcaggatt   480
cactgtgaca tcttcgtcac tctggacgtc atgatgtgca cggcgagcat cctgaacttg   540
tgtgccatca gcatcgacag gtacacagct gtggccatgc ccatgctgta caatacgcgc   600
tacagctcca agcgccgggt caccgtcatg atctccatcg tctgggtcct gtccttcacc   660
atctcctgcc cactcctctt cggactcaat aacgcagacc agaacgagtg catcattgcc   720
aacccggcct tcgtggtcta ctcctccatc gtctccttct acgtgccctt cattgtcacc   780
ctgctggtct acatcaagat ctacattgtc ctccgcagac gccgcaagcg agtcaacacc   840
aaacgcagca gccgagcttt cagggcccac ctgagggctc cactaaaggg caactgtact   900
caccccgagg acatgaaact ctgcaccgtt atcatgaagt ctaatgggag tttcccagtg   960
aacaggcgga gagtggaggc tgcccggcga gccaggagc tggagatgga gatgctctcc  1020
agcaccagcc cacccgagag gacccggtac agccccatcc cacccagcca ccaccagctg  1080
actctccccg acccgtccca ccatggtctc cacagcactc ccgacagccc cgccaaacca  1140
gagaagaatg ggcatgccaa agaccacccc aagattgcca agatctttga gatccagacc  1200
atgcccaatg gcaaaacccg gacctccctc aagaccatga gccgtaggaa gctctcccag  1260
cagaaggaga agaaagccac tcagatgctc gccattgttc tcggcgtgtt catcatctgc  1320
tggctgccct tcttcatcac acacatcctg aacatacact gtgactgcaa catcccgcct  1380
gtcctgtaca gcgccttcac gtggctgggc tatgtcaaca gcgccgtgaa ccccatcatc  1440
tacaccacct tcaacattga gttccgcaag gccttcctga agatcctcca ctgctgactc  1500
tgctgcctgc ccgcacagca gcctgcttcc cacctccctg cccaggccgg ccagcctcac  1560
ccttgcgaac cgtgagcagg aaggcctggg tggatcggcc tcctcttcac cccggcaggc  1620
cctgcagtgt tcgcttggct ccatgctcct cactgcccgc acaccctcac tctgccaggg  1680
cagtgctagt gagctgggca tggtaccagc cctggggctg gccccccag ctcaggggca  1740
gctcatagag tcccccctcc cacctccagt ccccctatcc ttggcaccaa agatgcagcc  1800
gccttccttg accttcctct ggggctctag ggttgctgga gcctgagtca gggcccagag  1860
gctgagtttt ctctttgtgg ggcttggcgt ggagcaggcg gtggggagag atggacagtt  1920
cacacccctg c aaggcccaca ggaggcaagc aagctctctt gccgaggagc caggcaactt  1980
```

```
cagtcctggg agacccatgt aaataccaga ctgcaggttg accccagag attcccaagc      2040 caaaaacctt agctccctcc cgcaccccga tgtggacctc tactttccag gctagtccgg      2100
acccacctca ccccgttaca gctccccaag tggtttccac atgctctgag aagaggagcc      2160
ctcatcttga agggcccagg agggtctatg gggagaggaa ctccttggcc tagcccaccc      2220
tgctgccttc tgacgcccct gcaatgtatc ccttctcaca gcacatgctg gccagcctgg      2280
ggcctggcag ggaggtcagg ccctggaact ctatctgggc ctgggctagg ggacatcaga      2340
ggttctttga gggactgcct ctgccacact ctgacgcaaa accactttcc ttttctattc      2400
cttctggcct ttcctctctc ctgtttccct tcccttccac tgcctctgcc ttagaggagc      2460
ccacggctaa gaggctgctg aaaaccatct ggcctggcct ggccctgccc tgaggaagga      2520
ggggaagctg cagcttggga gagcccctgg ggcctagact ctgtaacatc actatccatg      2580
caccaaacta ataaaacttt gacgagtcac cttccaggac ccctgggtaa aaaaaaaaa      2640 aaa                                                                    2643

<210> SEQ ID NO 38
<211> LENGTH: 27
<212> TYPE: DNA
<213> ORGANISM: Homo Sapiens

<400> SEQUENCE: 38
gaattcatgg atccactgaa tctgtcc                                            27

<210> SEQ ID NO 39
<211> LENGTH: 25
<212> TYPE: DNA
<213> ORGANISM: Homo Sapiens

<400> SEQUENCE: 39
agatctgcag tggaggatct tcagg                                              25

<210> SEQ ID NO 40
<211> LENGTH: 1301
<212> TYPE: DNA
<213> ORGANISM: Homo sapiens

<400> SEQUENCE: 40
atgggcgaca aagggacgcg agtgttcaag aaggccagtc caaatggaaa gctcaccgtc        60
tacctgggaa agcgggactt tgtggaccac atcgacctcg tggaccctgt ggatggtgtg       120
gtcctggtgg atcctgagta tctcaaagag cggagagtct atgtgacgct gacctgcgcc       180
ttccgctatg gccgggagga cctggatgtc ctgggcctga ctttcgcaa ggacctgttt       240 gtggccaacg tacagtcgtt cccaccggcc cccgaggaca agaagcccct gacgcggctg       300
caggaacgcc tcatcaagaa gctgggcgag cacgcttacc ctttcacctt tgagatccct       360
ccaaaccttc catgttctgt gacactgcag ccggggcccg aagacacggg gaaggcttgc       420
ggtgtggact atgaagtcaa agccttctgc gcggagaatt tggaggagaa gatccacaag       480
cggaattctg tgcgtctggt catccggaag gttcagtatg cccagagag gcctggcccc       540 cagcccacag ccgagaccac caggcagttc ctcatgtcgg acaagccctt gcacctagaa       600
gcctctctgg ataaggagat ctattaccat ggagaaccca tcagcgtcaa cgtccacgtc       660
accaacaaca ccaacaagac ggtgaagaag atcaagatct cagtcgcca gtatgcagac       720 atctgccttt tcaacacagc tcagtacaag tgccctgttg ccatggaaga ggctgatgac       780
actgtggcac ccagctcgac gttctgcaag gtctacacac tgacccccctt cctagccaat       840
```

-continued

```
aaccgagaga agcggggcct cgccttggac gggaagctca agcacgaaga cacgaacttg      900
gcctctagca ccctgttgag ggaaggtgcc aaccgtgaga tcctggggat cattgtttcc      960
tacaaagtga aagtgaagct ggtggtgtct cggggcggcc tgttgggaga tcttgcatcc     1020
agcgacgtgg ccgtggaact gcccttcacc ctaatgcacc ccaagcccaa agaggaaccc     1080
ccgcatcggg aagttccaga gaacgagacg ccagtagata ccaatctcat agaacttgac     1140
acaaatgatg acgacattgt atttgaggac tttgctcgcc agagactgaa aggcatgaag     1200
gatgacaagg aggaagagga ggatggtacc ggctctccac agctcaacaa cagatagacg     1260
ggccggccct gcctccacgt ggctccggct ccactctcgt g                         1301
```

<210> SEQ ID NO 41
<211> LENGTH: 30
<212> TYPE: DNA
<213> ORGANISM: Homo Sapiens

<400> SEQUENCE: 41

```
ggtaccatgg gcgacaaagg gacgcgagtg                                        30
```

<210> SEQ ID NO 42
<211> LENGTH: 48
<212> TYPE: DNA
<213> ORGANISM: Homo Sapiens

<400> SEQUENCE: 42

```
ggatcctctg ttgttgagct gtggagagcc tgtaccatcc tcctcttc                   48
```

<210> SEQ ID NO 43
<211> LENGTH: 27
<212> TYPE: DNA
<213> ORGANISM: Homo Sapiens

<400> SEQUENCE: 43

```
ggatccattt gtgtcaagtt ctatgag                                          27
```

<210> SEQ ID NO 44
<211> LENGTH: 27
<212> TYPE: DNA
<213> ORGANISM: Homo Sapiens

<400> SEQUENCE: 44

```
ggtaccatgg gggagaaacc cgggacc                                          27
```

<210> SEQ ID NO 45
<211> LENGTH: 24
<212> TYPE: DNA
<213> ORGANISM: Homo Sapiens

<400> SEQUENCE: 45

```
ggatcctgtg gcatagttgg tatc                                             24
```

<210> SEQ ID NO 46
<211> LENGTH: 33
<212> TYPE: DNA
<213> ORGANISM: Homo Sapiens

<400> SEQUENCE: 46

```
tgtgcgcgcg gacgcacccc acccagcctg ggt                                   33
```

<210> SEQ ID NO 47
<211> LENGTH: 27

```
<212> TYPE: DNA
<213> ORGANISM: Homo Sapiens

<400> SEQUENCE: 47
gaattcatgg atccactgaa tctgtcc                                          27

<210> SEQ ID NO 48
<211> LENGTH: 33
<212> TYPE: DNA
<213> ORGANISM: Homo Sapiens

<400> SEQUENCE: 48
tgtgcgcgcg cagtggagga tcttcaggaa ggc                                   33

<210> SEQ ID NO 49
<211> LENGTH: 33
<212> TYPE: DNA
<213> ORGANISM: Homo Sapiens

<400> SEQUENCE: 49
gcggccgcca ccatgaacgg taccgaaggc cca                                   33

<210> SEQ ID NO 50
<211> LENGTH: 30
<212> TYPE: DNA
<213> ORGANISM: Homo Sapiens

<400> SEQUENCE: 50
tgtgcgcgcg cacagaagct cctggaaggc                                       30

<210> SEQ ID NO 51
<211> LENGTH: 1602
<212> TYPE: DNA
<213> ORGANISM: Homo sapiens

<400> SEQUENCE: 51
gagctccgtg ctgggaggtg ggaagggggc ttgaccctgg ggactcaggc agtctgggga      60
cagttccacc aggggccggt gcctagaatt ggtgagggag gcacctcagg ggctggggga     120
gaaggaacga gcgctcttcg cccctctctg gcacccagcg gcgcgcctgc tggccggaaa     180
ggcagcgaga agtccgttct ccctgtcctg ccccggcga cttgcggccc gggtgggagt      240
ccgcaggctc cgggtcccca gcgccgctgg ccagggcgcg ggcaaagttt gcctctccgc     300
gtccagccgg ttctttcgct cccgcagcgc gcaggtgcc gcctgtcctc gccttcctgc      360
tgcaatcgcc ccaccatgga ctccccgatc cagatcttcc gcggggagcc gggccctacc     420
tgcgccccga gcgcctgcct gccccccaac agcagcgcct ggtttcccgg ctgggccgag     480
cccgacagca acggcagcgc cggctcggag gacgcgcagc tggagcccgc gcacatctcc     540
ccggccatcc cggtcatcat cacgcgggtc tactccgtag tgttcgtcgt gggcttggtg     600
ggcaactcgc tggtcatgtt cgtgatcatc cgatacacaa agatgaagac agcaaccaac     660
atttacatat ttaacctggc tttggcagat gctttagtta ctacaaccat gcccttccag     720
agtacggtct acttgatgaa ttcctggcct tttgggatg tgctgtgcaa gatagtaatt     780
tccattgatt actacaacat gttcaccagc atcttcacct tgaccatgat gagcgtggac     840
cgctacattg ccgtgtgcca ccccgtgaag gctttggact ccgcacacc cttgaaggca     900
aagatcatca atatctgcat ctggctgctg tcgtcatctg ttggcatctc tgcaatagtc     960
cttggaggca ccaaagtcag ggaagacgtc gatgtcattg agtgctcctt gcagttccca    1020
gatgatgact actcctggtg ggacctcttc atgaagatct gcgtcttcat ctttgccttc    1080
```

```
gtgatccctg tcctcatcat catcgtctgc tacaccctga tgatcctgcg tctcaagagc    1140
gtccggctcc tttctggctc ccgagagaaa gatcgcaacc tgcgtaggat caccagactg    1200
gtcctggtgg tggtggcagt cttcgtcgtc tgctggactc ccattcacat attcatcctg    1260
gtggaggctc tggggagcac ctcccacagc acagctgctc tctccagcta ttacttctgc    1320
atcgccttag ctataccaa cagtagcctg aatcccattc tctacgcctt tcttgatgaa     1380
aacttcaagc ggtgtttccg ggacttctgc tttccactga agatgaggat ggagcggcag    1440
agcactagca gagtccgaaa tacagttcag gatcctgctt acctgaggga catcgatggg    1500
atgaataaac cagtatgact agtcgtggag atgtcttcgt acagttcttc gggaagagag    1560
gagttcaatg atctaggttt aactcagatc actactgcag tc                       1602
```

<210> SEQ ID NO 52
<211> LENGTH: 24
<212> TYPE: DNA
<213> ORGANISM: Homo Sapiens

<400> SEQUENCE: 52

```
ggtctacttg atgaattcct ggcc                                             24
```

<210> SEQ ID NO 53
<211> LENGTH: 27
<212> TYPE: DNA
<213> ORGANISM: Homo Sapiens

<400> SEQUENCE: 53

```
gcgcgcacag aagtcccgga aacaccg                                          27
```

<210> SEQ ID NO 54
<211> LENGTH: 10
<212> TYPE: PRT
<213> ORGANISM: Homo Sapiens

<400> SEQUENCE: 54

Gly Ser Glu Asn Leu Tyr Phe Gln Leu Arg
              5                  10

<210> SEQ ID NO 55
<211> LENGTH: 881
<212> TYPE: PRT
<213> ORGANISM: Homo sapiens

<400> SEQUENCE: 55

Met Lys Leu Leu Ser Ser Ile Glu Gln Ala Cys Asp Ile Cys Arg Leu
  1               5                  10                  15

Lys Lys Leu Lys Cys Ser Lys Glu Lys Pro Lys Cys Ala Lys Cys Leu
             20                  25                  30

Lys Asn Asn Trp Glu Cys Arg Tyr Ser Pro Lys Thr Lys Arg Ser Pro
         35                  40                  45

Leu Thr Arg Ala His Leu Thr Glu Val Glu Ser Arg Leu Glu Arg Leu
     50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                 85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser

```
                  115                 120                 125
Ala Thr Ser Ser Ser Glu Glu Ser Ser Asn Lys Gly Gln Arg Gln Leu
        130                 135                 140
Thr Val Ser Ile Asp Ser Ala Ala His His Asp Asn Ser Thr Ile Pro
145                 150                 155                 160
Leu Asp Phe Met Pro Arg Asp Ala Leu His Gly Phe Asp Trp Ser Glu
                165                 170                 175
Glu Asp Asp Met Ser Asp Gly Leu Pro Phe Leu Lys Thr Asp Pro Asn
            180                 185                 190
Asn Asn Gly Phe Phe Gly Asp Gly Ser Leu Leu Cys Ile Leu Arg Ser
                195                 200                 205
Ile Gly Phe Lys Pro Glu Asn Tyr Thr Asn Ser Asn Val Asn Arg Leu
        210                 215                 220
Pro Thr Met Ile Thr Asp Arg Tyr Thr Leu Ala Ser Arg Ser Thr Thr
225                 230                 235                 240
Ser Arg Leu Leu Gln Ser Tyr Leu Asn Asn Phe His Pro Tyr Cys Pro
                245                 250                 255
Ile Val His Ser Pro Thr Leu Met Met Leu Tyr Asn Asn Gln Ile Glu
            260                 265                 270
Ile Ala Ser Lys Asp Gln Trp Gln Ile Leu Phe Asn Cys Ile Leu Ala
        275                 280                 285
Ile Gly Ala Trp Cys Ile Glu Gly Glu Ser Thr Asp Ile Asp Val Phe
290                 295                 300
Tyr Tyr Gln Asn Ala Lys Ser His Leu Thr Ser Lys Val Phe Glu Ser
305                 310                 315                 320
Gly Ser Ile Ile Leu Val Thr Ala Leu His Leu Leu Ser Arg Tyr Thr
                325                 330                 335
Gln Trp Arg Gln Lys Thr Asn Thr Ser Tyr Asn Phe His Ser Phe Ser
            340                 345                 350
Ile Arg Met Ala Ile Ser Leu Gly Leu Asn Arg Asp Leu Pro Ser Ser
        355                 360                 365
Phe Ser Asp Ser Ser Ile Leu Glu Gln Arg Arg Ile Trp Trp Ser
370                 375                 380
Val Tyr Ser Trp Glu Ile Gln Leu Ser Leu Leu Tyr Gly Arg Ser Ile
385                 390                 395                 400
Gln Leu Ser Gln Asn Thr Ile Ser Phe Pro Ser Ser Val Asp Asp Val
                405                 410                 415
Gln Arg Thr Thr Thr Gly Pro Thr Ile Tyr His Gly Ile Ile Glu Thr
            420                 425                 430
Ala Arg Leu Leu Gln Val Phe Thr Lys Ile Tyr Glu Leu Asp Lys Thr
        435                 440                 445
Val Thr Ala Glu Lys Ser Pro Ile Cys Ala Lys Lys Cys Leu Met Ile
450                 455                 460
Cys Asn Glu Ile Glu Glu Val Ser Arg Gln Ala Pro Lys Phe Leu Gln
465                 470                 475                 480
Met Asp Ile Ser Thr Thr Ala Leu Thr Asn Leu Leu Lys Glu His Pro
                485                 490                 495
Trp Leu Ser Phe Thr Arg Phe Glu Leu Lys Trp Lys Gln Leu Ser Leu
            500                 505                 510
Ile Ile Tyr Val Leu Arg Asp Phe Phe Thr Asn Phe Thr Gln Lys Lys
        515                 520                 525
Ser Gln Leu Glu Gln Asp Gln Asn Asp His Gln Ser Tyr Glu Val Lys
    530                 535                 540
```

Arg Cys Ser Ile Met Leu Ser Asp Ala Ala Gln Arg Thr Val Met Ser
545                 550                 555                 560

Val Ser Ser Tyr Met Asp Asn His Asn Val Thr Pro Tyr Phe Ala Trp
            565                 570                 575

Asn Cys Ser Tyr Tyr Leu Phe Asn Ala Val Leu Val Pro Ile Lys Thr
            580                 585                 590

Leu Leu Ser Asn Ser Lys Ser Asn Ala Glu Asn Asn Glu Thr Ala Gln
            595                 600                 605

Leu Leu Gln Gln Ile Asn Thr Val Leu Met Leu Leu Lys Lys Leu Ala
610                 615                 620

Thr Phe Lys Ile Gln Thr Cys Glu Lys Tyr Ile Gln Val Leu Glu Glu
625                 630                 635                 640

Val Cys Ala Pro Phe Leu Leu Ser Gln Cys Ala Ile Pro Leu Pro His
            645                 650                 655

Ile Ser Tyr Asn Asn Ser Asn Gly Ser Ala Ile Lys Asn Ile Val Gly
            660                 665                 670

Ser Ala Thr Ile Ala Gln Tyr Pro Thr Leu Pro Glu Glu Asn Val Asn
            675                 680                 685

Asn Ile Ser Val Lys Tyr Val Ser Pro Gly Ser Val Gly Pro Ser Pro
690                 695                 700

Val Pro Leu Lys Ser Gly Ala Ser Phe Ser Asp Leu Val Lys Leu Leu
705                 710                 715                 720

Ser Asn Arg Pro Pro Ser Arg Asn Ser Pro Val Thr Ile Pro Arg Ser
            725                 730                 735

Thr Pro Ser His Arg Ser Val Thr Pro Phe Leu Gly Gln Gln Gln Gln
            740                 745                 750

Leu Gln Ser Leu Val Pro Leu Thr Pro Ser Ala Leu Phe Gly Gly Ala
            755                 760                 765

Asn Phe Asn Gln Ser Gly Asn Ile Ala Asp Ser Ser Leu Ser Phe Thr
            770                 775                 780

Phe Thr Asn Ser Ser Asn Gly Pro Asn Leu Ile Thr Thr Gln Thr Asn
785                 790                 795                 800

Ser Gln Ala Leu Ser Gln Pro Ile Ala Ser Ser Asn Val His Asp Asn
            805                 810                 815

Phe Met Asn Asn Glu Ile Thr Ala Ser Lys Ile Asp Asp Gly Asn Asn
            820                 825                 830

Ser Lys Pro Leu Ser Pro Gly Trp Thr Asp Gln Thr Ala Tyr Asn Ala
            835                 840                 845

Phe Gly Ile Thr Thr Gly Met Phe Asn Thr Thr Met Asp Asp Val
            850                 855                 860

Tyr Asn Tyr Leu Phe Asp Asp Glu Asp Thr Pro Pro Asn Pro Lys Lys
865                 870                 875                 880

Glu

<210> SEQ ID NO 56
<211> LENGTH: 13
<212> TYPE: PRT
<213> ORGANISM: Homo Sapiens

<400> SEQUENCE: 56

Pro Gln Lys Gly Ser Ala Ser Glu Lys Thr Met Val Phe
                5                   10

<210> SEQ ID NO 57
<211> LENGTH: 549
<212> TYPE: PRT

<213> ORGANISM: Homo sapiens

<400> SEQUENCE: 57

Met Asp Asp Leu Phe Pro Leu Ile Phe Pro Ser Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Tyr Tyr Glu Ala Asp Leu Cys Pro Asp Arg Ser Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe His Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ala Gly Arg Pro Leu Leu Leu Thr
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300

Thr Tyr Glu Thr Phe Lys Ser Ile Met Lys Lys Ser Pro Phe Asn Gly
305                 310                 315                 320

Pro Thr Glu Pro Arg Pro Pro Thr Arg Arg Ile Ala Val Pro Thr Arg
                325                 330                 335

Asn Ser Thr Ser Val Pro Lys Pro Ala Pro Gln Pro Tyr Thr Phe Pro
            340                 345                 350

Ala Ser Leu Ser Thr Ile Asn Phe Asp Glu Phe Ser Pro Met Leu Leu
        355                 360                 365

Pro Ser Gly Gln Ile Ser Asn Gln Ala Leu Ala Leu Ala Pro Ser Ser
    370                 375                 380

Ala Pro Val Leu Ala Gln Thr Met Val Pro Ser Ser Ala Met Val Pro
385                 390                 395                 400

Leu Ala Gln Pro Pro Ala Pro Ala Pro Val Leu Thr Pro Gly Pro Pro

```
                    405                 410                 415
Gln Ser Leu Ser Ala Pro Val Pro Lys Ser Thr Gln Ala Gly Glu Gly
                420                 425                 430

Thr Leu Ser Glu Ala Leu Leu His Leu Gln Phe Asp Ala Asp Glu Asp
            435                 440                 445

Leu Gly Ala Leu Leu Gly Asn Ser Thr Asp Pro Gly Val Phe Thr Asp
        450                 455                 460

Leu Ala Ser Val Asp Asn Ser Glu Phe Gln Gln Leu Leu Asn Gln Gly
465                 470                 475                 480

Val Ser Met Ser His Ser Thr Ala Glu Pro Met Leu Met Glu Tyr Pro
                485                 490                 495

Glu Ala Ile Thr Arg Leu Val Thr Gly Ser Gln Arg Pro Pro Asp Pro
                500                 505                 510

Ala Pro Thr Pro Leu Gly Thr Ser Gly Leu Pro Asn Gly Leu Ser Gly
            515                 520                 525

Asp Glu Asp Phe Ser Ser Ile Ala Asp Met Asp Phe Ser Ala Leu Leu
        530                 535                 540

Ser Gln Ile Ser Ser
545

<210> SEQ ID NO 58
<211> LENGTH: 1833
<212> TYPE: DNA
<213> ORGANISM: Homo sapiens

<400> SEQUENCE: 58
ggaggtggga ggagggagtg acgagtcaag gaggagacag ggacgcagga gggtgcaagg      60
aagtgtctta actgagacgg gggtaaggca agagagggtg gaggaaattc tgcaggagac     120
aggcttcctc cagggtctgg agaacccaga ggcagctcct cctgagtgct gggaaggact     180
ctgggcatct tcagcccttc ttactctctg aggctcaagc cagaaattca ggctgcttgc     240
agagtgggtg acagagccac ggagctggtg tccctgggac cctctgcccg tcttctctcc     300
actccccagc atggaggaag gtggtgattt tgacaactac tatggggcag acaaccagtc     360
tgagtgtgag tacacagact ggaaatcctc gggggccctc atccctgcca tctacatgtt     420
ggtcttcctc ctgggcacca cgggcaacgg tctggtgctc tggaccgtgt ttcggagcag     480
ccgggagaag aggcgctcag ctgatatctt cattgctagc ctggcggtgg ctgacctgac     540
cttcgtggtg acgctgcccc tgtgggctac ctacacgtac cgggactatg actggccctt     600
tgggaccttc ttctgcaagc tcagcagcta cctcatcttc gtcaacatgt acgccagcgt     660
cttctgcctc accggcctca gcttcgaccg ctacctggcc atcgtgaggc cagtggccaa     720
tgctcggctg aggctgcggg tcagcggggc cgtggccacg gcagttcttt gggtgctggc     780
cgccctcctg gccatgcctg tcatggtgtt acgcaccacc gggacttgg agaacaccac     840 taaggtgcag tgctacatgg actactccat ggtggccact gtgagctcag agtgggcctg     900
ggaggtgggc cttgggtct cgtccaccac cgtgggcttt gtggtgccct tcaccatcat     960
gctgacctgt tacttcttca tcgcccaaac catcgctggc cacttccgca aggaacgcat    1020
cgagggcctg cggaagcggc gccggctgct cagcatcatc gtggtgctgg tggtgacctt    1080
tgccctgtgc tggatgccct accacctggt gaagacgctg tacatgctgg gcagcctgct    1140
gcactggccc tgtgactttg acctcttcct catgaacatc ttccctact gcacctgcat    1200 cagctacgtc aacagctgcc tcaacccctt cctctatgcc tttttcgacc ccgcttccg    1260 ccaggcctgc acctccatgc tctgctgtgg ccagagcagg tgcgcaggca cctcccacag    1320
```

| | |
|---|---|
| cagcagtggg gagaagtcag ccagctactc ttcggggcac agccagggc cggccccaa | 1380 |
| catgggcaag ggtggagaac agatgcacga gaaatccatc ccctacagcc aggagaccct | 1440 |
| tgtggttgac tagggctggg agcagagaga agcctggcgc cctcggccct ccccggcctt | 1500 |
| tgcccttgct ttctgaaaat cagagtcacc tcctctgccc agagctgtcc tcaaagcatc | 1560 |
| cagtgaacac tggaagaggc ttctagaagg gaagaaattg tccctctgag gccgccgtgg | 1620 |
| gtgacctgca gagacttcct gcctggaact catctgtgaa ctgggacaga agcagaggag | 1680 |
| gctgcctgct gtgataccc cttacctccc ccagtgcctt cttcagaata tctgcactgt | 1740 |
| cttctgatcc tgttagtcac tgtggttcat caaataaaac tgtttgtgca actgttgtgt | 1800 |
| ccaaaaaaaa aaaaaaaaaa aaaaaaaaaa aaa | 1833 |

<210> SEQ ID NO 59
<211> LENGTH: 1666
<212> TYPE: DNA
<213> ORGANISM: Homo sapiens

<400> SEQUENCE: 59

| | |
|---|---|
| aactgcagcc agggagactc agactagaat ggaggtagaa agaactgatg cagagtgggt | 60 |
| ttaattctaa gccttttgt ggctaagttt tgttgttgtt aacttattga atttagagtt | 120 |
| gtattgcact ggtcatgtga aagccagagc agcaccagtg tcaaaatagt gacagagagt | 180 |
| tttgaatacc atagttagta tatatgtact cagagtattt ttattaaaga aggcaaagag | 240 |
| cccggcatag atcttatctt catcttcact cggttgcaaa atcaatagtt aagaaatagc | 300 |
| atctaaggga acttttaggt gggaaaaaaa atctagagat ggctctaaat gactgtttcc | 360 |
| ttctgaactt ggaggtggac catttcatgc actgcaacat ctccagtcac agtgcggatc | 420 |
| tccccgtgaa cgatgactgg tcccacccgg ggatcctcta tgtcatccct gcagtttatg | 480 |
| gggttatcat tctgataggc ctcattggca acatcacttt gatcaagatc ttctgtacag | 540 |
| tcaagtccat gcgaaacgtt ccaaacctgt tcatttccag tctggctttg ggagacctgc | 600 |
| tcctcctaat aacgtgtgct ccagtggatg ccagcaggta cctggctgac agatggctat | 660 |
| ttggcaggat tggctgcaaa ctgatcccct ttatacagct tacctctgtt ggggtgtctg | 720 |
| tcttcacact cacggcgctc tcggcagaca gatacaaagc cattgtccgg ccaatggata | 780 |
| tccaggcctc ccatgccctg atgaagatct gcctcaaagc cgcctttatc tggatcatct | 840 |
| ccatgctgct ggccattcca gaggccgtgt tttctgacct ccatcccttc catgaggaaa | 900 |
| gcaccaacca gaccttcatt agctgtgccc catacccaca ctctaatgag cttcaccca | 960 |
| aaatccattc tatggcttcc ttctggtct tctacgtcat cccactgtcg atcatctctg | 1020 |
| tttactacta cttcattgct aaaaatctga tccagagtgc ttacaatctt cccgtggaag | 1080 |
| ggaatataca tgtcaagaag cagattgaat cccggaagcg acttgccaag acagtgctgg | 1140 |
| tgtttgtggg cctgttcgcc ttctgctggc tcccaatca tgtcatctac ctgtaccgct | 1200 |
| cctaccacta ctctgaggtg gacacctcca tgctccactt tgtcaccagc atctgtgccc | 1260 |
| gcctcctggc cttcaccaac tcctgcgtga acccctttgc cctctacctg ctgagcaaga | 1320 |
| gtttcaggaa acagttcaac actcagctgc tctgttgcca gctggcctg atcatccggt | 1380 |
| ctcacagcac tggaaggagt acaacctgca tgacctccct caagagtacc aacccctccg | 1440 |
| tggccacctt tagcctcatc aatggaaaca tctgtcacga gcggtatgtc tagattgacc | 1500 |
| cttgatttg ccccctgagg gacgttttg ctttatggct agacaggaac ccttgcatcc | 1560 |
| attgttgtgt ctgtgccctc caaagagcct tcagaatgct cctgagtggt gtaggtgggg | 1620 |

```
gtggggaggc ccaaatgatg gatcaccatt atattttgaa agaagc              1666

<210> SEQ ID NO 60
<211> LENGTH: 2876
<212> TYPE: DNA
<213> ORGANISM: Homo sapiens

<400> SEQUENCE: 60
tgaaacctaa cccgccctgg ggaggcgcgc agcagaggct ccgattcggg gcaggtgaga     60
ggctgacttt ctctcggtgc gtccagtgga gctctgagtt tcgaatcggc ggcggcggat    120
tccccgcgcg cccggcgtcg gggcttccag gaggatgcgg agcccagcg cggcgtggct     180 gctgggggcc gccatcctgc tagcagcctc tctctcctgc agtggcacca tccaaggaac    240
caatagatcc tctaaaggaa gaagccttat tggtaaggtt gatggcacat cccacgtcac    300
tggaaaagga gttacagttg aaacagtctt ttctgtggat gagttttctg catctgtcct    360
cactggaaaa ctgaccactg tcttccttcc aattgtctac acaattgtgt tgtggtggg     420 tttgccaagt aacggcatgg ccctgtgggt cttttctttc cgaactaaga agaagcaccc    480
tgctgtgatt tacatggcca atctggcctt ggctgacctc ctctctgtca tctggttccc    540
cttgaagatt gcctatcaca tacatggcaa caactggatt tatggggaag ctctttgtaa    600
tgtgcttatt ggcttttttct atggcaacat gtactgttcc attctcttca tgacctgcct    660
cagtgtgcag aggtattggg tcatcgtgaa ccccatgggg cactccagga agaaggcaaa    720
cattgccatt ggcatctccc tggcaatatg gctgctgatt ctgctggtca ccatcccttt    780
gtatgtcgtg aagcagacca tcttcattcc tgccctgaac atcacgacct gtcatgatgt    840
tttgcctgag cagctcttgg tgggagacat gttcaattac ttcctctctc tggccattgg    900 ggtcttttctg ttcccagcct tcctcacagc ctctgcctat gtgctgatga tcagaatgct    960
gcgatcttct gccatggatg aaaactcaga gaagaaaagg aagagggcca tcaaactcat   1020
tgtcactgtc ctggccatgt acctgatctg cttcactcct agtaaccttc tgcttgtggt   1080
gcattatttt ctgattaaga gccagggcca gagccatgtc tatgccctgt acattgtagc   1140
cctctgcctc tctacccta acagctgcat cgacccctt gtctattact tgtttcaca     1200 tgatttcagg gatcatgcaa agaacgctct cctttgccga agtgtccgca ctgtaaagca   1260
gatgcaagta tccctcacct caaagaaaca ctccaggaaa tccagctctt actcttcaag   1320
ttcaaccact gttaagacct cctattgagt tttccaggtc ctcagatggg aattgcacag   1380
taggatgtgg aacctgtttta atgttatgag gacgtgtctg ttatttccta atcaaaaagg   1440
tctcaccaca taccatgtgg atgcagcacc tctcaggatt gctaggagct cccctgtttg   1500
catgagaaaa gtagtccccc aaattaacat cagtgtctgt ttcagaatct ctctactcag   1560
atgaccccag aaactgaacc aacagaagca gacttttcag aagatggtga agacagaaac   1620
ccagtaactt gcaaaaagta gacttggtgt gaagactcac ttctcagctg aaattatata   1680
tatacacata tatatatttt acatctggga tcatgataga cttgttaggg cttcaaggcc   1740
ctcagagatg atcagtccaa ctgaacgacc ttacaaatga ggaaaccaag ataaatgagc   1800
tgccagaatc aggtttccaa tcaacagcag tgagttggga ttggacagta gaatttcaat   1860
gtccagtgag tgaggttctt gtaccacttc atcaaaatca tggatcttgg ctgggtgcgg   1920
tgcctcatgc ctgtaatcct agcactttgg gaggctgagg caggcaatca cttgaggtca   1980
ggagttcgag accagcctgg ccatcatggc gaaacctcat ctctactaaa aatacaaaag   2040
ttaaccaggt gtgtggtgca cgtttgtaat cccagttact caggaggctg aggcacaaga   2100
```

```
attgagtatc actttaactc aggaggcaga ggttgcagtg agccgagatt gcaccactgc    2160
actccagctt gggtgataaa ataaaataaa atagtcgtga atcttgttca aaatgcagat    2220
tcctcagatt caataatgag agctcagact gggaacaggg cccaggaatc tgtgtggtac    2280
aaacctgcat ggtgtttatg cacacagaga tttgagaacc attgttctga atgctgcttc    2340
catttgacaa agtgccgtga taattttga aaagagaagc aaacaatggt gtctctttta    2400
tgttcagctt ataatgaaat ctgtttgttg acttattagg actttgaatt atttctttat    2460
taaccctctg agtttttgta tgtattatta ttaaagaaaa atgcaatcag gattttaaac    2520
atgtaaatac aaattttgta taacttttga tgacttcagt gaaattttca ggtagtctga    2580
gtaatagatt gttttgccac ttagaatagc atttgccact tagtatttta aaaaataatt    2640
gttggagtat ttattgtcag ttttgttcac ttgttatcta atacaaaatt ataaagcctt    2700
cagagggttt ggaccacatc tctttggaaa atagtttgca acatatttaa gagatacttg    2760
atgccaaaat gactttatac aacgattgta tttgtgactt ttaaaaataa ttatttatt    2820 gtgtaattga tttataaata acaaaatttt ttttacaact aaaaaaaaaa aaaaaa       2876

<210> SEQ ID NO 61
<211> LENGTH: 1668
<212> TYPE: DNA
<213> ORGANISM: Homo sapiens

<400> SEQUENCE: 61
gggagataac tcgtgctcac aggaagccac gcacccttga aaggcaccgg gtccttctta     60
gcatcgtgct tcctgagcaa gcctggcatt gcctcacaga ccttcctcag agccgctttc    120
agaaaagcaa gctgcttctg gttgggccca gacctgcctt gaggagcctg tagagttaaa    180
aaatgaaccc cacggatata gcagacacca ccctcgatga aagcatatac agcaattact    240
atctgtatga agtatccccc aagccttgca ccaaagaagg catcaaggca tttggggagc    300
tcttcctgcc cccactgtat tccttggttt ttgtatttgg tctgcttgga aattctgtgg    360
tggttctggt cctgttcaaa tacaagcggc tcaggtccat gactgatgtg tacctgctca    420
accttgccat ctcggatctg ctcttcgtgt tttccctccc tttttggggc tactatgcag    480
cagaccagtg ggtttttggg ctaggtctgt gcaagatgat ttcctggatg tacttggtgg    540
gcttttacag tggcatattc tttgtcatgc tcatgagcat tgatagatac ctggcaattg    600
tgcacgcggt gttttccttg agggcaagga ccttgactta tggggtcatc accagtttgg    660
ctacatggtc agtggctgtg ttcgcctccc ttcctggctt tctgttcagc acttgttata    720
ctgagcgcaa ccatacctac tgcaaaacca agtactctct caactccacg acgtggaagg    780
ttctcagctc cctggaaatc aacattctcg gattggtgat ccccttaggg atcatgctgt    840
tttgctactc catgatcatc aggaccttgc agcattgtaa aaatgagaag aagaacaagg    900
cggtgaagat gatctttgcc gtggtggtcc tcttccttgg gttctggaca ccttacaaca    960
tagtgctctt cctagagacc ctggtggagc tagaagtcct tcaggactgc acctttgaaa   1020
gatacttgga ctatgccatc caggccacag aaactctggc ttttgttcac tgctgcctta   1080
atcccatcat ctactttttt ctgggggaga atttcgcaa gtacatccta cagctcttca   1140
aaacctgcag gggcctttt gtgctctgcc aatactgtgg gctcctccaa atttactctg   1200
ctgacacccc cagctcatct tacacgcagt ccaccatgga tcatgatctt catgatgctc   1260
tgtagaaaaa tgaaatggtg aaatgcagag tcaatgaact ttccacattc agagcttact   1320
taaaattgta ttttggtaag agatccctga gccagtgtca ggaggaaggc ttacacccac   1380
```

```
agtggaaaga cagcttctca tcctgcaggc agcttttct ctcccactag acaagtccag    1440
cctggcaagg gttcacctgg gctgaggcat ccttcctcac accaggcttg cctgcaggca    1500
tgagtcagtc tgatgagaac tctgagcagt gcttgaatga agttgtaggt aatattgcaa    1560
ggcaaagact attcccttct aacctgaact gatgggtttc tccagaggga attgcagagt    1620
actggctgat ggagtaaatc gctacctttt gctgtggcaa atgggccc                 1668

<210> SEQ ID NO 62
<211> LENGTH: 1679
<212> TYPE: DNA
<213> ORGANISM: Homo sapiens

<400> SEQUENCE: 62
gtttgttggc tgcggcagca ggtagcaaag tgacgccgag ggcctgagtg ctccagtagc      60
caccgcatct ggagaaccag cggttaccat ggagggatc agtatataca cttcagataa     120
ctacaccgag gaaatgggct caggggacta tgactccatg aaggaaccct gtttccgtga     180
agaaaatgct aatttcaata aaatcttcct gcccaccatc tactccatca tcttcttaac     240
tggcattgtg gcaatggat tggtcatcct ggtcatgggt taccagaaga aactgagaag     300
catgacggac aagtacaggc tgcacctgtc agtggccgac ctcctctttg tcatcacgct     360
tcccttctgg gcagttgatg ccgtggcaaa ctggtacttt gggaacttcc tatgcaaggc     420
agtccatgtc atctacacag tcaacctcta cagcagtgtc ctcatcctgg ccttcatcag     480
tctggaccgc tacctggcca tcgtccacgc caccaacagt cagaggccaa ggaagctgtt     540
ggctgaaaag gtggtctatg ttggcgtctg gatccctgcc ctcctgctga ctattcccga     600
cttcatcttt gccaacgtca gtgaggcaga tgacagatat atctgtgacc gcttctaccc     660
caatgacttg tgggtggttg tgttccagtt tcagcacatc atggttggcc ttatcctgcc     720
tggtattgtc atcctgtcct gctattgcat tatcatctcc aagctgtcac actccaaggg     780
ccaccagaag cgcaaggccc tcaagaccac agtcatcctc atcctggctt tcttcgcctg     840
ttggctgcct tactacattg ggatcagcat cgactccttc atcctcctgg aaatcatcaa     900
gcaagggtgt gagtttgaga acactgtgca caagtggatt tccatcaccg aggccctagc     960
tttcttccac tgttgtctga cccccatcct ctatgctttc cttggagcca aatttaaaac    1020
ctctgcccag cacgcactca cctctgtgag cagagggtcc agcctcaaga tcctctccaa    1080
aggaaagcga ggtggacatt catctgtttc cactgagtct gagtcttcaa gttttcactc    1140
cagctaacac agatgtaaaa gactttttt tatacgataa ataactttt tttaagttac    1200 acattttca gatataaaag actgaccaat attgtacagt tttattgct tgttggattt     1260 ttgtcttgtg tttctttagt ttttgtgaag tttaattgac ttatttatat aaattttttt    1320
tgtttcatat tgatgtgtgt ctaggcagga cctgtggcca agttcttagt tgctgtatgt    1380
ctcgtggtag gactgtagaa aagggaactg aacattccag agcgtgtagt gaatcacgta    1440
aagctagaaa tgatcccag ctgtttatgc atagataatc tctccattcc cgtgaacgt    1500 ttttcctgtt cttaagacgt gattttgctg tagaagatgg cacttataac caaagcccaa    1560
agtggtatag aaatgctggt ttttcagttt tcaggagtgg gttgatttca gcacctacag    1620
tgtacagtct tgtattaagt tgttaataaa agtacatgtt aaacttactt agtgttatg      1679

<210> SEQ ID NO 63
<211> LENGTH: 2859
<212> TYPE: DNA
<213> ORGANISM: Homo sapiens
```

<400> SEQUENCE: 63

```
cattcagaga cagaaggtgg atagacaaat ctccaccttc agactggtag gctcctccag        60
aagccatcag acaggaagat gtgaaaatcc ccagcactca tcccagaatc actaagtggc       120
acctgtcctg ggccaaagtc ccaggacaga cctcattgtt cctctgtggg aatacctccc       180
caggagggca tcctggattt ccccccttgca cccaggtca gaagtttcat cgtcaaggtt       240
gtttcatctt ttttttcctg tctaacagct ctgactacca cccaaccttg aggcacagtg       300
aagacatcgg tggccactcc aataacagca ggtcacagct gctcttctgg aggtgtccta       360
caggtgaaaa gcccagcgac ccagtcagga tttaagttta cctcaaaaat ggaagatttt       420
aacatggaga gtgacagctt tgaagatttc tggaaaggtg aagatcttag taattacagt       480
tacagctcta ccctgccccc ttttctacta gatgccgccc catgtgaacc agaatccctg       540
gaaatcaaca agtattttgt ggtcattatc tatgccctgg tattcctgct gagcctgctg       600
ggaaactccc tcgtgatgct ggtcatctta tacagcaggt cggccgctc cgtcactgat        660
gtctacctgc tgaacctagc cttggccgac ctactctttg ccctgacctt gcccatctgg       720
gccgcctcca aggtgaatgg ctggattttt ggcacattcc tgtgcaaggt ggtctcactc       780
ctgaaggaag tcaacttcta tagtggcatc ctgctactgg cctgcatcag tgtggaccgt       840
tacctggcca ttgtccatgc cacacgcaca ctgacccaga gcgctactt ggtcaaattc        900
atatgtctca gcatctgggg tctgtccttg ctcctggccc tgcctgtctt acttttccga       960
aggaccgtct actcatccaa tgttagccca gcctgctatg aggacatggg caacaataca      1020
gcaaactggc ggatgctgtt acggatcctg ccccagtcct ttggcttcat cgtgccactg      1080
ctgatcatgc tgttctgcta cggattcacc ctgcgtacgc tgtttaaggc ccacatgggg      1140
cagaagcacc gggccatgcg ggtcatcttt gctgtcgtcc tcatcttcct gctctgctgg      1200
ctgcccctaca acctggtcct gctggcagac accctcatga ggacccaggt gatccaggag      1260
acctgtgagc gccgcaatca catcgaccgg gctctggatg ccaccgagat tctgggcatc      1320
cttcacagct gcctcaaccc cctcatctac gccttcattg ccagaagtt cgcatgga         1380
ctcctcaaga ttctagctat acatggcttg atcagcaagg actccctgcc caaagacagc      1440
aggccttcct tgttggctc ttcttcaggg cacacttcca ctactctcta agacctcctg       1500
cctaagtgca gccccgtggg gttcctccct tctcttcaca gtcacattcc aagcctcatg      1560
tccactggtt cttcttggtc tcagtgtcaa tgcagccccc attgtggtca caggaagtag      1620
aggaggccac gttcttacta gttcccttg catggtttag aaagcttgcc ctggtgcctc       1680
accccttgcc ataattacta tgtcatttgc tggagctctg cccatcctgc ccctgagccc      1740
atggcactct atgttctaag aagtgaaaat ctacactcca gtgagacagc tctgcatact      1800
cattaggatg gctagtatca aaagaaagaa aatcaggctg gccaacgggg tgaaaccctg      1860
tctctactaa aaatacaaaa aaaaaaaaaa attagccggg cgtggtggtg agtgcctgta      1920
atcacagcta cttgggaggc tgagatggga gaatcacttg aacccgggag gcagaggttg      1980
cagtgagccg agattgtgcc cctgcactcc agcctgagcg acagtgagac tctgtctcag      2040
tccatgaaga tgtagaggag aaactggaac tctcgagcgt tgctgggggg gattgtaaaa      2100
tggtgtgacc actgcagaag acagtatggc agctttcctc aaaacttcag acatagaatt      2160
aacacatgat cctgcaattc cacttatagg aattgaccca caagaaatga agcagggac       2220
ttgaacccat atttgtacac caatattcat agcagcttat tcacaagacc caaaaggcag     2280
aagcaaccca atgttcatc aatgaatgaa tgaatggcta agcaaaatgt gatatgtacc       2340
```

-continued

```
taacgaagta tccttcagcc tgaaagagga atgaagtact catacatgtt acaacacgga    2400
cgaaccttga aactttatg ctaagtgaaa taagccagac atcaacagat aaatagttta     2460
tgattccacc tacatgaggt actgagagtg aacaaattta cagagacaga aagcagaaca    2520
gtgattacca gggactgagg ggaggggagc atgggaagtg acggtttaat gggcacaggg    2580
tttatgttta ggatgttgaa aaagttctgc agataaacag tagtgatagt tgtaccgcaa    2640
tgtgacttaa tgccactaaa ttgacactta aaaatggttt aaatggtcaa ttttgttatg    2700 tatatttat  atcaatttaa aaaaaaacct gagccccaaa aggtatttta atcaccaagg    2760
ctgattaaac caaggctaga accacctgcc tatattttt  gttaaatgat ttcattcaat    2820
atcttttttt taataaacca tttttacttg ggtgtttat                           2859
```

<210> SEQ ID NO 64
<211> LENGTH: 27
<212> TYPE: DNA
<213> ORGANISM: Homo Sapiens

<400> SEQUENCE: 64

```
tgtgcgcgcg gccagagcag gtgcgca                                           27
```

<210> SEQ ID NO 65
<211> LENGTH: 26
<212> TYPE: DNA
<213> ORGANISM: Homo Sapiens

<400> SEQUENCE: 65

```
gaggatccgt caaccacaag ggtctc                                            26
```

<210> SEQ ID NO 66
<211> LENGTH: 27
<212> TYPE: DNA
<213> ORGANISM: Homo Sapiens

<400> SEQUENCE: 66

```
tgtgcgcgcg gcctgatcat ccggtct                                           27
```

<210> SEQ ID NO 67
<211> LENGTH: 26
<212> TYPE: DNA
<213> ORGANISM: Homo Sapiens

<400> SEQUENCE: 67

```
gaggatccga cataccgctc gtgaca                                            26
```

<210> SEQ ID NO 68
<211> LENGTH: 28
<212> TYPE: DNA
<213> ORGANISM: Homo Sapiens

<400> SEQUENCE: 68

```
tgtgcgcgca gtgtccgcac tgtaaagc                                          28
```

<210> SEQ ID NO 69
<211> LENGTH: 26
<212> TYPE: DNA
<213> ORGANISM: Homo Sapiens

<400> SEQUENCE: 69

```
gaggatccat aggaggtctt aacagt                                            26
```

-continued

```
<210> SEQ ID NO 70
<211> LENGTH: 27
<212> TYPE: DNA
<213> ORGANISM: Homo Sapiens

<400> SEQUENCE: 70
tgtgcgcgcg gccttttgt gctctgc                                         27

<210> SEQ ID NO 71
<211> LENGTH: 26
<212> TYPE: DNA
<213> ORGANISM: Homo Sapiens

<400> SEQUENCE: 71
gaggatccca gagcatcatg aagatc                                          26

<210> SEQ ID NO 72
<211> LENGTH: 28
<212> TYPE: DNA
<213> ORGANISM: Homo Sapiens

<400> SEQUENCE: 72
tgtgcgcgcg gcttgatcag caagggac                                        28

<210> SEQ ID NO 73
<211> LENGTH: 26
<212> TYPE: DNA
<213> ORGANISM: Homo Sapiens

<400> SEQUENCE: 73
gaggatccga gagtagtgga agtgtg                                          26

<210> SEQ ID NO 74
<211> LENGTH: 27
<212> TYPE: DNA
<213> ORGANISM: Homo Sapiens

<400> SEQUENCE: 74
tgtgcgcgcg ggtccagcct caagatc                                         27

<210> SEQ ID NO 75
<211> LENGTH: 26
<212> TYPE: DNA
<213> ORGANISM: Homo Sapiens

<400> SEQUENCE: 75
gaggatccgc tggagtgaaa acttga                                          26

<210> SEQ ID NO 76
<211> LENGTH: 5616
<212> TYPE: DNA
<213> ORGANISM: Homo Sapiens

<400> SEQUENCE: 76
ccccggcgca gcgcggccgc agcagcctcc gcccccgca cggtgtgagc gcccgacgcg      60
gccgaggcgg ccggagtccc gagctagccc cggcggccgc cgccgcccag accggacgac    120
aggccacctc gtcggcgtcc gcccgagtcc ccgcctcgcc gccaacgcca caaccaccgc    180
gcacggcccc ctgactccgt ccagtattga tcggagagc cggagcgagc tcttcgggga    240
gcagcgatgc gaccctccgg gacggccggg gcagcgctcc tggcgctgct ggctgcgctc    300
tgcccggcga gtcgggctct ggaggaaaag aaagtttgcc aaggcacgag taacaagctc    360
acgcagttgg gcacttttga agatcatttt ctcagcctcc agaggatgtt caataactgt    420
```

```
gaggtggtcc ttgggaattt ggaaattacc tatgtgcaga ggaattatga tctttccttc    480
ttaaagacca tccaggaggt ggctggttat gtcctcattg ccctcaacac agtggagcga    540
attcctttgg aaaacctgca gatcatcaga ggaaatatgt actacgaaaa ttcctatgcc    600
ttagcagtct tatctaacta tgatgcaaat aaaaccggac tgaaggagct gcccatgaga    660
aatttacagg aaatcctgca tggcgccgtg cggttcagca acaaccctgc cctgtgcaac    720
gtggagagca tccagtggcg ggacatagtc agcagtgact ttctcagcaa catgtcgatg    780
gacttccaga accacctggg cagctgccaa aagtgtgatc caagctgtcc caatgggagc    840
tgctggggtg caggagagga gaactgccag aaactgacca aaatcatctg tgcccagcag    900
tgctccgggc gctgccgtgg caagtccccc agtgactgct gccacaacca gtgtgctgca    960
ggctgcacag gcccccggga gagcgactgc ctggtctgcc gcaaattccg agacgaagcc   1020
acgtgcaagg acacctgccc cccactcatg ctctacaacc ccaccacgta ccagatggat   1080
gtgaaccccg agggcaaata cagctttggt gccacctgcg tgaagaagtg tccccgtaat   1140
tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca cagggttttt gctgattcag gcttggcctg aaaacaggac ggacctccat   1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga aatttcagg aaacaaaaat ttgtgctatg caaatacaat aaactggaaa   1680
aaactgtttg ggacctccgg tcagaaaacc aaaattataa gcaacagagg tgaaaacagc   1740
tgcaaggcca caggccaggt ctgccatgcc ttgtgctccc ccgagggctg ctggggcccg   1800
gagcccaggg actgcgtctc ttgccggaat gtcagccgag gcagggaatg cgtggacaag   1860
tgcaaccttc tggagggtga gccaagggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag tcttgaagg ctgtccaacg   2160 aatgggccta agatcccgtc catcgccact gggatggtgg gggccctcct cttgctgctg   2220
gtggtggccc tgggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag ggactctgga tcccagaagg tgagaaagtt   2460
aaaattcccg tcgctatcaa ggaattaaga gaagcaacat ctcgaaagc caacaaggaa   2520 atcctcgatg aagcctacgt gatggccagc gtggacaacc cccacgtgtg ccgcctgctg   2580
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatca aagggcat gaactacttg gaggaccgtc gcttggtgca ccgcgacctg   2760
gcagccagga acgtactggt gaaaacaccg cagcatgtca agatcacaga ttttgggctg   2820
```

```
gccaaactgc tgggtgcgga agagaaagaa taccatgcag aaggaggcaa agtgcctatc    2880
aagtggatgg cattggaatc aattttacac agaatctata cccaccagag tgatgtctgg    2940
agctacgggg tgaccgtttg ggagttgatg acctttggat ccaagccata tgacggaatc    3000
cctgccagcg agatctcctc catcctggag aaaggagaac gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc aggggatga agaatgcat ttgccaagtc ctacagactc caacttctac    3240
cgtgccctga tggatgaaga agacatggac gacgtggtgg atgccgacga gtacctcatc    3300
ccacagcagg gcttcttcag cagcccctcc acgtcacgga ctcccctcct gagctctctg    3360
agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcgaga cccacacta ccaggacccc cacagcactg cagtgggcaa ccccgagtat    3660
ctcaacactg tccagcccac ctgtgtcaac agcacattcg acagccctgc ccactgggcc    3720
cagaaaggca gccaccaaat tagcctggac aaccctgact accagcagga cttctttccc    3780
aaggaagcca agccaaatgg catctttaag ggctccacag ctgaaaatgc agaataccta    3840
agggtcgcgc cacaaagcag tgaatttatt ggagcatgac cacggaggat agtatgagcc    3900
ctaaaaatcc agactctttc gatacccagg accaagccac agcaggtcct ccatcccaac    3960
agccatgccc gcattagctc ttagacccac agactggttt tgcaacgttt acaccgacta    4020
gccaggaagt acttccacct cgggcacatt ttgggaagtt gcattccttt gtcttcaaac    4080
tgtgaagcat ttacagaaac gcatccagca agaatattgt ccctttgagc agaaatttat    4140 cttcaaga ggtatatttg aaaaaaaaaa aaagtatatg tgaggatttt tattgattgg    4200
ggatcttgga gttttcatt gtcgctattg attttactt caatgggctc ttccaacaag    4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
agaaacggag gggatggaat tcttccttag acttactttt gtaaaaatgt ccccacggta    4560
cttactcccc actgatggac cagtggtttc cagtcatgag cgttagactg acttgtttgt    4620
cttccattcc attgttttga aactcagtat gctgccctg tcttgctgtc atgaaatcag    4680
caagagagga tgcacatca ataataact cggattccag cccacattgg attcatcagc    4740
atttggacca atagcccaca gctgagaatg tggaatacct aaggatagca ccgcttttgt    4800
tctcgcaaaa acgtatctcc taatttgagg ctcagatgaa atgcatcagg tcctttgggg    4860
catagatcag aagactacaa aaatgaagct gctctgaaat ctcctttagc catcacccca    4920
accccccaaa attagtttgt gttacttatg aagatagtt ttctccttt acttcacttc    4980 aaaagctttt tactcaaaga gtatatgttc cctccaggtc agctgccccc aaaccccctc    5040
cttacgcttt gtcacacaaa aagtgtctct gccttgagtc atctattcaa gcacttacag    5100
ctctggccac aacagggcat tttacaggtg cgaatgacag tagcattatg agtagtgtgg    5160
aattcaggta gtaaatatga aactagggtt tgaaattgat aatgctttca caacatttgc    5220
```

```
agatgtttta gaaggaaaaa agttccttcc taaaataatt tctctacaat tggaagattg    5280
gaagattcag ctagttagga gcccaccttt tttcctaatc tgtgtgtgcc ctgtaacctg    5340
actggttaac agcagtcctt tgtaaacagt gttttaaact ctcctagtca atatccaccc    5400
catccaattt atcaaggaag aaatggttca gaaatatttt tcagcctaca gttatgttca    5460
gtcacacaca catacaaaat gttccttttg cttttaaagt aattttttgac tcccagatca    5520 gtcagagccc ctacagcatt gttaagaaag tatttgattt ttgtctcaat gaaaataaaa    5580
ctatattcat ttccactcta aaaaaaaaaa aaaaaa                              5616
```

<210> SEQ ID NO 77
<211> LENGTH: 12
<212> TYPE: PRT
<213> ORGANISM: Homo Sapiens

<400> SEQUENCE: 77

Gly Gly Ser Gly Ser Glu Asn Leu Tyr Phe Gln Leu
              5                   10

<210> SEQ ID NO 78
<211> LENGTH: 1291
<212> TYPE: PRT
<213> ORGANISM: Homo sapiens

<400> SEQUENCE: 78

Met Ala Gly Ala Ala Ser Pro Cys Ala Asn Gly Cys Gly Pro Gly Ala
              5                   10                  15

Pro Ser Asp Ala Glu Val Leu His Leu Cys Arg Ser Leu Glu Val Gly
         20                  25                  30

Thr Val Met Thr Leu Phe Tyr Ser Lys Lys Ser Gln Arg Pro Glu Arg
     35                  40                  45

Lys Thr Phe Gln Val Lys Leu Glu Thr Arg Gln Ile Thr Trp Ser Arg
 50                  55                  60

Gly Ala Asp Lys Ile Glu Gly Ala Ile Asp Ile Arg Glu Ile Lys Glu
 65                  70                  75                  80

Ile Arg Pro Gly Lys Thr Ser Arg Asp Phe Asp Arg Tyr Gln Glu Asp
                 85                  90                  95

Pro Ala Phe Arg Pro Asp Gln Ser His Cys Phe Val Ile Leu Tyr Gly
            100                 105                 110

Met Glu Phe Arg Leu Lys Thr Leu Ser Leu Gln Ala Thr Ser Glu Asp
        115                 120                 125

Glu Val Asn Met Trp Ile Lys Gly Leu Thr Trp Leu Met Glu Asp Thr
    130                 135                 140

Leu Gln Ala Pro Thr Pro Leu Gln Ile Glu Arg Trp Leu Arg Lys Gln
145                 150                 155                 160

Phe Tyr Ser Val Asp Arg Asn Arg Glu Asp Arg Ile Ser Ala Lys Asp
                165                 170                 175

Leu Lys Asn Met Leu Ser Gln Val Asn Tyr Arg Val Pro Asn Met Arg
            180                 185                 190

Phe Leu Arg Glu Arg Leu Thr Asp Leu Glu Gln Arg Ser Gly Asp Ile
        195                 200                 205

Thr Tyr Gly Gln Phe Ala Gln Leu Tyr Arg Ser Leu Met Tyr Ser Ala
    210                 215                 220

Gln Lys Thr Met Asp Leu Pro Phe Leu Glu Ala Ser Thr Leu Arg Ala
225                 230                 235                 240

Gly Glu Arg Pro Glu Leu Cys Arg Val Ser Leu Pro Glu Phe Gln Gln

```
                245                 250                 255
Phe Leu Leu Asp Tyr Gln Gly Glu Leu Trp Ala Val Asp Arg Leu Gln
                260                 265                 270

Val Gln Glu Phe Met Leu Ser Phe Leu Arg Asp Pro Leu Arg Glu Ile
                275                 280                 285

Glu Glu Pro Tyr Phe Phe Leu Asp Glu Phe Val Thr Phe Leu Phe Ser
                290                 295                 300

Lys Glu Asn Ser Val Trp Asn Ser Gln Leu Asp Ala Val Cys Pro Asp
305                 310                 315                 320

Thr Met Asn Asn Pro Leu Ser His Tyr Trp Ile Ser Ser His Asn
                325                 330                 335

Thr Tyr Leu Thr Gly Asp Gln Phe Ser Ser Glu Ser Ser Leu Glu Ala
                340                 345                 350

Tyr Ala Arg Cys Leu Arg Met Gly Cys Arg Cys Ile Glu Leu Asp Cys
                355                 360                 365

Trp Asp Gly Pro Asp Gly Met Pro Val Ile Tyr His Gly His Thr Leu
                370                 375                 380

Thr Thr Lys Ile Lys Phe Ser Asp Val Leu His Thr Ile Lys Glu His
385                 390                 395                 400

Ala Phe Val Ala Ser Glu Tyr Pro Val Ile Leu Ser Ile Glu Asp His
                405                 410                 415

Cys Ser Ile Ala Gln Gln Arg Asn Met Ala Gln Tyr Phe Lys Lys Val
                420                 425                 430

Leu Gly Asp Thr Leu Leu Thr Lys Pro Val Glu Ile Ser Ala Asp Gly
                435                 440                 445

Leu Pro Ser Pro Asn Gln Leu Lys Arg Lys Ile Leu Ile Lys His Lys
                450                 455                 460

Lys Leu Ala Glu Gly Ser Ala Tyr Glu Glu Val Pro Thr Ser Met Met
465                 470                 475                 480

Tyr Ser Glu Asn Asp Ile Ser Asn Ser Ile Lys Asn Gly Ile Leu Tyr
                485                 490                 495

Leu Glu Asp Pro Val Asn His Glu Trp Tyr Pro His Tyr Phe Val Leu
                500                 505                 510

Thr Ser Ser Lys Ile Tyr Tyr Ser Glu Glu Thr Ser Ser Asp Gln Gly
                515                 520                 525

Asn Glu Asp Glu Glu Pro Lys Glu Val Ser Ser Ser Thr Glu Leu
530                 535                 540

His Ser Asn Glu Lys Trp Phe His Gly Lys Leu Gly Ala Gly Arg Asp
545                 550                 555                 560

Gly Arg His Ile Ala Glu Arg Leu Leu Thr Glu Tyr Cys Ile Glu Thr
                565                 570                 575

Gly Ala Pro Asp Gly Ser Phe Leu Val Arg Glu Ser Glu Thr Phe Val
                580                 585                 590

Gly Asp Tyr Thr Leu Ser Phe Trp Arg Asn Gly Lys Val Gln His Cys
                595                 600                 605

Arg Ile His Ser Arg Gln Asp Ala Gly Thr Pro Lys Phe Phe Leu Thr
                610                 615                 620

Asp Asn Leu Val Phe Asp Ser Leu Tyr Asp Leu Ile Thr His Tyr Gln
625                 630                 635                 640

Gln Val Pro Leu Arg Cys Asn Glu Phe Glu Met Arg Leu Ser Glu Pro
                645                 650                 655

Val Pro Gln Thr Asn Ala His Glu Ser Lys Glu Trp Tyr His Ala Ser
                660                 665                 670
```

```
Leu Thr Arg Ala Gln Ala Glu His Met Leu Met Arg Val Pro Arg Asp
            675                 680                 685
Gly Ala Phe Leu Val Arg Lys Arg Asn Glu Pro Asn Ser Tyr Ala Ile
        690                 695                 700
Ser Phe Arg Ala Glu Gly Lys Ile Lys His Cys Arg Val Gln Gln Glu
705                 710                 715                 720
Gly Gln Thr Val Met Leu Gly Asn Ser Glu Phe Asp Ser Leu Val Asp
                725                 730                 735
Leu Ile Ser Tyr Tyr Glu Lys His Pro Leu Tyr Arg Lys Met Lys Leu
            740                 745                 750
Arg Tyr Pro Ile Asn Glu Glu Ala Leu Glu Lys Ile Gly Thr Ala Glu
        755                 760                 765
Pro Asp Tyr Gly Ala Leu Tyr Glu Gly Arg Asn Pro Gly Phe Tyr Val
    770                 775                 780
Glu Ala Asn Pro Met Pro Thr Phe Lys Cys Ala Val Lys Ala Leu Phe
785                 790                 795                 800
Asp Tyr Lys Ala Gln Arg Glu Asp Glu Leu Thr Phe Ile Lys Ser Ala
                805                 810                 815
Ile Ile Gln Asn Val Glu Lys Gln Glu Gly Gly Trp Trp Arg Gly Asp
            820                 825                 830
Tyr Gly Gly Lys Lys Gln Leu Trp Phe Pro Ser Asn Tyr Val Glu Glu
        835                 840                 845
Met Val Asn Pro Val Ala Leu Glu Pro Glu Arg Glu His Leu Asp Glu
    850                 855                 860
Asn Ser Pro Leu Gly Asp Leu Leu Arg Gly Val Leu Asp Val Pro Ala
865                 870                 875                 880
Cys Gln Ile Ala Ile Arg Pro Glu Gly Lys Asn Asn Arg Leu Phe Val
                885                 890                 895
Phe Ser Ile Ser Met Ala Ser Val Ala His Trp Ser Leu Asp Val Ala
            900                 905                 910
Ala Asp Ser Gln Glu Glu Leu Gln Asp Trp Val Lys Lys Ile Arg Glu
        915                 920                 925
Val Ala Gln Thr Ala Asp Ala Arg Leu Thr Glu Gly Lys Ile Met Glu
    930                 935                 940
Arg Arg Lys Lys Ile Ala Leu Glu Leu Ser Glu Leu Val Val Tyr Cys
945                 950                 955                 960
Arg Pro Val Pro Phe Asp Glu Glu Lys Ile Gly Thr Glu Arg Ala Cys
                965                 970                 975
Tyr Arg Asp Met Ser Ser Phe Pro Glu Thr Lys Ala Glu Lys Tyr Val
            980                 985                 990
Asn Lys Ala Lys Gly Lys Lys Phe Leu Gln Tyr Asn Arg Leu Gln Leu
        995                 1000                1005
Ser Arg Ile Tyr Pro Lys Gly Gln Arg Leu Asp Ser Ser Asn Tyr Asp
    1010                1015                1020
Pro Leu Pro Met Trp Ile Cys Gly Ser Gln Leu Val Ala Leu Asn Phe
1025                1030                1035                1040
Gln Thr Pro Asp Lys Pro Met Gln Met Asn Gln Ala Leu Phe Met Thr
                1045                1050                1055
Gly Arg His Cys Gly Tyr Val Leu Gln Pro Ser Thr Met Arg Asp Glu
            1060                1065                1070
Ala Phe Asp Pro Phe Asp Lys Ser Ser Leu Arg Gly Leu Glu Pro Cys
        1075                1080                1085
Ala Ile Ser Ile Glu Val Leu Gly Ala Arg His Leu Pro Lys Asn Gly
    1090                1095                1100
```

```
Arg Gly Ile Val Cys Pro Phe Val Glu Ile Glu Val Ala Gly Ala Glu
1105                1110                1115                1120

Tyr Asp Ser Thr Lys Gln Lys Thr Glu Phe Val Val Asp Asn Gly Leu
            1125                1130                1135

Asn Pro Val Trp Pro Ala Lys Pro Phe His Phe Gln Ile Ser Asn Pro
            1140                1145                1150

Glu Phe Ala Phe Leu Arg Phe Val Val Tyr Glu Glu Asp Met Phe Ser
            1155                1160                1165

Asp Gln Asn Phe Leu Ala Gln Ala Thr Phe Pro Val Lys Gly Leu Lys
            1170                1175                1180

Thr Gly Tyr Arg Ala Val Pro Leu Lys Asn Asn Tyr Ser Glu Asp Leu
1185                1190                1195                1200

Glu Leu Ala Ser Leu Leu Ile Lys Ile Asp Ile Phe Pro Ala Lys Gln
            1205                1210                1215

Glu Asn Gly Asp Leu Ser Pro Phe Ser Gly Thr Ser Leu Arg Glu Arg
            1220                1225                1230

Gly Ser Asp Ala Ser Gly Gln Leu Phe His Gly Arg Ala Arg Glu Gly
            1235                1240                1245

Ser Phe Glu Ser Arg Tyr Gln Gln Pro Phe Glu Asp Phe Arg Ile Ser
            1250                1255                1260

Gln Glu His Leu Ala Asp His Phe Asp Ser Arg Glu Arg Arg Ala Pro
1265                1270                1275                1280

Arg Arg Thr Arg Val Asn Gly Asp Asn Arg Leu
            1285                1290

<210> SEQ ID NO 79
<211> LENGTH: 3054
<212> TYPE: PRT
<213> ORGANISM: Homo sapiens

<400> SEQUENCE: 79

Met Ala Leu Ile Phe Gly Thr Val Asn Ala Asn Ile Leu Lys Glu Val
                5                   10                  15

Phe Gly Gly Ala Arg Met Ala Cys Val Thr Ser Ala His Met Ala Gly
            20                  25                  30

Ala Asn Gly Ser Ile Leu Lys Lys Ala Glu Glu Thr Ser Arg Ala Ile
        35                  40                  45

Met His Lys Pro Val Ile Phe Gly Glu Asp Tyr Ile Thr Glu Ala Asp
    50                  55                  60

Leu Pro Tyr Thr Pro Leu His Leu Glu Val Asp Ala Glu Met Glu Arg
65                  70                  75                  80

Met Tyr Tyr Leu Gly Arg Arg Ala Leu Thr His Gly Lys Arg Arg Lys
                85                  90                  95

Val Ser Val Asn Asn Lys Arg Asn Arg Arg Lys Val Ala Lys Thr
            100                 105                 110

Tyr Val Gly Arg Asp Ser Ile Val Glu Lys Ile Val Val Pro His Thr
        115                 120                 125

Glu Arg Lys Val Asp Thr Thr Ala Ala Val Glu Asp Ile Cys Asn Glu
    130                 135                 140

Ala Thr Thr Gln Leu Val His Asn Ser Met Pro Lys Arg Lys Lys Gln
145                 150                 155                 160

Lys Asn Phe Leu Pro Ala Thr Ser Leu Ser Asn Val Tyr Ala Gln Thr
                165                 170                 175

Trp Ser Ile Val Arg Lys Arg His Met Gln Val Glu Ile Ile Ser Lys
            180                 185                 190
```

```
Lys Ser Val Arg Ala Arg Val Lys Arg Phe Glu Gly Ser Val Gln Leu
        195                 200                 205

Phe Ala Ser Val Arg His Met Tyr Gly Glu Arg Lys Arg Val Asp Leu
        210                 215                 220

Arg Ile Asp Asn Trp Gln Gln Glu Thr Leu Leu Asp Leu Ala Lys Arg
225                 230                 235                 240

Phe Lys Asn Glu Arg Val Asp Gln Ser Lys Leu Thr Phe Gly Ser Ser
                245                 250                 255

Gly Leu Val Leu Arg Gln Gly Ser Tyr Gly Pro Ala His Trp Tyr Arg
                260                 265                 270

His Gly Met Phe Ile Val Arg Gly Arg Ser Asp Gly Met Leu Val Asp
        275                 280                 285

Ala Arg Ala Lys Val Thr Phe Ala Val Cys His Ser Met Thr His Tyr
        290                 295                 300

Ser Asp Lys Ser Ile Ser Glu Ala Phe Phe Ile Pro Tyr Ser Lys Lys
305                 310                 315                 320

Phe Leu Glu Leu Arg Pro Asp Gly Ile Ser His Glu Cys Thr Arg Gly
                325                 330                 335

Val Ser Val Glu Arg Cys Gly Glu Val Ala Ala Ile Leu Thr Gln Ala
                340                 345                 350

Leu Ser Pro Cys Gly Lys Ile Thr Cys Lys Arg Cys Met Val Glu Thr
        355                 360                 365

Pro Asp Ile Val Glu Gly Glu Ser Gly Glu Ser Val Thr Asn Gln Gly
        370                 375                 380

Lys Leu Leu Ala Met Leu Lys Glu Gln Tyr Pro Asp Phe Pro Met Ala
385                 390                 395                 400

Glu Lys Leu Leu Thr Arg Phe Leu Gln Gln Lys Ser Leu Val Asn Thr
                405                 410                 415

Asn Leu Thr Ala Cys Val Ser Val Lys Gln Leu Ile Gly Asp Arg Lys
                420                 425                 430

Gln Ala Pro Phe Thr His Val Leu Ala Val Ser Glu Ile Leu Phe Lys
        435                 440                 445

Gly Asn Lys Leu Thr Gly Ala Asp Leu Glu Glu Ala Ser Thr His Met
        450                 455                 460

Leu Glu Ile Ala Arg Phe Leu Asn Asn Arg Thr Glu Asn Met Arg Ile
465                 470                 475                 480

Gly His Leu Gly Ser Phe Arg Asn Lys Ile Ser Ser Lys Ala His Val
                485                 490                 495

Asn Asn Ala Leu Met Cys Asp Asn Gln Leu Asp Gln Asn Gly Asn Phe
                500                 505                 510

Ile Trp Gly Leu Arg Gly Ala His Ala Lys Arg Phe Leu Lys Gly Phe
        515                 520                 525

Phe Thr Glu Ile Asp Pro Asn Glu Gly Tyr Asp Lys Tyr Val Ile Arg
        530                 535                 540

Lys His Ile Arg Gly Ser Arg Lys Leu Ala Ile Gly Asn Leu Ile Met
545                 550                 555                 560

Ser Thr Asp Phe Gln Thr Leu Arg Gln Gln Ile Gln Gly Glu Thr Ile
                565                 570                 575

Glu Arg Lys Glu Ile Gly Asn His Cys Ile Ser Met Arg Asn Gly Asn
                580                 585                 590

Tyr Val Tyr Pro Cys Cys Cys Val Thr Leu Glu Asp Gly Lys Ala Gln
                595                 600                 605

Tyr Ser Asp Leu Lys His Pro Thr Lys Arg His Leu Val Ile Gly Asn
```

```
              610                 615                 620
Ser Gly Asp Ser Lys Tyr Leu Asp Leu Pro Val Leu Asn Glu Glu Lys
625                 630                 635                 640

Met Tyr Ile Ala Asn Glu Gly Tyr Cys Tyr Met Asn Ile Phe Phe Ala
                    645                 650                 655

Leu Leu Val Asn Val Lys Glu Glu Asp Ala Lys Asp Phe Thr Lys Phe
                660                 665                 670

Ile Arg Asp Thr Ile Val Pro Lys Leu Gly Ala Trp Pro Thr Met Gln
            675                 680                 685

Asp Val Ala Thr Ala Cys Tyr Leu Leu Ser Ile Leu Tyr Pro Asp Val
690                 695                 700

Leu Arg Ala Glu Leu Pro Arg Ile Leu Val Asp His Asp Asn Lys Thr
705                 710                 715                 720

Met His Val Leu Asp Ser Tyr Gly Ser Arg Thr Thr Gly Tyr His Met
                725                 730                 735

Leu Lys Met Asn Thr Thr Ser Gln Leu Ile Glu Phe Val His Ser Gly
                740                 745                 750

Leu Glu Ser Glu Met Lys Thr Tyr Asn Val Gly Gly Met Asn Arg Asp
                755                 760                 765

Val Val Thr Gln Gly Ala Ile Glu Met Leu Ile Lys Ser Ile Tyr Lys
770                 775                 780

Pro His Leu Met Lys Gln Leu Leu Glu Glu Pro Tyr Ile Ile Val
785                 790                 795                 800

Leu Ala Ile Val Ser Pro Ser Ile Leu Ile Ala Met Tyr Asn Ser Gly
                805                 810                 815

Thr Phe Glu Gln Ala Leu Gln Met Trp Leu Pro Asn Thr Met Arg Leu
                820                 825                 830

Ala Asn Leu Ala Ala Ile Leu Ser Ala Leu Ala Gln Lys Leu Thr Leu
                835                 840                 845

Ala Asp Leu Phe Val Gln Gln Arg Asn Leu Ile Asn Glu Tyr Ala Gln
                850                 855                 860

Val Ile Leu Asp Asn Leu Ile Asp Gly Val Arg Val Asn His Ser Leu
865                 870                 875                 880

Ser Leu Ala Met Glu Ile Val Thr Ile Lys Leu Ala Thr Gln Glu Met
                885                 890                 895

Asp Met Ala Leu Arg Glu Gly Gly Tyr Ala Val Thr Ser Glu Lys Val
                900                 905                 910

His Glu Met Leu Glu Lys Asn Tyr Val Lys Ala Leu Lys Asp Ala Trp
                915                 920                 925

Asp Glu Leu Thr Trp Leu Glu Lys Phe Ser Ala Ile Arg His Ser Arg
                930                 935                 940

Lys Leu Leu Lys Phe Gly Arg Lys Pro Leu Ile Met Lys Asn Thr Val
945                 950                 955                 960

Asp Cys Gly Gly His Ile Asp Leu Ser Val Lys Ser Leu Phe Lys Phe
                965                 970                 975

His Leu Glu Leu Leu Lys Gly Thr Ile Ser Arg Ala Val Asn Gly Gly
                980                 985                 990

Ala Arg Lys Val Arg Val Ala Lys  Asn Ala Met Thr Lys  Gly Val Phe
                995                 1000                1005

Leu Lys Ile Tyr Ser Met Leu  Pro Asp Val Tyr Lys  Phe Ile Thr Val
                1010                1015                1020

Ser  Ser Val Leu Ser Leu  Leu Leu Thr Phe Leu  Phe Gln Ile Asp Cys
1025                 1030                1035                1040
```

-continued

```
Met Ile Arg Ala His  Arg Glu Ala Lys Val  Ala Ala Gln Leu Gln  Lys
            1045                 1050                 1055

Glu Ser Glu Trp  Asp Asn Ile Ile Asn  Arg Thr Phe Gln Tyr  Ser Lys
            1060                 1065                 1070

Leu Glu Asn  Pro Ile Gly Tyr Arg  Ser Thr Ala Glu Glu  Arg Leu Gln
            1075                 1080                 1085

Ser Glu  His Pro Glu Ala Phe  Glu Tyr Tyr Lys Phe  Cys Ile Gly Lys
            1090                 1095                 1100

Glu  Asp Leu Val Glu Gln  Ala Lys Gln Pro Glu  Ile Ala Tyr Phe Glu
1105                 1110                 1115                 1120

Lys Ile Ile Ala Phe  Ile Thr Leu Val Leu  Met Ala Phe Asp Ala  Glu
            1125                 1130                 1135

Arg Ser Asp Gly  Val Phe Lys Ile Leu  Asn Lys Phe Lys Gly  Ile Leu
            1140                 1145                 1150

Ser Ser Thr  Glu Arg Glu Ile Ile  Tyr Thr Gln Ser Leu  Asp Asp Tyr
            1155                 1160                 1165

Val Thr  Thr Phe Asp Asp Asn  Met Thr Ile Asn Leu  Glu Leu Asn Met
            1170                 1175                 1180

Asp  Glu Leu His Lys Thr  Ser Leu Pro Gly Val  Thr Phe Lys Gln Trp
1185                 1190                 1195                 1200

Trp Asn Gln Ile  Ser Arg Gly Asn Val  Lys Pro His Tyr Arg  Thr
            1205                 1210                 1215

Glu Gly His Phe  Met Glu Phe Thr Arg  Asp Thr Ala Ala Ser  Val Ala
            1220                 1225                 1230

Ser Glu Ile  Ser His Ser Pro Ala  Arg Asp Phe Leu Val  Arg Gly Ala
            1235                 1240                 1245

Val Gly  Ser Gly Lys Ser Thr  Gly Leu Pro Tyr His  Leu Ser Lys Arg
            1250                 1255                 1260

Gly  Arg Val Leu Met Leu  Glu Pro Thr Arg Pro  Leu Thr Asp Asn Met
1265                 1270                 1275                 1280

His Lys Gln Leu Arg  Ser Glu Pro Phe Asn  Cys Phe Pro Thr Leu  Arg
            1285                 1290                 1295

Met Arg Gly Lys  Ser Thr Phe Gly Ser  Ser Pro Ile Thr Val  Met Thr
            1300                 1305                 1310

Ser Gly Phe  Ala Leu His His Phe  Ala Arg Asn Ile Ala  Glu Val Lys
            1315                 1320                 1325

Thr Tyr  Asp Phe Val Ile Ile  Asp Glu Cys His Val  Asn Asp Ala Ser
            1330                 1335                 1340

Ala  Ile Ala Phe Arg Asn  Leu Leu Phe Glu His  Glu Phe Glu Gly Lys
1345                 1350                 1355                 1360

Val Leu Lys Val Ser  Ala Thr Pro Pro Gly  Arg Glu Val Glu Phe  Thr
            1365                 1370                 1375

Thr Gln Phe Pro  Val Lys Leu Lys Ile  Glu Glu Ala Leu Ser  Phe Gln
            1380                 1385                 1390

Glu Phe Val  Ser Leu Gln Gly Thr  Gly Ala Asn Ala Asp  Val Ile Ser
            1395                 1400                 1405

Cys Gly  Asp Asn Ile Leu Val  Tyr Val Ala Ser Tyr  Asn Asp Val Asp
            1410                 1415                 1420

Ser  Leu Gly Lys Leu Leu  Val Gln Lys Gly Tyr  Lys Val Ser Lys Ile
1425                 1430                 1435                 1440

Asp Gly Arg Thr Met  Lys Ser Gly Gly Thr  Glu Ile Ile Thr Glu  Gly
            1445                 1450                 1455

Thr Ser Val Lys  Lys His Phe Ile Val  Ala Thr Asn Ile Ile  Glu Asn
            1460                 1465                 1470
```

```
Gly Val Thr Ile Asp Ile Asp Val Val Asp Phe Gly Thr Lys Val
            1475                1480                1485

Val Pro Val Leu Asp Val Asp Asn Arg Ala Val Gln Tyr Asn Lys Thr
    1490                1495                1500

Val Val Ser Tyr Gly Glu Arg Ile Gln Lys Leu Gly Arg Val Gly Arg
1505                1510                1515                1520

His Lys Glu Gly Val Ala Leu Arg Ile Gly Gln Thr Asn Lys Thr Leu
            1525                1530                1535

Val Glu Ile Pro Glu Met Val Ala Thr Glu Ala Ala Phe Leu Cys Phe
            1540                1545                1550

Met Tyr Asn Leu Pro Val Thr Thr Gln Ser Val Ser Thr Thr Leu Leu
            1555                1560                1565

Glu Asn Ala Thr Leu Leu Gln Ala Arg Thr Met Ala Gln Phe Glu Leu
            1570                1575                1580

Ser Tyr Phe Tyr Thr Ile Asn Phe Val Arg Phe Asp Gly Ser Met His
1585                1590                1595                1600

Pro Val Ile His Asp Lys Leu Lys Arg Phe Lys Leu His Thr Cys Glu
            1605                1610                1615

Thr Phe Leu Asn Lys Leu Ala Ile Pro Asn Lys Gly Leu Ser Ser Trp
            1620                1625                1630

Leu Thr Ser Gly Glu Tyr Lys Arg Leu Gly Tyr Ile Ala Glu Asp Ala
            1635                1640                1645

Gly Ile Arg Ile Pro Phe Val Cys Lys Glu Ile Pro Asp Ser Leu His
            1650                1655                1660

Glu Glu Ile Trp His Ile Val Val Ala His Lys Gly Asp Ser Gly Ile
1665                1670                1675                1680

Gly Arg Leu Thr Ser Val Gln Ala Ala Lys Val Val Tyr Thr Leu Gln
            1685                1690                1695

Thr Asp Val His Ser Ile Ala Arg Thr Leu Ala Cys Ile Asn Arg Arg
            1700                1705                1710

Ile Ala Asp Glu Gln Met Lys Gln Ser His Phe Glu Ala Ala Thr Gly
            1715                1720                1725

Arg Ala Phe Ser Phe Thr Asn Tyr Ser Ile Gln Ser Ile Phe Asp Thr
            1730                1735                1740

Leu Lys Ala Asn Tyr Ala Thr Lys His Thr Lys Glu Asn Ile Ala Val
1745                1750                1755                1760

Leu Gln Gln Ala Lys Asp Gln Leu Leu Glu Phe Ser Asn Leu Ala Lys
            1765                1770                1775

Asp Gln Asp Val Thr Gly Ile Ile Gln Asp Phe Asn His Leu Glu Thr
            1780                1785                1790

Ile Tyr Leu Gln Ser Asp Ser Glu Val Ala Lys His Leu Lys Leu Lys
            1795                1800                1805

Ser His Trp Asn Lys Ser Gln Ile Thr Arg Asp Ile Ile Ala Leu
            1810                1815                1820

Ser Val Leu Ile Gly Gly Gly Trp Met Leu Ala Thr Tyr Phe Lys Asp
1825                1830                1835                1840

Lys Phe Asn Glu Pro Val Tyr Phe Gln Gly Lys Lys Asn Gln Lys His
            1845                1850                1855

Lys Leu Lys Met Arg Glu Ala Arg Gly Ala Arg Gly Gln Tyr Glu Val
            1860                1865                1870

Ala Ala Glu Pro Glu Ala Leu Glu His Tyr Phe Gly Ser Ala Tyr Asn
            1875                1880                1885

Asn Lys Gly Lys Arg Lys Gly Thr Thr Arg Gly Met Gly Ala Lys Ser
```

-continued

```
              1890                1895                1900
Arg  Lys  Phe  Ile  Asn  Met  Tyr  Gly  Phe  Asp  Pro  Thr  Asp  Phe  Ser  Tyr
1905                1910                1915                1920

Ile  Arg  Phe  Val  Asp  Pro  Leu  Thr  Gly  His  Thr  Ile  Asp  Glu  Ser  Thr
               1925                1930                1935

Asn  Ala  Pro  Ile  Asp  Leu  Val  Gln  His  Glu  Phe  Gly  Lys  Val  Arg  Thr
               1940                1945                1950

Arg  Met  Leu  Ile  Asp  Asp  Glu  Ile  Glu  Pro  Gln  Ser  Leu  Ser  Thr  His
               1955                1960                1965

Thr  Thr  Ile  His  Ala  Tyr  Leu  Val  Asn  Ser  Gly  Thr  Lys  Lys  Val  Leu
               1970                1975                1980

Lys  Val  Asp  Leu  Thr  Pro  His  Ser  Ser  Leu  Arg  Ala  Ser  Glu  Lys  Ser
1985                1990                1995                2000

Thr  Ala  Ile  Met  Gly  Phe  Pro  Glu  Arg  Glu  Asn  Glu  Leu  Arg  Gln  Thr
                    2005                2010                2015

Gly  Met  Ala  Val  Pro  Val  Ala  Tyr  Asp  Gln  Leu  Pro  Pro  Lys  Asn  Glu
               2020                2025                2030

Asp  Leu  Thr  Phe  Glu  Gly  Glu  Ser  Leu  Phe  Lys  Gly  Pro  Arg  Asp  Tyr
               2035                2040                2045

Asn  Pro  Ile  Ser  Ser  Thr  Ile  Cys  His  Leu  Thr  Asn  Glu  Ser  Asp  Gly
2050                2055                2060

His  Thr  Thr  Ser  Leu  Tyr  Gly  Ile  Gly  Phe  Gly  Pro  Phe  Ile  Ile  Thr
2065                2070                2075                2080

Asn  Lys  His  Leu  Phe  Arg  Arg  Asn  Asn  Gly  Thr  Leu  Leu  Val  Gln  Ser
               2085                2090                2095

Leu  His  Gly  Val  Phe  Lys  Val  Lys  Asn  Thr  Thr  Thr  Leu  Gln  Gln  His
               2100                2105                2110

Leu  Ile  Asp  Gly  Arg  Asp  Met  Ile  Ile  Ile  Arg  Met  Pro  Lys  Asp  Phe
               2115                2120                2125

Pro  Pro  Phe  Pro  Gln  Lys  Leu  Lys  Phe  Arg  Glu  Pro  Gln  Arg  Glu  Glu
               2130                2135                2140

Arg  Ile  Cys  Leu  Val  Thr  Thr  Asn  Phe  Gln  Thr  Lys  Ser  Met  Ser  Ser
2145                2150                2155                2160

Met  Val  Ser  Asp  Thr  Ser  Cys  Thr  Phe  Pro  Ser  Ser  Asp  Gly  Ile  Phe
                    2165                2170                2175

Trp  Lys  His  Trp  Ile  Gln  Thr  Lys  Asp  Gly  Gln  Cys  Gly  Ser  Pro  Leu
               2180                2185                2190

Val  Ser  Thr  Arg  Asp  Gly  Phe  Ile  Val  Gly  Ile  His  Ser  Ala  Ser  Asn
               2195                2200                2205

Phe  Thr  Asn  Thr  Asn  Asn  Tyr  Phe  Thr  Ser  Val  Pro  Lys  Asn  Phe  Met
               2210                2215                2220

Glu  Leu  Leu  Thr  Asn  Gln  Glu  Ala  Gln  Gln  Trp  Val  Ser  Gly  Trp  Arg
2225                2230                2235                2240

Leu  Asn  Ala  Asp  Ser  Val  Leu  Trp  Gly  Gly  His  Lys  Val  Phe  Met  Ser
               2245                2250                2255

Lys  Pro  Glu  Glu  Pro  Phe  Gln  Pro  Val  Lys  Glu  Ala  Thr  Gln  Leu  Met
               2260                2265                2270

Asn  Glu  Leu  Val  Tyr  Ser  Gln  Gly  Glu  Lys  Arg  Lys  Trp  Val  Val  Glu
               2275                2280                2285

Ala  Leu  Ser  Gly  Asn  Leu  Arg  Pro  Val  Ala  Glu  Cys  Pro  Ser  Gln  Leu
               2290                2295                2300

Val  Thr  Lys  His  Val  Val  Lys  Gly  Lys  Cys  Pro  Leu  Phe  Glu  Leu  Tyr
2305                2310                2315                2320
```

-continued

Leu Gln Leu Asn Pro Glu Lys Glu Ala Tyr Phe Lys Pro Met Met Gly
              2325             2330              2335

Ala Tyr Lys Pro Ser Arg Leu Asn Arg Glu Ala Phe Leu Lys Asp Ile
              2340             2345              2350

Leu Lys Tyr Ala Ser Glu Ile Glu Ile Gly Asn Val Asp Cys Asp Leu
              2355             2360              2365

Leu Glu Leu Ala Ile Ser Met Leu Val Thr Lys Leu Lys Ala Leu Gly
              2370             2375              2380

Phe Pro Thr Val Asn Tyr Ile Thr Asp Pro Glu Glu Ile Phe Ser Ala
2385              2390             2395              2400

Leu Asn Met Lys Ala Ala Met Gly Ala Leu Tyr Lys Gly Lys Lys Lys
              2405             2410              2415

Glu Ala Leu Ser Glu Leu Thr Leu Asp Glu Gln Glu Ala Met Leu Lys
              2420             2425              2430

Ala Ser Cys Leu Arg Leu Tyr Thr Gly Lys Leu Gly Ile Trp Asn Gly
              2435             2440              2445

Ser Leu Lys Ala Glu Leu Arg Pro Ile Glu Lys Val Glu Asn Asn Lys
              2450             2455             2460

Thr Arg Thr Phe Thr Ala Ala Pro Ile Asp Thr Leu Leu Ala Gly Lys
2465              2470             2475              2480

Val Cys Val Asp Asp Phe Asn Asn Gln Phe Tyr Asp Leu Asn Ile Lys
              2485             2490              2495

Ala Pro Trp Thr Val Gly Met Thr Lys Phe Tyr Gln Gly Trp Asn Glu
              2500             2505              2510

Leu Met Glu Ala Leu Pro Ser Gly Trp Val Tyr Cys Asp Ala Asp Gly
              2515             2520              2525

Ser Gln Phe Asp Ser Ser Leu Thr Pro Phe Leu Ile Asn Ala Val Leu
              2530             2535              2540

Lys Val Arg Leu Ala Phe Met Glu Glu Trp Asp Ile Gly Glu Gln Met
2545              2550             2555              2560

Leu Arg Asn Leu Tyr Thr Glu Ile Val Tyr Thr Pro Ile Leu Thr Pro
              2565             2570              2575

Asp Gly Thr Ile Ile Lys Lys His Lys Gly Asn Asn Ser Gly Gln Pro
              2580             2585              2590

Ser Thr Val Val Asp Asn Thr Leu Met Val Ile Ile Ala Met Leu Tyr
              2595             2600              2605

Thr Cys Glu Lys Cys Gly Ile Asn Lys Glu Glu Ile Val Tyr Tyr Val
              2610             2615              2620

Asn Gly Asp Asp Leu Leu Ile Ala Ile His Pro Asp Lys Ala Glu Arg
2625              2630             2635              2640

Leu Ser Arg Phe Lys Glu Ser Phe Gly Glu Leu Gly Leu Lys Tyr Glu
              2645             2650              2655

Phe Asp Cys Thr Thr Arg Asp Lys Thr Gln Leu Trp Phe Met Ser His
              2660             2665              2670

Arg Ala Leu Glu Arg Asp Gly Met Tyr Ile Pro Lys Leu Glu Glu Glu
              2675             2680              2685

Arg Ile Val Ser Ile Leu Glu Trp Asp Arg Ser Lys Glu Pro Ser His
              2690             2695              2700

Arg Leu Glu Ala Ile Cys Ala Ser Met Ile Glu Ala Trp Gly Tyr Asp
2705              2710             2715              2720

Lys Leu Val Glu Glu Ile Arg Asn Phe Tyr Ala Trp Val Leu Glu Gln
              2725             2730              2735

Ala Pro Tyr Ser Gln Leu Ala Glu Glu Gly Lys Ala Pro Tyr Leu Ala
              2740             2745              2750

Glu Thr Ala Leu Lys Phe Leu Tyr Thr Ser Gln His Gly Thr Asn Ser
            2755                 2760                 2765

Glu Ile Glu Glu Tyr Leu Lys Val Leu Tyr Asp Tyr Asp Ile Pro Thr
        2770                 2775                 2780

Thr Glu Asn Leu Tyr Phe Gln Ser Gly Thr Val Asp Ala Gly Ala Asp
2785                 2790                 2795                 2800

Ala Gly Lys Lys Lys Asp Gln Lys Asp Asp Lys Val Ala Glu Gln Ala
                2805                 2810                 2815

Ser Lys Asp Arg Asp Val Asn Ala Gly Thr Ser Gly Thr Phe Ser Val
            2820                 2825                 2830

Pro Arg Ile Asn Ala Met Ala Thr Lys Leu Gln Tyr Pro Arg Met Arg
        2835                 2840                 2845

Gly Glu Val Val Val Asn Leu Asn His Leu Leu Gly Tyr Lys Pro Gln
    2850                 2855                 2860

Gln Ile Asp Leu Ser Asn Ala Arg Ala Thr His Glu Gln Phe Ala Ala
2865                 2870                 2875                 2880

Trp His Gln Ala Val Met Thr Ala Tyr Gly Val Asn Glu Glu Gln Met
                2885                 2890                 2895

Lys Ile Leu Leu Asn Gly Phe Met Val Trp Cys Ile Glu Asn Gly Thr
            2900                 2905                 2910

Ser Pro Asn Leu Asn Gly Thr Trp Val Met Met Asp Gly Glu Asp Gln
        2915                 2920                 2925

Val Ser Tyr Pro Leu Lys Pro Met Val Glu Asn Ala Gln Pro Thr Leu
    2930                 2935                 2940

Arg Gln Ile Met Thr His Phe Ser Asp Leu Ala Glu Ala Tyr Ile Glu
2945                 2950                 2955                 2960

Met Arg Asn Arg Glu Arg Pro Tyr Met Pro Arg Tyr Gly Leu Gln Arg
                2965                 2970                 2975

Asn Ile Thr Asp Met Ser Leu Ser Arg Tyr Ala Phe Asp Phe Tyr Glu
            2980                 2985                 2990

Leu Thr Ser Lys Thr Pro Val Arg Ala Arg Glu Ala His Met Gln Met
        2995                 3000                 3005

Lys Ala Ala Ala Val Arg Asn Ser Gly Thr Arg Leu Phe Gly Leu Asp
    3010                 3015                 3020

Gly Asn Val Gly Thr Ala Glu Glu Asp Thr Glu Arg His Thr Ala His
3025                 3030                 3035                 3040

Asp Val Asn Arg Asn Met His Thr Leu Leu Gly Val Arg Gln
                3045                 3050

<210> SEQ ID NO 80
<211> LENGTH: 9
<212> TYPE: PRT
<213> ORGANISM: Homo Sapiens

<400> SEQUENCE: 80

Asn Ser Ser Gly Gly Asn Ser Gly Ser
                5

<210> SEQ ID NO 81
<211> LENGTH: 2755
<212> TYPE: DNA
<213> ORGANISM: Homo sapiens

<400> SEQUENCE: 81
ttaggacggg gcgatggcgg ctgagaggag ctgcgcgtgc gcgaacatgt aactggtggg      60
atctgcggcg gctcccagat gatggtcgtc ctcctgggcg cgacgaccct agtgctcgtc     120

```
gccgtgggcc catgggtgtt gtccgcagcc gcaggtggaa aaaatctaaa atctcctcaa    180
aaagtagagg tcgacatcat agatgacaac tttatcctga ggtggaacag gagcgatgag    240
tctgtcggga atgtgacttt ttcattcgat tatcaaaaaa ctgggatgga taattggata    300
aaattgtctg ggtgtcagaa tattactagt accaaatgca acttttcttc actcaagctg    360
aatgtttatg aagaaattaa attgcgtata gagcagaaaa agaaaacac ttcttcatgg     420
tatgaggttg actcatttac accatttcgc aaagctcaga ttggtcctcc agaagtacat    480
ttagaagctg aagataaggc aatagtgata cacatctctc ctggaacaaa agatagtgtt    540
atgtgggctt tggatggttt aagctttaca tatagcttac ttatctggaa aaactcttca    600
ggtgtagaag aaaggattga aaatatttat tccagacata aaatttataa actctcacca    660
gagactactt attgtctaaa agttaaagca gcactactta cgtcatggaa aattggtgtc    720
tatagtccag tacattgtat aaagaccaca gttgaaaatg aactacctcc accagaaaat    780
atagaagtca gtgtccaaaa tcagaactat gttcttaaat gggattatac atatgcaaac    840
atgaccttt c aagttcagtg gctccacgcc ttttaaaaa ggaatcctgg aaaccatttg    900
tataaatgga acaaatacc tgactgtgaa atgtcaaaa ctacccagtg tgtctttcct      960
caaaacgttt tccaaaaagg aatttacctt ctccgcgtac aagcatctga tggaaataac   1020
acatctttt ggtctgaaga gataaagttt gatactgaaa tacaagcttt cctacttcct    1080
ccagtcttta acattagatc ccttagtgat tcattccata tctatatcgg tgctccaaaa   1140
cagtctggaa acacgcctgt gatccaggat tatccactga tttatgaaat tatttttgg    1200
gaaaacactt caaatgctga gagaaaaatt atcgagaaaa aaactgatgt tacagttcct   1260
aatttgaaac cactgactgt atattgtgtg aaagccagag cacacaccat ggatgaaaag   1320
ctgaataaaa gcagtgtttt tagtgacgct gtatgtgaga aaacaaaacc aggaaatacc   1380
tctaaaattt ggcttatagt tggaatttgt attgcattat ttgctctccc gtttgtcatt   1440
tatgctgcga agtcttctt gagatgcatc aattatgtct ctttccatc acttaaacct    1500
tcttccagta tagatgagta tttctctgaa cagccattga agaatcttct gctttcaact   1560
tctgaggaac aaatcgaaaa atgtttcata attgaaaata taagcacaat tgctacagta   1620
gaagaaacta atcaaactga tgaagatcat aaaaaatac gttcccaaac tagccaagat   1680
tcaggaaatt attctaatga agatgaaagc gaaagtaaaa caagtgaaga actacagcag   1740
gactttgtat gaccagaaat gaactgtgtc aagtataagg ttttttcagca ggagttacac   1800
tgggagcctg aggtcctcac cttcctctca gtaactacag agaggacgtt tcctgtttag   1860
ggaagaaaa aacatcttca gatcataggt cctaaaaata cgggcaagct cttaactatt   1920
taaaatgaa attacaggcc cgggcacggt ggctcacacc tgtaatccca gcactttggg   1980
aggctgaggc aggcagatca tgaggtcaag agatcgagac cagcctggcc aacgtggtga   2040
aaccccatct ctactaaaaa tacaaaaatt agccgggtag taggtaggcg cgcgcctgtt   2100
gtcttagcta ctcaggaggc tgaggcagga gaatcgcttg aaaacaggag gtggaggttg   2160
cagtgagccg agatcacgcc actgcactcc agcctggtga cagcgtgaga ctcttttaaaa  2220
aaagaaatta aaagagttga gacaaacgtt tcctacattc ttttccatgt gtaaaatcat   2280
gaaaaagcct gtcaccggac ttgcattgga tgagatgagt cagaccaaaa cagtggccac   2340
ccgtcttcct cctgtgagcc taagtgcagc cgtgctagct gcgcaccgtg gctaaggatg   2400
acgtctgtgt tcctgtccat cactgatgct gctggctact gcatgtgcca cacctgtctg   2460
ttcgccattc ctaacattct gtttcattct tcctcgggag atatttcaaa catttggtct   2520
```

```
tttcttttaa cactgagggt aggcccttag gaaatttatt taggaaagtc tgaacacgtt    2580
atcacttggt tttctggaaa gtagcttacc ctagaaaaca gctgcaaatg ccagaaagat    2640
gatccctaaa aatgttgagg gacttctgtt cattcatccc gagaacattg gcttccacat    2700
cacagtatct acccttacat ggtttaggat taaagccagg caatctttta ctatg         2755

<210> SEQ ID NO 82
<211> LENGTH: 9
<212> TYPE: PRT
<213> ORGANISM: Homo Sapiens

<400> SEQUENCE: 82

Gly Ser Glu Asn Leu Tyr Phe Gln Leu
                5

<210> SEQ ID NO 83
<211> LENGTH: 2897
<212> TYPE: DNA
<213> ORGANISM: Homo sapiens

<400> SEQUENCE: 83
cccgcactaa agacgcttct tcccggcggg taggaatccc gccggcgagc cgaacagttc      60
cccgagcgca gcccgcggac caccaccccgg ccgcacgggc cgcttttgtc ccccgcccgc    120
cgcttctgtc cgagaggccg cccgcgaggc gcatcctgac cgcgagcgtc gggtcccaga     180
gccgggcgcg gctggggccc gaggctagca tctctcggga gccgcaaggc gagagctgca    240
aagtttaatt agacacttca gaattttgat cacctaatgt tgatttcaga tgtaaaagtc    300
aagagaagac tctaaaaata gcaaagatgc ttttgagcca gaatgccttc atcttcagat    360
cacttaattt ggttctcatg gtgtatatca gcctcgtgtt tggtatttca tatgattcgc    420
ctgattacac agatgaatct tgcactttca agatatcatt gcgaaatttc cggtccatct    480
tatcatggga attaaaaaac cactccattg taccaactca ctatacattg ctgtatacaa    540
tcatgagtaa accagaagat ttgaaggtgg ttaagaactg tgcaaatacc acaagatcat    600
tttgtgacct cacagatgag tggagaagca cacacgaggc ctatgtcacc gtcctagaag    660
gattcagcgg gaacacaacg ttgttcagtt gctcacacaa tttctggctg ccatagaca    720 tgtcttttga accaccagag tttgagattg ttggttttac caaccacatt aatgtgatgg    780
tgaaatttcc atctattgtt gaggaagaat tacagtttga tttatctctc gtcattgaag    840
aacagtcaga gggaattgtt aagaagcata aacccgaaat aaaaggaaac atgagtggaa    900
atttcaccta tatcattgac aagttaattc caaacacgaa ctactgtgta tctgtttatt    960
tagagcacag tgatgagcaa gcagtaataa agtctccctt aaaatgcacc ctccttccac   1020
ctggccagga atcagaatca gcagaatctg ccaaaatagg aggataatt actgtgtttt    1080 tgatagcatt ggtcttgaca agcaccatag tgacactgaa atggattggt tatatatgct    1140
taagaaatag cctccccaaa gtcttgaatt ttcataactt tttagcctgg ccatttccta    1200
acctgccacc gttggaagcc atggatatgg tggaggtcat ttacatcaac agaaagaaga    1260
aagtgtggga ttataattat gatgatgaaa gtgatagcga tactgaggca gcgcccagga    1320
caagtggcgg tggctatacc atgcatggac tgactgtcag gcctctgggt caggcctctg    1380
ccacctctac agaatcccag ttgatagacc cggagtccga ggaggagcct gacctgcctg    1440
aggttgatgt ggagctcccc acgatgccaa aggacagccc tcagcagttg gaactcttga    1500
gtgggccctg tgagaggaga aagagtccac tccaggaccc ttttcccgaa gaggactaca    1560
```

```
gctccacgga ggggtctggg ggcagaatta ccttcaatgt ggacttaaac tctgtgtttt    1620
tgagagttct tgatgacgag gacagtgacg acttagaagc ccctctgatg ctatcgtctc    1680
atctggaaga gatggttgac ccagaggatc ctgataatgt gcaatcaaac catttgctgg    1740
ccagcgggga agggacacag ccaacctttc cagcccctc ttcagagggc ctgtggtccg     1800
aagatgctcc atctgatcaa agtgacactt ctgagtcaga tgttgacctt ggggatggtt    1860
atataatgag atgactccaa aactattgaa tgaacttgga cagacaagca cctacagggt    1920
tctttgtctc tgcatcctaa cttgctgcct tatcgtctgc aagtgttctc caagggaagg    1980
aggaggaaac tgtggtgttc ctttcttcca ggtgacatca cctatgcaca ttcccagtat    2040
ggggaccata gtatcattca gtgcattgtt tacatattca aagtggtgca ctttgaagga    2100
agcacatgtg caccttttcct ttacactaat gcacttagga tgtttctgca tcatgtctac    2160
cagggagcag ggttccccac agtttcagag gtggtccagg accctatgat atttctcttc    2220
tttcgttctt ttttttttt ttttgagaca gagtctcgtt ctgtcgccca agctggagcg    2280
caatggtgtg atcttggctc actgcaacat ccgcctcccg ggttcaggtg attctcctgc    2340
ctcagcctcc ctcgcaagta gctgggatta caggcgcctg ccaccatgcc tagcaaattt    2400 ttgtatttt agtggagaca ggattttacc atgttggcca ggctggtctc gaactcctga    2460
cctcaagtga tctgccctcc tcagcctcgt aaagtgctgg gattacaggg gtgagccgct    2520
gtgcctggct ggccctgtga tatttctgtg aaataaattg gccagggtg ggagcaggga    2580 aagaaaagga aaatagtagc aagagctgca aagcaggcag gaaggagga ggagagccag    2640 gtgagcagtg gagagaaggg gggccctgca caaggaaaca ggggaagagcc atcgaagttt    2700 cagtcggtga gccttgggca cctcacccat gtcacatcct gtctcctgca attggaattc    2760
caccttgtcc agccctcccc agttaaagtg gggaagacag actttaggat cacgtgtgtg    2820
actaatacag aaaggaaaca tggcgtcggg gagagggata aaacctgaat gccatatttt    2880
aagttaaaaa aaaaaaa                                                   2897

<210> SEQ ID NO 84
<211> LENGTH: 3054
<212> TYPE: PRT
<213> ORGANISM: Homo sapiens

<400> SEQUENCE: 84

Met Ala Leu Ile Phe Gly Thr Val Asn Ala Asn Ile Leu Lys Glu Val
 1               5                  10                  15

Phe Gly Gly Ala Arg Met Ala Cys Val Thr Ser Ala His Met Ala Gly
            20                  25                  30

Ala Asn Gly Ser Ile Leu Lys Lys Ala Glu Glu Thr Ser Arg Ala Ile
        35                  40                  45

Met His Lys Pro Val Ile Phe Gly Glu Asp Tyr Ile Thr Glu Ala Asp
    50                  55                  60

Leu Pro Tyr Thr Pro Leu His Leu Glu Val Asp Ala Glu Met Glu Arg
65                  70                  75                  80

Met Tyr Tyr Leu Gly Arg Arg Ala Leu Thr His Gly Lys Arg Arg Lys
                85                  90                  95

Val Ser Val Asn Asn Lys Arg Asn Arg Arg Lys Val Ala Lys Thr
            100                 105                 110

Tyr Val Gly Arg Asp Ser Ile Val Glu Lys Ile Val Pro His Thr
        115                 120                 125

Glu Arg Lys Val Asp Thr Thr Ala Ala Val Glu Asp Ile Cys Asn Glu
    130                 135                 140
```

```
Ala Thr Thr Gln Leu Val His Asn Ser Met Pro Lys Arg Lys Lys Gln
145                 150                 155                 160

Lys Asn Phe Leu Pro Ala Thr Ser Leu Ser Asn Val Tyr Ala Gln Thr
                165                 170                 175

Trp Ser Ile Val Arg Lys Arg His Met Gln Val Glu Ile Ile Ser Lys
            180                 185                 190

Lys Ser Val Arg Ala Arg Val Lys Arg Phe Glu Gly Ser Val Gln Leu
        195                 200                 205

Phe Ala Ser Val Arg His Met Tyr Gly Glu Arg Lys Arg Val Asp Leu
    210                 215                 220

Arg Ile Asp Asn Trp Gln Gln Glu Thr Leu Leu Asp Leu Ala Lys Arg
225                 230                 235                 240

Phe Lys Asn Glu Arg Val Asp Gln Ser Lys Leu Thr Phe Gly Ser Ser
                245                 250                 255

Gly Leu Val Leu Arg Gln Gly Ser Tyr Gly Pro Ala His Trp Tyr Arg
            260                 265                 270

His Gly Met Phe Ile Val Arg Gly Arg Ser Asp Gly Met Leu Val Asp
        275                 280                 285

Ala Arg Ala Lys Val Thr Phe Ala Val Cys His Ser Met Thr His Tyr
    290                 295                 300

Ser Asp Lys Ser Ile Ser Glu Ala Phe Phe Ile Pro Tyr Ser Lys Lys
305                 310                 315                 320

Phe Leu Glu Leu Arg Pro Asp Gly Ile Ser His Glu Cys Thr Arg Gly
                325                 330                 335

Val Ser Val Glu Arg Cys Gly Glu Val Ala Ala Ile Leu Thr Gln Ala
            340                 345                 350

Leu Ser Pro Cys Gly Lys Ile Thr Cys Lys Arg Cys Met Val Glu Thr
        355                 360                 365

Pro Asp Ile Val Glu Gly Glu Ser Gly Glu Ser Val Thr Asn Gln Gly
    370                 375                 380

Lys Leu Leu Ala Met Leu Lys Glu Gln Tyr Pro Asp Phe Pro Met Ala
385                 390                 395                 400

Glu Lys Leu Leu Thr Arg Phe Leu Gln Gln Lys Ser Leu Val Asn Thr
                405                 410                 415

Asn Leu Thr Ala Cys Val Ser Val Lys Gln Leu Ile Gly Asp Arg Lys
            420                 425                 430

Gln Ala Pro Phe Thr His Val Leu Ala Val Ser Glu Ile Leu Phe Lys
        435                 440                 445

Gly Asn Lys Leu Thr Gly Ala Asp Leu Glu Glu Ala Ser Thr His Met
    450                 455                 460

Leu Glu Ile Ala Arg Phe Leu Asn Asn Arg Thr Glu Asn Met Arg Ile
465                 470                 475                 480

Gly His Leu Gly Ser Phe Arg Asn Lys Ile Ser Ser Lys Ala His Val
                485                 490                 495

Asn Asn Ala Leu Met Cys Asp Asn Gln Leu Asp Gln Asn Gly Asn Phe
            500                 505                 510

Ile Trp Gly Leu Arg Gly Ala His Ala Lys Arg Phe Leu Lys Gly Phe
        515                 520                 525

Phe Thr Glu Ile Asp Pro Asn Glu Gly Tyr Asp Lys Tyr Val Ile Arg
    530                 535                 540

Lys His Ile Arg Gly Ser Arg Lys Leu Ala Ile Gly Asn Leu Ile Met
545                 550                 555                 560

Ser Thr Asp Phe Gln Thr Leu Arg Gln Gln Ile Gln Gly Glu Thr Ile
```

-continued

```
                565                 570                 575
Glu Arg Lys Glu Ile Gly Asn His Cys Ile Ser Met Arg Asn Gly Asn
            580                 585                 590
Tyr Val Tyr Pro Cys Cys Val Thr Leu Glu Asp Gly Lys Ala Gln
            595                 600                 605
Tyr Ser Asp Leu Lys His Pro Thr Lys Arg His Leu Val Ile Gly Asn
            610                 615                 620
Ser Gly Asp Ser Lys Tyr Leu Asp Leu Pro Val Leu Asn Glu Glu Lys
625                 630                 635                 640
Met Tyr Ile Ala Asn Glu Gly Tyr Cys Tyr Met Asn Ile Phe Phe Ala
            645                 650                 655
Leu Leu Val Asn Val Lys Glu Glu Asp Ala Lys Asp Phe Thr Lys Phe
            660                 665                 670
Ile Arg Asp Thr Ile Val Pro Lys Leu Gly Ala Trp Pro Thr Met Gln
            675                 680                 685
Asp Val Ala Thr Ala Cys Tyr Leu Leu Ser Ile Leu Tyr Pro Asp Val
            690                 695                 700
Leu Arg Ala Glu Leu Pro Arg Ile Leu Val Asp His Asp Asn Lys Thr
705                 710                 715                 720
Met His Val Leu Asp Ser Tyr Gly Ser Arg Thr Thr Gly Tyr His Met
            725                 730                 735
Leu Lys Met Asn Thr Thr Ser Gln Leu Ile Glu Phe Val His Ser Gly
            740                 745                 750
Leu Glu Ser Glu Met Lys Thr Tyr Asn Val Gly Gly Met Asn Arg Asp
            755                 760                 765
Val Val Thr Gln Gly Ala Ile Glu Met Leu Ile Lys Ser Ile Tyr Lys
            770                 775                 780
Pro His Leu Met Lys Gln Leu Leu Glu Glu Pro Tyr Ile Ile Val
785                 790                 795                 800
Leu Ala Ile Val Ser Pro Ser Ile Leu Ile Ala Met Tyr Asn Ser Gly
            805                 810                 815
Thr Phe Glu Gln Ala Leu Gln Met Trp Leu Pro Asn Thr Met Arg Leu
            820                 825                 830
Ala Asn Leu Ala Ala Ile Leu Ser Ala Leu Ala Gln Lys Leu Thr Leu
            835                 840                 845
Ala Asp Leu Phe Val Gln Gln Arg Asn Leu Ile Asn Glu Tyr Ala Gln
            850                 855                 860
Val Ile Leu Asp Asn Leu Ile Asp Gly Val Arg Val Asn His Ser Leu
865                 870                 875                 880
Ser Leu Ala Met Glu Ile Val Thr Ile Lys Leu Ala Thr Gln Glu Met
            885                 890                 895
Asp Met Ala Leu Arg Glu Gly Gly Tyr Ala Val Thr Ser Glu Lys Val
            900                 905                 910
His Glu Met Leu Glu Lys Asn Tyr Val Lys Ala Leu Lys Asp Ala Trp
            915                 920                 925
Asp Glu Leu Thr Trp Leu Glu Lys Phe Ser Ala Ile Arg His Ser Arg
            930                 935                 940
Lys Leu Leu Lys Phe Gly Arg Lys Pro Leu Ile Met Lys Asn Thr Val
945                 950                 955                 960
Asp Cys Gly Gly His Ile Asp Leu Ser Val Lys Ser Leu Phe Lys Phe
            965                 970                 975
His Leu Glu Leu Leu Lys Gly Thr Ile Ser Arg Ala Val Asn Gly Gly
            980                 985                 990
```

```
Ala Arg Lys Val Arg Val Ala Lys  Asn Ala Met Thr Lys  Gly Val Phe
        995                 1000                1005

Leu Lys  Ile Tyr Ser Met Leu  Pro Asp Val Tyr Lys  Phe Ile Thr
    1010                 1015                1020

Val Ser  Ser Val Leu Ser Leu  Leu Leu Thr Phe Leu  Phe Gln Ile
    1025                 1030                1035

Asp Cys  Met Ile Arg Ala His  Arg Glu Ala Lys Val  Ala Ala Gln
    1040                 1045                1050

Leu Gln  Lys Glu Ser Glu Trp  Asp Asn Ile Ile Asn  Arg Thr Phe
    1055                 1060                1065

Gln Tyr  Ser Lys Leu Glu Asn  Pro Ile Gly Tyr Arg  Ser Thr Ala
    1070                 1075                1080

Glu Glu  Arg Leu Gln Ser Glu  His Pro Glu Ala Phe  Glu Tyr Tyr
    1085                 1090                1095

Lys Phe  Cys Ile Gly Lys Glu  Asp Leu Val Glu Gln  Ala Lys Gln
    1100                 1105                1110

Pro Glu  Ile Ala Tyr Phe Glu  Lys Ile Ile Ala Phe  Ile Thr Leu
    1115                 1120                1125

Val Leu  Met Ala Phe Asp Ala  Glu Arg Ser Asp Gly  Val Phe Lys
    1130                 1135                1140

Ile Leu  Asn Lys Phe Lys Gly  Ile Leu Ser Ser Thr  Glu Arg Glu
    1145                 1150                1155

Ile Ile  Tyr Thr Gln Ser Leu  Asp Asp Tyr Val Thr  Thr Phe Asp
    1160                 1165                1170

Asp Asn  Met Thr Ile Asn Leu  Glu Leu Asn Met Asp  Glu Leu His
    1175                 1180                1185

Lys Thr  Ser Leu Pro Gly Val  Thr Phe Lys Gln Trp  Trp Asn Asn
    1190                 1195                1200

Gln Ile  Ser Arg Gly Asn Val  Lys Pro His Tyr Arg  Thr Glu Gly
    1205                 1210                1215

His Phe  Met Glu Phe Thr Arg  Asp Thr Ala Ala Ser  Val Ala Ser
    1220                 1225                1230

Glu Ile  Ser His Ser Pro Ala  Arg Asp Phe Leu Val  Arg Gly Ala
    1235                 1240                1245

Val Gly  Ser Gly Lys Ser Thr  Gly Leu Pro Tyr His  Leu Ser Lys
    1250                 1255                1260

Arg Gly  Arg Val Leu Met Leu  Glu Pro Thr Arg Pro  Leu Thr Asp
    1265                 1270                1275

Asn Met  His Lys Gln Leu Arg  Ser Glu Pro Phe Asn  Cys Phe Pro
    1280                 1285                1290

Thr Leu  Arg Met Arg Gly Lys  Ser Thr Phe Gly Ser  Ser Pro Ile
    1295                 1300                1305

Thr Val  Met Thr Ser Gly Phe  Ala Leu His His Phe  Ala Arg Asn
    1310                 1315                1320

Ile Ala  Glu Val Lys Thr Tyr  Asp Phe Val Ile Ile  Asp Glu Cys
    1325                 1330                1335

His Val  Asn Asp Ala Ser Ala  Ile Ala Phe Arg Asn  Leu Leu Phe
    1340                 1345                1350

Glu His  Glu Phe Glu Gly Lys  Val Leu Lys Val Ser  Ala Thr Pro
    1355                 1360                1365

Pro Gly  Arg Glu Val Glu Phe  Thr Thr Gln Phe Pro  Val Lys Leu
    1370                 1375                1380

Lys Ile  Glu Glu Ala Leu Ser  Phe Gln Glu Phe Val  Ser Leu Gln
    1385                 1390                1395
```

```
Gly Thr Gly Ala Asn Ala Asp Val Ile Ser Cys Gly Asp Asn Ile
    1400                1405            1410
Leu Val Tyr Val Ala Ser Tyr Asn Asp Val Asp Ser Leu Gly Lys
    1415                1420            1425
Leu Leu Val Gln Lys Gly Tyr Lys Val Ser Lys Ile Asp Gly Arg
    1430                1435            1440
Thr Met Lys Ser Gly Gly Thr Glu Ile Ile Thr Glu Gly Thr Ser
    1445                1450            1455
Val Lys Lys His Phe Ile Val Ala Thr Asn Ile Ile Glu Asn Gly
    1460                1465            1470
Val Thr Ile Asp Ile Asp Val Val Val Asp Phe Gly Thr Lys Val
    1475                1480            1485
Val Pro Val Leu Asp Val Asp Asn Arg Ala Val Gln Tyr Asn Lys
    1490                1495            1500
Thr Val Val Ser Tyr Gly Glu Arg Ile Gln Lys Leu Gly Arg Val
    1505                1510            1515
Gly Arg His Lys Glu Gly Val Ala Leu Arg Ile Gly Gln Thr Asn
    1520                1525            1530
Lys Thr Leu Val Glu Ile Pro Glu Met Val Ala Thr Glu Ala Ala
    1535                1540            1545
Phe Leu Cys Phe Met Tyr Asn Leu Pro Val Thr Thr Gln Ser Val
    1550                1555            1560
Ser Thr Thr Leu Leu Glu Asn Ala Thr Leu Leu Gln Ala Arg Thr
    1565                1570            1575
Met Ala Gln Phe Glu Leu Ser Tyr Phe Tyr Thr Ile Asn Phe Val
    1580                1585            1590
Arg Phe Asp Gly Ser Met His Pro Val Ile His Asp Lys Leu Lys
    1595                1600            1605
Arg Phe Lys Leu His Thr Cys Glu Thr Phe Leu Asn Lys Leu Ala
    1610                1615            1620
Ile Pro Asn Lys Gly Leu Ser Ser Trp Leu Thr Ser Gly Glu Tyr
    1625                1630            1635
Lys Arg Leu Gly Tyr Ile Ala Glu Asp Ala Gly Ile Arg Ile Pro
    1640                1645            1650
Phe Val Cys Lys Glu Ile Pro Asp Ser Leu His Glu Glu Ile Trp
    1655                1660            1665
His Ile Val Val Ala His Lys Gly Asp Ser Gly Ile Gly Arg Leu
    1670                1675            1680
Thr Ser Val Gln Ala Ala Lys Val Val Tyr Thr Leu Gln Thr Asp
    1685                1690            1695
Val His Ser Ile Ala Arg Thr Leu Ala Cys Ile Asn Arg Arg Ile
    1700                1705            1710
Ala Asp Glu Gln Met Lys Gln Ser His Phe Glu Ala Ala Thr Gly
    1715                1720            1725
Arg Ala Phe Ser Phe Thr Asn Tyr Ser Ile Gln Ser Ile Phe Asp
    1730                1735            1740
Thr Leu Lys Ala Asn Tyr Ala Thr Lys His Thr Lys Glu Asn Ile
    1745                1750            1755
Ala Val Leu Gln Gln Ala Lys Asp Gln Leu Leu Glu Phe Ser Asn
    1760                1765            1770
Leu Ala Lys Asp Gln Asp Val Thr Gly Ile Ile Gln Asp Phe Asn
    1775                1780            1785
His Leu Glu Thr Ile Tyr Leu Gln Ser Asp Ser Glu Val Ala Lys
```

-continued

```
            1790                1795                1800
His Leu Lys Leu Lys Ser His Trp Asn Lys Ser Gln Ile Thr Arg
    1805                1810                1815

Asp Ile Ile Ile Ala Leu Ser Val Leu Ile Gly Gly Trp Met
    1820                1825                1830

Leu Ala Thr Tyr Phe Lys Asp Lys Phe Asn Glu Pro Val Tyr Phe
    1835                1840                1845

Gln Gly Lys Lys Asn Gln Lys His Lys Leu Lys Met Arg Glu Ala
    1850                1855                1860

Arg Gly Ala Arg Gly Gln Tyr Glu Val Ala Ala Glu Pro Glu Ala
    1865                1870                1875

Leu Glu His Tyr Phe Gly Ser Ala Tyr Asn Asn Lys Gly Lys Arg
    1880                1885                1890

Lys Gly Thr Thr Arg Gly Met Gly Ala Lys Ser Arg Lys Phe Ile
    1895                1900                1905

Asn Met Tyr Gly Phe Asp Pro Thr Asp Phe Ser Tyr Ile Arg Phe
    1910                1915                1920

Val Asp Pro Leu Thr Gly His Thr Ile Asp Glu Ser Thr Asn Ala
    1925                1930                1935

Pro Ile Asp Leu Val Gln His Glu Phe Gly Lys Val Arg Thr Arg
    1940                1945                1950

Met Leu Ile Asp Asp Glu Ile Glu Pro Gln Ser Leu Ser Thr His
    1955                1960                1965

Thr Thr Ile His Ala Tyr Leu Val Asn Ser Gly Thr Lys Lys Val
    1970                1975                1980

Leu Lys Val Asp Leu Thr Pro His Ser Ser Leu Arg Ala Ser Glu
    1985                1990                1995

Lys Ser Thr Ala Ile Met Gly Phe Pro Glu Arg Glu Asn Glu Leu
    2000                2005                2010

Arg Gln Thr Gly Met Ala Val Pro Val Ala Tyr Asp Gln Leu Pro
    2015                2020                2025

Pro Lys Asn Glu Asp Leu Thr Phe Glu Gly Glu Ser Leu Phe Lys
    2030                2035                2040

Gly Pro Arg Asp Tyr Asn Pro Ile Ser Ser Thr Ile Cys His Leu
    2045                2050                2055

Thr Asn Glu Ser Asp Gly His Thr Thr Ser Leu Tyr Gly Ile Gly
    2060                2065                2070

Phe Gly Pro Phe Ile Ile Thr Asn Lys His Leu Phe Arg Arg Asn
    2075                2080                2085

Asn Gly Thr Leu Leu Val Gln Ser Leu His Gly Val Phe Lys Val
    2090                2095                2100

Lys Asn Thr Thr Thr Leu Gln Gln His Leu Ile Asp Gly Arg Asp
    2105                2110                2115

Met Ile Ile Ile Arg Met Pro Lys Asp Phe Pro Pro Phe Pro Gln
    2120                2125                2130

Lys Leu Lys Phe Arg Glu Pro Gln Arg Glu Glu Arg Ile Cys Leu
    2135                2140                2145

Val Thr Thr Asn Phe Gln Thr Lys Ser Met Ser Ser Met Val Ser
    2150                2155                2160

Asp Thr Ser Cys Thr Phe Pro Ser Ser Asp Gly Ile Phe Trp Lys
    2165                2170                2175

His Trp Ile Gln Thr Lys Asp Gly Gln Cys Gly Ser Pro Leu Val
    2180                2185                2190
```

```
Ser Thr Arg Asp Gly Phe Ile Val Gly Ile His Ser Ala Ser Asn
    2195            2200                2205

Phe Thr Asn Thr Asn Asn Tyr Phe Thr Ser Val Pro Lys Asn Phe
    2210            2215                2220

Met Glu Leu Leu Thr Asn Gln Glu Ala Gln Gln Trp Val Ser Gly
    2225            2230                2235

Trp Arg Leu Asn Ala Asp Ser Val Leu Trp Gly His Lys Val
    2240            2245                2250

Phe Met Ser Lys Pro Glu Glu Pro Phe Gln Pro Val Lys Glu Ala
    2255            2260                2265

Thr Gln Leu Met Asn Glu Leu Val Tyr Ser Gln Gly Glu Lys Arg
    2270            2275                2280

Lys Trp Val Val Glu Ala Leu Ser Gly Asn Leu Arg Pro Val Ala
    2285            2290                2295

Glu Cys Pro Ser Gln Leu Val Thr Lys His Val Val Lys Gly Lys
    2300            2305                2310

Cys Pro Leu Phe Glu Leu Tyr Leu Gln Leu Asn Pro Glu Lys Glu
    2315            2320                2325

Ala Tyr Phe Lys Pro Met Met Gly Ala Tyr Lys Pro Ser Arg Leu
    2330            2335                2340

Asn Arg Glu Ala Phe Leu Lys Asp Ile Leu Lys Tyr Ala Ser Glu
    2345            2350                2355

Ile Glu Ile Gly Asn Val Asp Cys Asp Leu Leu Glu Leu Ala Ile
    2360            2365                2370

Ser Met Leu Val Thr Lys Leu Lys Ala Leu Gly Phe Pro Thr Val
    2375            2380                2385

Asn Tyr Ile Thr Asp Pro Glu Glu Ile Phe Ser Ala Leu Asn Met
    2390            2395                2400

Lys Ala Ala Met Gly Ala Leu Tyr Lys Gly Lys Lys Lys Glu Ala
    2405            2410                2415

Leu Ser Glu Leu Thr Leu Asp Glu Gln Glu Ala Met Leu Lys Ala
    2420            2425                2430

Ser Cys Leu Arg Leu Tyr Thr Gly Lys Leu Gly Ile Trp Asn Gly
    2435            2440                2445

Ser Leu Lys Ala Glu Leu Arg Pro Ile Glu Lys Val Glu Asn Asn
    2450            2455                2460

Lys Thr Arg Thr Phe Thr Ala Ala Pro Ile Asp Thr Leu Leu Ala
    2465            2470                2475

Gly Lys Val Cys Val Asp Asp Phe Asn Asn Gln Phe Tyr Asp Leu
    2480            2485                2490

Asn Ile Lys Ala Pro Trp Thr Val Gly Met Thr Lys Phe Tyr Gln
    2495            2500                2505

Gly Trp Asn Glu Leu Met Glu Ala Leu Pro Ser Gly Trp Val Tyr
    2510            2515                2520

Cys Asp Ala Asp Gly Ser Gln Phe Asp Ser Ser Leu Thr Pro Phe
    2525            2530                2535

Leu Ile Asn Ala Val Leu Lys Val Arg Leu Ala Phe Met Glu Glu
    2540            2545                2550

Trp Asp Ile Gly Glu Gln Met Leu Arg Asn Leu Tyr Thr Glu Ile
    2555            2560                2565

Val Tyr Thr Pro Ile Leu Thr Pro Asp Gly Thr Ile Ile Lys Lys
    2570            2575                2580

His Lys Gly Asn Asn Ser Gly Gln Pro Ser Thr Val Val Asp Asn
    2585            2590                2595
```

```
Thr Leu Met Val Ile Ile Ala Met Leu Tyr Thr Cys Glu Lys Cys
    2600                2605                2610

Gly Ile Asn Lys Glu Glu Ile Val Tyr Val Asn Gly Asp Asp
    2615                2620                2625

Leu Leu Ile Ala Ile His Pro Asp Lys Ala Glu Arg Leu Ser Arg
    2630                2635                2640

Phe Lys Glu Ser Phe Gly Glu Leu Gly Leu Lys Tyr Glu Phe Asp
    2645                2650                2655

Cys Thr Thr Arg Asp Lys Thr Gln Leu Trp Phe Met Ser His Arg
    2660                2665                2670

Ala Leu Glu Arg Asp Gly Met Tyr Ile Pro Lys Leu Glu Glu Glu
    2675                2680                2685

Arg Ile Val Ser Ile Leu Glu Trp Asp Arg Ser Lys Glu Pro Ser
    2690                2695                2700

His Arg Leu Glu Ala Ile Cys Ala Ser Met Ile Glu Ala Trp Gly
    2705                2710                2715

Tyr Asp Lys Leu Val Glu Glu Ile Arg Asn Phe Tyr Ala Trp Val
    2720                2725                2730

Leu Glu Gln Ala Pro Tyr Ser Gln Leu Ala Glu Glu Gly Lys Ala
    2735                2740                2745

Pro Tyr Leu Ala Glu Thr Ala Leu Lys Phe Leu Tyr Thr Ser Gln
    2750                2755                2760

His Gly Thr Asn Ser Glu Ile Glu Glu Tyr Leu Lys Val Leu Tyr
    2765                2770                2775

Asp Tyr Asp Ile Pro Thr Thr Glu Asn Leu Tyr Phe Gln Ser Gly
    2780                2785                2790

Thr Val Asp Ala Gly Ala Asp Ala Gly Lys Lys Lys Asp Gln Lys
    2795                2800                2805

Asp Asp Lys Val Ala Glu Gln Ala Ser Lys Asp Arg Asp Val Asn
    2810                2815                2820

Ala Gly Thr Ser Gly Thr Phe Ser Val Pro Arg Ile Asn Ala Met
    2825                2830                2835

Ala Thr Lys Leu Gln Tyr Pro Arg Met Arg Gly Glu Val Val Val
    2840                2845                2850

Asn Leu Asn His Leu Leu Gly Tyr Lys Pro Gln Gln Ile Asp Leu
    2855                2860                2865

Ser Asn Ala Arg Ala Thr His Glu Gln Phe Ala Ala Trp His Gln
    2870                2875                2880

Ala Val Met Thr Ala Tyr Gly Val Asn Glu Glu Gln Met Lys Ile
    2885                2890                2895

Leu Leu Asn Gly Phe Met Val Trp Cys Ile Glu Asn Gly Thr Ser
    2900                2905                2910

Pro Asn Leu Asn Gly Thr Trp Val Met Met Asp Gly Glu Asp Gln
    2915                2920                2925

Val Ser Tyr Pro Leu Lys Pro Met Val Glu Asn Ala Gln Pro Thr
    2930                2935                2940

Leu Arg Gln Ile Met Thr His Phe Ser Asp Leu Ala Glu Ala Tyr
    2945                2950                2955

Ile Glu Met Arg Asn Arg Glu Arg Pro Tyr Met Pro Arg Tyr Gly
    2960                2965                2970

Leu Gln Arg Asn Ile Thr Asp Met Ser Leu Ser Arg Tyr Ala Phe
    2975                2980                2985

Asp Phe Tyr Glu Leu Thr Ser Lys Thr Pro Val Arg Ala Arg Glu
```

```
                2990                2995                3000
Ala His Met Gln Met Lys Ala Ala Val Arg Asn Ser Gly Thr
    3005                3010                3015

Arg Leu Phe Gly Leu Asp Gly Asn Val Gly Thr Ala Glu Glu Asp
    3020                3025                3030

Thr Glu Arg His Thr Ala His Asp Val Asn Arg Asn Met His Thr
    3035                3040                3045

Leu Leu Gly Val Arg Gln
    3050

<210> SEQ ID NO 85
<211> LENGTH: 4157
<212> TYPE: DNA
<213> ORGANISM: Homo sapiens

<400> SEQUENCE: 85
agcggggcgg ggcgccagcg ctgccttttc tcctgccggg tagtttcgct ttcctgcgca      60
gagtctgcgg aggggctcgg ctgcaccggg gggatcgcgc ctggcagacc ccagaccgag     120
cagaggcgac ccagcgcgct cgggagaggc tgcaccgccg cgcccccgcc tagcccttcc     180
ggatcctgcg cgcagaaaag tttcatttgc tgtatgccat cctcgagagc tgtctaggtt     240
aacgttcgca ctctgtgtat ataacctcga cagtcttggc acctaacgtg ctgtgcgtag     300
ctgctccttt ggttgaatcc ccaggccctt gttggggcac aaggtggcag gatgtctcag     360
tggtacgaac ttcagcagct tgactcaaaa ttcctggagc aggttcacca gctttatgat     420
gacagttttc ccatggaaat cagacagtac ctggcacagt ggttagaaaa gcaagactgg     480
gagcacgctg ccaatgatgt ttcatttgcc accatccgtt tcatgacct cctgtcacag     540 ctggatgatc aatatagtcg cttttctttg gagaataact tcttgctaca gcataacata     600
aggaaaagca gcgtaatct tcaggataat tttcaggaag acccaatcca gatgtctatg     660
atcatttaca gctgtctgaa ggaagaaagg aaaattctgg aaaacgccca gagatttaat     720
caggctcagt cggggaatat tcagagcaca gtgatgttag acaaacagaa agagcttgac     780
agtaaagtca gaaatgtgaa ggacaaggtt atgtgtatag agcatgaaat caagagcctg     840
gaagatttac aagatgaata tgacttcaaa tgcaaaacct tgcagaacag agaacacgag     900
accaatggtg tggcaaagag tgatcagaaa caagaacagc tgttactcaa gagatgtgat     960
ttaatgcttg acaataagag aaaggaagta gttcacaaaa taatagagtt gctgaatgtc    1020
actgaactta cccagaatgc cctgattaat gatgaactag tggagtggaa gcggagacag    1080
cagagcgcct gtattggggg gccgcccaat gcttgcttgg atcagctgca gaactggttc    1140
actatagttg cggagagtct gcagcaagtt cggcagcagc ttaaaaagtt ggaggaattg    1200
gaacagaaat acacctacga acatgaccct atcacaaaaa acaaacaagt gttatgggac    1260
cgcaccttca gtctttccca gcagctcatt cagagctcgt tgtggtggaa agacagccc    1320 tgcatgccaa cgcaccctca gaggccgctg gtcttgaaga caggggtcca gttcactgtg    1380
aagttgagac tgttggtgaa attgcaagag ctgaattata atttgaaagt caaagtctta    1440
tttgataaag atgtgaatga gagaaataca gtaaaaggat ttaggaagtt caacattttg    1500
ggcacgcaca caaaagtgat gaacatggag gagtccacca atggcagtct ggcggctgaa    1560
tttcggcacc tgcaattgaa agaacagaaa aatgctggca ccagaacgaa tgagggtcct    1620
ctcatcgtta ctgaagagct tcactccctt agttttgaaa cccaattgtg ccagcctggt    1680
ttggtaattg acctcgagac gacctctctg cccgttgtgg tgatctccaa cgtcagccag    1740
```

```
ctcccgagcg gttgggcctc catcctttgg tacaacatgc tggtggcgga acccaggaat    1800
ctgtccttct tcctgactcc accatgtgca cgatgggctc agctttcaga agtgctgagt    1860
tggcagtttt cttctgtcac caaaagaggt ctcaatgtgg accagctgaa catgttggga    1920
gagaagcttc ttggtcctaa cgccagcccc gatggtctca ttccgtggac gaggttttgt    1980
aaggaaaata taaatgataa aaattttccc ttctggcttt ggattgaaag catcctagaa    2040
ctcattaaaa aacacctgct ccctctctgg aatgatgggt gcatcatggg cttcatcagc    2100
aaggagcgag agcgtgccct gttgaaggac cagcagccgg ggaccttcct gctgcggttc    2160
agtgagagct cccgggaagg ggccatcaca ttcacatggg tggagcggtc ccagaacgga    2220
ggcgaacctg acttccatgc ggttgaaccc tacacgaaga agaactttc tgctgttact     2280
ttccctgaca tcattcgcaa ttacaaagtc atggctgctg agaatattcc tgagaatccc    2340
ctgaagtatc tgtatccaaa tattgacaaa gaccatgcct ttggaaagta ttactccagg    2400
ccaaaggaag caccagagcc aatgaacttg atggcccta aaggaactgg atatatcaag     2460
actgagttga tttctgtgtc tgaagttcac ccttctagac ttcagaccac agacaacctg    2520
ctccccatgt ctcctgagga gttgacgag gtgtctcgga gagtgggctc tgtagaattc     2580
gacagtatga tgaacacagt atagagcatg aatttttttc atcttctctg gcgacagttt    2640
tccttctcat ctgtgattcc ctcctgctac tctgttcctt cacatcctgt gtttctaggg    2700
aaatgaaaga aaggccagca aattcgctgc aacctgttga tagcaagtga attttctct     2760
aactcagaaa catcagttac tctgaagggc atcatgcatc ttactgaagg taaaattgaa    2820
aggcattctc tgaagagtgg gtttcacaag tgaaaaacat ccagatacac ccaaagtatc    2880
aggacgagaa tgagggtcct ttgggaaagg agaagttaag caacatctag caaatgttat    2940
gcataaagtc agtgcccaac tgttataggt tgttggataa atcagtggtt atttagggaa    3000
ctgcttgacg taggaacggt aaatttctgt gggagaattc ttacatgttt tctttgcttt    3060
aagtgtaact ggcagttttc cattggttta cctgtgaaat agttcaaagc caagtttata    3120
tacaattata tcagtcctct ttcaaaggta gccatcatgg atctggtagg gggaaaatgt    3180
gtattttatt acatctttca cattggctat ttaaagacaa agacaaattc tgtttcttga    3240
gaagagaata ttagctttac tgtttgttat ggcttaatga cactagctaa tatcaataga    3300
aggatgtaca tttccaaatt cacaagttgt gtttgatatc caaagctgaa tacattctgc    3360
tttcatcttg gtcacataca attatttta cagttctccc aagggagtta ggctattcac      3420
aaccactcat tcaaaagttg aaattaacca tagatgtaga taaactcaga aatttaattc    3480
atgtttctta aatgggctac tttgtccttt ttgttattag ggtggtattt agtctattag    3540
ccacaaaatt gggaaaggag tagaaaaagc agtaactgac aacttgaata atacaccaga    3600
gataatatga gaatcagatc atttcaaaac tcatttccta tgtaactgca ttgagaactg    3660
catatgtttc gctgatatat gtgttttca catttgcgaa tggttccatt ctctctcctg      3720
tacttttcc agacactttt ttgagtggat gatgtttcgt gaagtatact gtattttac       3780
cttttccctt ccttatcact gacacaaaaa gtagattaag agatgggttt gacaaggttc    3840
ttcccttta catactgctg tctatgtggc tgtatcttgt ttttccacta ctgctaccac      3900
aactatatta tcatgcaaat gctgtattct tctttggtgg agataaagat ttcttgagtt    3960
ttgttttaaa attaaagcta agtatctgt attgcattaa atataatatg cacacagtgc      4020
tttccgtggc actgcataca atctgaggcc tcctctctca gtttttatat agatggcgag    4080
aacctaagtt tcagttgatt ttacaattga aatgactaaa aacaaagaa gacaacatta     4140
```

```
aaacaatatt gtttcta                                                  4157

<210> SEQ ID NO 86
<211> LENGTH: 4451
<212> TYPE: DNA
<213> ORGANISM: Homo sapiens

<400> SEQUENCE: 86
gctcatacta gggacgggaa gtcgcgacca gagccattgg agggcgcggg gactgcaacc      60
ctaatcagca gagcccaaat ggcgcagtgg gaaatgctgc agaatcttga cagccccttt     120
caggatcagc tgcaccagct ttactcgcac agcctcctgc ctgtggacat tcgacagtac     180
ttggctgtct ggattgaaga ccagaactgg caggaagctg cacttgggag tgatgattcc     240
aaggctacca tgctattctt ccacttcttg gatcagctga actatgagtg ggccgttgc      300 agccaggacc cagagtcctt gttgctgcag cacaatttgc ggaaattctg ccgggacatt     360 cagcccttt cccaggatcc tacccagttg gctgagatga tctttaacct ccttctggaa      420 gaaaaagaa ttttgatcca ggctcagagg gcccaattgg aacaaggaga gccagttctc      480
gaaacacctg tggagagcca gcaacatgag attgaatccc ggatcctgga tttaagggct     540
atgatggaga agctggtaaa atccatcagc caactgaaag accagcagga tgtcttctgc     600
ttccgatata agatccaggc caaagggaag acaccctctc tggaccccca tcagaccaaa     660
gagcagaaga ttctgcagga aactctcaat gaactggaca aaaggagaaa ggaggtgctg     720
gatgcctcca agcactgct aggccgatta actaccctaa tcgagctact gctgccaaag      780
ttggaggagt ggaaggccca gcagcaaaaa gcctgcatca gagctcccat tgaccacggg     840
ttggaacagc tggagacatg gttcacagct ggagcaaagc tgttgtttca cctgaggcag     900
ctgctgaagg agctgaaggg actgagttgc ctggttagct atcaggatga ccctctgacc     960 aaagggtgg acctacgcaa cgcccaggtc acagagttgc tacagcgtct gctccacaga     1020
gcctttgtgg tagaaaccca gccctgcatg ccccaaactc ccatcgacc cctcatcctc     1080 aagactggca gcaagttcac cgtccgaaca aggctgctgg tgagactcca ggaaggcaat     1140
gagtcactga ctgtggaagt ctccattgac aggaatcctc ctcaattaca aggcttccgg     1200
aagttcaaca ttctgacttc aaaccagaaa actttgaccc ccgagaaggg gcagagtcag     1260
ggtttgattt gggactttgg ttacctgact ctggtggagc aacgttcagg tggttcagga     1320
aagggcagca ataaggggcc actaggtgtg acagaggaac tgcacatcat cagcttcacg     1380
gtcaaatata cctaccaggg tctgaagcag gagctgaaaa cggacaccct ccctgtggtg     1440
attatttcca acatgaacca gctctcaatt gcctgggctt cagttctctg gttcaatttg     1500
ctcagcccaa accttcagaa ccagcagttc ttctccaacc cccccaaggc cccctggagc     1560
ttgctgggcc ctgctctcag ttggcagttc tcctcctatg ttggccgagg cctcaactca     1620
gaccagctga gcatgctgag aaacaagctg ttcgggcaga actgtaggac tgaggatcca     1680
ttattgtcct gggctgactt cactaagcga gagagccctc ctggcaagtt accattctgg     1740
acatggctgg acaaaattct ggagttggta catgaccacc tgaaggatct ctggaatgat     1800
ggacgcatca tgggctttgt gagtcggagc caggagcgcc ggctgctgaa gagaccatg      1860 tctggcacct ttctactgcg cttcagtgaa tcgtcagaag ggggcattac ctgctcctgg     1920
gtggagcacc aggatgatga caaggtgctc atctactctg tgcaaccgta cacgaaggag     1980
gtgctgcagt cactcccgct gactgaaatc atccgccatt accagttgct cactgaggag     2040 aatataccctg aaaacccact gcgcttcctc tatcccccgaa tcccccggga tgaagctttt     2100
```

```
gggtgctact accaggagaa agttaatctc caggaacgga ggaaatacct gaaacacagg      2160
ctcattgtgg tctctaatag acaggtggat gaactgcaac aaccgctgga gcttaagcca      2220
gagccagagc tggagtcatt agagctggaa ctagggctgg tgccagagcc agagctcagc      2280
ctggacttag agccactgct gaaggcaggg ctggatctgg ggccagagct agagtctgtg      2340
ctggagtcca ctctggagcc tgtgatagag cccacactat gcatggtatc acaaacagtg      2400
ccagagccag accaaggacc tgtatcacag ccagtgccag agccagattt gccctgtgat      2460
ctgagacatt tgaacactga gccaatggaa atcttcagaa actgtgtaaa gattgaagaa      2520
atcatgccga atggtgaccc actgttggct ggccagaaca ccgtggatga ggtttacgtc      2580
tcccgcccca gccacttcta cactgatgga cccttgatgc cttctgactt ctaggaacca      2640
catttcctct gttcttttca tatctcttgc ccttcctact cctcatagca tgatattgtt      2700
ctccaaggat gggaatcagg catgtgtccc ttccaagctg tgttaactgt tcaaactcag      2760
gcctgtgtga ctccattggg gtgagaggtg aaagcataac atgggtacag aggggacaac      2820
aatgaatcag aacagatgct gagccatagg tctaaatagg atcctggagg ctgcctgctg      2880
tgctgggagg tataggggtc ctgggggcag gccagggcag ttgacaggta cttggagggc      2940
tcagggcagt ggcttctttc cagtatggaa ggatttcaac attttaatag ttggttaggc      3000
taaactggtg catactggca ttggcccttg gtggggagca cagacacagg ataggactcc      3060
atttctttct tccattcctt catgtctagg ataacttgct ttcttctttc ctttactcct      3120
ggctcaagcc ctgaatttct tcttttcctg caggggttga gagctttctg ccttagccta      3180
ccatgtgaaa ctctaccctg aagaaaggga tggataggaa gtagacctct ttttcttacc      3240
agtctcctcc cctactctgc ccctaagctg gctgtacctg ttcctccccc ataaaatgat      3300
cctgccaatc taatgtgagt gtgaagcttt gcacactagt ttatgctacc tagtctccac      3360
tttctcaatg cttaggagac agatcactcc tggaggctgg ggatggtagg attgctgggg      3420
attttttttt ttttaaacag ggtctcactc tgttgcccag gctagagtgc aatggtgcaa      3480
tcacagctca ctgcagcctc aacctcctgg gttcaagcaa tcctcctacc tcagcctcct      3540
gggtagctag caccatggca tgcgccacca tgccctattt ttttttttta aagacagggt      3600
cttgctatat tgcccaggct ggtcttgaac tgggctcaag tgatcctcac gccttggcct      3660
cccaaagtgc tgggattata ggcatgagcc actgtgcttg ccaggatttt tttttttttt      3720
tttttttgaga tggagtttct ctcttgttgt ccaggctgga gtgcaatggt gtgatctcgg      3780
ctcactgcaa cctccgcctt ccgggttcaa gtgactctcc tgcctcagcc tcccagtag       3840
ctgggattac agatctgcac caccatgccc agctaatttt gtatttttag tagagacggg      3900
gtttctccat gttggtcagg ctggtctcga actcctgacc tcaagtgatc tgtccacctc      3960
ggcctcccag agtgctggga ttacaggcgt gagccactgt tcccagcagg aatttctttt      4020
ttatagtatt ggataaagtt tggtgttttt acagaggaga agcaatgggt cttagctctt      4080
tctctattat gttatcatcc tccctttttt gtacaatatg ttgtttacct gaaaggaagg      4140
tttctattcg ttggttgtgg acctggacaa agtccaagtc tgtggaactt aaaaccttga      4200
aggtctgtca taggactctg gacaatctca caccttagct attcccaggg aaccccaggg      4260
ggcaactgac attgctccaa gatgttctcc tgatgtagct tgagatataa aggaaaggcc      4320
ctgcacaggt ggctgtttct tgtctgttat gtcagaggaa cagtcctgtt cagaaagggg      4380
ctcttctgag cagaaatggc taataaactt tgtgctgatc tggaaaaaaa aaaaaaaaaa      4440
aaaaaaaaaa a                                                          4451
```

<210> SEQ ID NO 87
<211> LENGTH: 9
<212> TYPE: PRT
<213> ORGANISM: Homo sapiens

<400> SEQUENCE: 87

Gly Ser Glu Asn Leu Tyr Phe Gln Leu
            5

<210> SEQ ID NO 88
<211> LENGTH: 27
<212> TYPE: DNA
<213> ORGANISM: homo sapiens

<400> SEQUENCE: 88
tctagaggcc tgatcatccg gtctcac                                       27

<210> SEQ ID NO 89
<211> LENGTH: 29
<212> TYPE: DNA
<213> ORGANISM: homo sapiens

<400> SEQUENCE: 89
tctagatgga aaacagaagt cccggaaac                                     29

<210> SEQ ID NO 90
<211> LENGTH: 2290
<212> TYPE: DNA
<213> ORGANISM: Homo sapiens

<400> SEQUENCE: 90
gaattccgaa tcatgtgcag aatgctgaat cttcccccag ccaggacgaa taagacagcg      60
cggaaaagca gattctcgta attctggaat tgcatgttgc aaggagtctc ctggatcttc     120
gcacccagct tcgggtaggg agggagtccg ggtcccgggc taggccagcc ggcaggtgg      180 agagggtccc cggcagcccc gcgcgcccct ggccatgtct ttaatgccct gccccttcat     240
gtggccttct gagggttccc agggctggcc agggttgttt ccacccgcg cgcgcgctct      300 caccccagc aaacccacc tggcagggct ccctccagcc gagacctttt gattcccggc       360
tcccgcgctc ccgcctccgc gccagcccgg gaggtggccc tggacagccg gacctcgccc    420
ggccccggct gggaccatgg tgtttctctc gggaaatgct tccgacagct ccaactgcac    480
ccaaccgccg gcaccggtga acatttccaa ggccattctg ctcggggtga tcttgggggg    540
cctcattctt ttcggggtgc tgggtaacat cctagtgatc ctctccgtag cctgtcaccg    600
acacctgcac tcagtcacgc actactacat cgtcaacctg gcggtggccg acctcctgct    660
cacctccacg gtgctgccct tctccgccat cttcgaggtc ctaggctact gggccttcgg    720
cagggtcttc tgcaacatct gggcggcagt ggatgtgctg tgctgcaccg cgtccatcat    780
gggcctctgc atcatctcca tcgaccgcta catcggcgtg agctaccgc tgcgctaccc    840 aaccatcgtc acccgagga gggtctcat ggctctgctc tgcgtctggg cactctccct     900
ggtcatatcc attggacccc tgttcggctg gaggcagccg gccccgagg acgagaccat    960 ctgccagatc aacgaggagc cgggctacgt gctcttctca gcgctgggct ccttctacct   1020
gcctctggcc atcatcctgg tcatgtactg ccgcgtctac gtggtggcca agaggagag    1080 ccggggcctc aagtctggcc tcaagaccga caagtcggac tcggagcaag tgacgctccg   1140
catccatcgg aaaacgcccc cggcaggagg cagcgggatg ccagcgcca agaccaagac    1200 gcacttctca gtgaggctcc tcaagttctc ccgggagaag aaagcggcca aacgctggg    1260

-continued

```
catcgtggtc ggctgcttcg tcctctgctg gctgcctttt ttcttagtca tgcccattgg      1320
gtctttcttc cctgatttca agccctctga aacagttttt aaaatagtat tttggctcgg      1380
atatctaaac agctgcatca accccatcat atacccatgc tccagccaag agttcaaaaa      1440
ggcctttcag aatgtcttga gaatccagtg tctccgcaga aagcagtctt ccaaacatgc      1500
cctgggctac accctgcacc cgcccagcca ggccgtggaa gggcaacaca aggacatggt      1560
gcgcatcccc gtgggatcaa gagagacctt ctacaggatc tccaagacgg atggcgtttg      1620
tgaatggaaa ttttctctt ccatgccccg tggatctgcc aggattacag tgtccaaaga      1680
ccaatcctcc tgtaccacag cccgggtgag aagtaaaagc ttttggagg tctgctgctg      1740 tgtagggccc tcaaccccca gccttgacaa gaaccatcaa gttccaacca ttaaggtcca      1800
caccatctcc ctcagtgaga acggggagga agtctaggac aggaaagatg cagaggaaag      1860
gggaataatc ttaggtaccc accccacttc cttctcggaa ggccagctct tcttggagga      1920
caagacagga ccaatcaaag aggggacctg ctgggaatgg ggtgggtggt agacccaact      1980
catcaggcag cgggtagggc acagggaaga gggagggtgt ctcacaacca accagttcag      2040
aatgatacga aacagcattt ccctgcagct aatgctttct tggtcactct gtgcccactt      2100
caacgaaaac caccatggga aacagaattt catgcacaat ccaaaagact ataaatatag      2160
gattatgatt tcatcatgaa tattttgagc acacactcta agtttggagc tatttcttga      2220
tggaagtgag gggatttat tttcaggctc aacctactga cagccacatt tgacatttat      2280
gccggaattc                                                             2290
```

<210> SEQ ID NO 91
<211> LENGTH: 26
<212> TYPE: DNA
<213> ORGANISM: homo sapiens

<400> SEQUENCE: 91

```
ctcggatatc taaacagctg catcaa                                            26
```

<210> SEQ ID NO 92
<211> LENGTH: 29
<212> TYPE: DNA
<213> ORGANISM: homo sapiens

<400> SEQUENCE: 92

```
tctagacttt ctgcagagac actggattc                                         29
```

<210> SEQ ID NO 93
<211> LENGTH: 31
<212> TYPE: DNA
<213> ORGANISM: homo sapiens

<400> SEQUENCE: 93

```
tctagatcga aggcagtgga ggatcttcag g                                      31
```

<210> SEQ ID NO 94
<211> LENGTH: 27
<212> TYPE: DNA
<213> ORGANISM: homo sapiens

<400> SEQUENCE: 94

```
tctagaggcc tgatcatccg gtctcac                                           27
```

<210> SEQ ID NO 95
<211> LENGTH: 23

```
<212> TYPE: DNA
<213> ORGANISM: homo sapiens

<400> SEQUENCE: 95
cggatccgtt ggtactcttg agg                                          23

<210> SEQ ID NO 96
<211> LENGTH: 4989
<212> TYPE: DNA
<213> ORGANISM: homo sapiens

<400> SEQUENCE: 96
tttttttttt ttttgagaaa gggaatttca tcccaaataa aaggaatgaa gtctggctcc    60
ggaggagggt ccccgacctc gctgtggggg ctcctgtttc tctccgccgc gctctcgctc   120
tggccgacga gtggagaaat ctgcgggcca ggcatcgaca tccgcaacga ctatcagcag   180
ctgaagcgcc tggagaactg cacggtgatc gagggctacc tccacatcct gctcatctcc   240
aaggccgagg actaccgcag ctaccgcttc cccaagctca cggtcattac cgagtacttg   300
ctgctgttcc gagtggctgg cctcgagagc ctcggagacc tcttccccaa cctcacggtc   360
atccgcggct ggaaactctt ctacaactac gccctggtca tcttcgagat gaccaatctc   420
aaggatattg ggctttacaa cctgaggaac attactcggg gggccatcag gattgagaaa   480
aatgctgacc tctgttacct ctccactgtg gactggtccc tgatcctgga tgcggtgtcc   540
aataactaca ttgtggggaa taagccccca aaggaatgtg gggacctgtg tccagggacc   600
atggaggaga agccgatgtg tgagaagacc accatcaaca atgagtacaa ctaccgctgc   660
tggaccacaa accgctgcca gaaaatgtgc ccaagcacgt gtgggaagcg ggcgtgcacc   720
gagaacaatg agtgctgcca ccccgagtgc ctgggcagct gcagcgcgcc tgacaacgac   780
acggcctgtg tagcttgccg ccactactac tatgccggtg tctgtgtgcc tgcctgcccg   840
cccaacacct acaggtttga gggctggcgc tgtgtggacc gtgacttctg cgccaacatc   900
ctcagcgccg agagcagcga ctccgagggg tttgtgatcc acgacggcga gtgcatgcag   960
gagtgcccct cgggcttcat ccgcaacggc agccagagca tgtactgcat cccttgtgaa  1020
ggtccttgcc cgaaggtctg tgaggaagaa aagaaaacaa agaccattga ttctgttact  1080
tctgctcaga tgctccaagg atgcaccatc ttcaagggca tttgctcat taacatccga  1140 cgggggaata acattgcttc agagctggag aacttcatgg ggctcatcga ggtggtgacg  1200
ggctacgtga agatccgcca ttctcatgcc ttggtctcct tgtccttcct aaaaaacctt  1260
cgcctcatcc taggagagga gcagctagaa gggaattact ccttctacgt cctcgacaac  1320
cagaacttgc agcaactgtg ggactgggac caccgcaacc tgaccatcaa agcagggaaa  1380
atgtactttg ctttcaatcc caaattatgt gtttccgaaa tttaccgcat ggaggaagtg  1440
acggggacta aagggcgcca aagcaaaggg gacataaaca ccaggaacaa cggggagaga  1500
gcctcctgtg aaagtgacgt cctgcatttc acctccacca ccacgtcgaa gaatcgcatc  1560
atcataacct ggcaccggta ccggcccccc gactacaggg atctcatcag cttcaccgtt  1620
tactacaagg aagcacccct taagaatgtc acagagtatg atgggcagga tgcctgcggc  1680
tccaacagct ggaacatggt ggacgtggac ctcccgccca caaggacgt ggagcccggc   1740 atcttactac atgggctgaa gccctggact cagtacgccg tttacgtcaa ggctgtgacc  1800
ctcaccatgg tggagaacga ccatatccgt ggggccaaga gtgagatctt gtacattcgc  1860
accaatgctt cagttccttc cattcccttg gacgttcttt cagcatcgaa ctcctcttct  1920
cagttaatcg tgaagtggaa ccctccctct ctgcccaacg gcaacctgag ttactacatt  1980
```

```
gtgcgctggc agcggcagcc tcaggacggc tacctttacc ggcacaatta ctgctccaaa    2040
gacaaaatcc ccatcaggaa gtatgccgac ggcaccatcg acattgagga ggtcacagag    2100
aaccccaaga ctgaggtgtg tggtggggag aaagggcctt gctgcgcctg ccccaaaact    2160
gaagccgaga agcaggccga aaggaggag gctgaatacc gcaaagtctt tgagaatttc    2220
ctgcacaact ccatcttcgt gcccagacct gaaaggaagc ggagagatgt catgcaagtg    2280
gccaacacca ccatgtccag ccgaagcagg aacaccacgg ccgcagacac ctacaacatc    2340
accgacccgg aagagctgga gacagagtac cctttctttg agagcagagt ggataacaag    2400
gagagaactg tcatttctaa ccttcggcct ttcacattgt accgcatcga tatccacagc    2460
tgcaaccacg aggctgagaa gctgggctgc agcgcctcca acttcgtctt tgcaaggact    2520
atgcccgcag aaggagcaga tgacattcct gggccagtga cctgggagcc aaggcctgaa    2580
aactccatct ttttaaagtg gccggaacct gagaatccca atggattgat tctaatgtat    2640
gaaataaaat acgatcaca agttgaggat cagcgagaat gtgtgtccag acaggaatac    2700
aggaagtatg gaggggccaa gctaaaccgg ctaaacccgg ggaactacac agcccggatt    2760
caggccacat ctctctctgg gaatgggtcg tggacagatc ctgtgttctt ctatgtccag    2820
gccaaaacag gatatgaaaa cttcatccat ctgatcatcg ctctgcccgt cgctgtcctg    2880
ttgatcgtgg gagggttggt gattatgctg tacgtcttcc atagaaagag aaataacagc    2940
aggctgggga atggagtgct gtatgcctct gtgaacccgg agtacttcag cgctgctgat    3000
gtgtacgttc ctgatgagtg ggaggtggct cgggagaaga tcaccatgag ccgggaactt    3060
gggcaggggt cgtttgggat ggtctatgaa ggagttgcca agggtgtggt gaaagatgaa    3120
cctgaaacca gagtggccat taaaacagtg aacgaggccg caagcatgcg tgagaggatt    3180
gagtttctca acgaagcttc tgtgatgaag gagttcaatt gtcaccatgt ggtgcgattg    3240
ctgggtgtgg tgtcccaagg ccagccaaca ctggtcatca tggaactgat gacacggggc    3300
gatctcaaaa gttatctccg gtctctgagg ccagaaatgg agaataatcc agtcctagca    3360
cctccaagcc tgagcaagat gattcagatg gccggagaga ttgcagacgg catggcatac    3420
ctcaacgcca ataagttcgt ccacagagac cttgctgccc ggaattgcat ggtagccgaa    3480
gatttcacag tcaaaatcgg agattttggt atgacgcgag atatctatga cagactat    3540 taccggaaag gaggcaaagg gctgctgccc gtgcgctgga tgtctcctga gtccctcaag    3600
gatggagtct tcaccactta ctcggacgtc tggtccttcg gggtcgtcct ctgggagatc    3660
gccacactgg ccgagcagcc ctaccaggc ttgtccaacg agcaagtcct tcgcttcgtc    3720
atggagggcg gccttctgga caagccagac aactgtcctg acatgctgtt tgaactgatg    3780
cgcatgtgct ggcagtataa ccccaagatg aggccttcct tcctggagat catcagcagc    3840
atcaaagagg agatggagcc tggcttccgg gaggtctcct tctactacag cgaggagaac    3900
aagctgcccg agcggagga gctggacctg agccagaga acatggagag cgtccccctg    3960
gacccctcgg cctcctcgtc ctccctgcca ctgcccgaca cactcagg acacaaggcc    4020 gagaacggcc ccggccctgg ggtgctgtc ctccgcgcca gcttcgacga gagacagcct    4080
tacgcccaca tgaacggggg ccgcaagaac gagcgggcct tgccgctgcc ccagtcttcg    4140
acctgctgat ccttggatcc tgaatctgtg caaacagtaa cgtgtgcgca cgcgcagcgg    4200 ggtgggggg gagagagagt tttaacaatc cattcacaag cctcctgtac ctcagtggat    4260
cttcagttct gcccttgctg cccgcgggag acagcttctc tgcagtaaaa cacatttggg    4320
atgttccttt tttcaatatg caagcagctt tttattccct gcccaaaccc ttaactgaca    4380
```

| | |
|---|---|
| tgggccttta agaaccttaa tgacaacact taatagcaac agagcacttg agaaccagtc | 4440 |
| tcctcactct gtccctgtcc ttccctgttc tccctttctc tctcctctct gcttcataac | 4500 |
| ggaaaaataa ttgccacaag tccagctggg aagccctttt tatcagtttg aggaagtggc | 4560 |
| tgtccctgtg gccccatcca accactgtac acacccgcct gacaccgtgg gtcattacaa | 4620 |
| aaaaacacgt ggagatggaa attttttacct ttatctttca cctttctagg gacatgaaat | 4680 |
| ttacaaaggg ccatcgttca tccaaggctg ttaccatttt aacgctgcct aattttgcca | 4740 |
| aaatcctgaa ctttctccct catcggcccg gcgctgattc ctcgtgtccg gaggcatggg | 4800 |
| tgagcatggc agctggttgc tccatttgag agacacgctg gcgacacact ccgtccatcc | 4860 |
| gactgcccct gctgtgctgc tcaaggccac aggcacacag gtctcattgc ttctgactag | 4920 |
| attattattt gggggaactg gacacaatag gtctttctct cagtgaaggt ggggagaagc | 4980 |
| tgaaccggc | 4989 |

<210> SEQ ID NO 97
<211> LENGTH: 3076
<212> TYPE: DNA
<213> ORGANISM: homo sapiens

<400> SEQUENCE: 97

| | |
|---|---|
| gtttctccag ggaggcaggg cccggggaga agttggagc ggtaacctaa gctggcagtg | 60 |
| gcgtgatccg gcaccaaatc ggcccgcggt gcggtgcgga gactccatga ggccctggac | 120 |
| atgaacaagc tgagtggagg cggcgggcgc aggactcggg tggaagggg ccagcttggg | 180 |
| ggcgaggagt ggacccgcca cgggagcttt gtcaataagc ccacgcgggg ctggctgcat | 240 |
| cccaacgaca aagtcatggg acccggggtt tcctacttgg ttcggtacat gggttgtgtg | 300 |
| gaggtcctcc agtcaatgcg tgccctggac ttcaacaccc ggactcaggt caccagggag | 360 |
| gccatcagtc tggtgtgtga ggctgtgccg ggtgctaagg gggcgacaag gaggagaaag | 420 |
| ccctgtagcc gcccgctcag ctctatcctg gggaggagta acctgaaatt tgctggaatg | 480 |
| ccaatcactc tcaccgtctc caccagcagc ctcaacctca tggccgcaga ctgcaaacag | 540 |
| atcatcgcca accaccacat gcaatctatc tcatttgcat ccggcgggga tccggacaca | 600 |
| gccgagtatg tcgcctatgt tgccaaagac cctgtgaatc agagagcctg ccacattctg | 660 |
| gagtgtcccg aagggcttgc ccaggatgtc atcagcacca ttggccaggc cttcgagttg | 720 |
| cgcttcaaac aataccctcag gaacccaccc aaactggtca cccctcatga caggatggct | 780 |
| ggctttgatg gctcagcatg ggatgaggag gaggaagagc cacctgacca tcagtactat | 840 |
| aatgacttcc cggggaagga accccccttg gggggggtgg tagacatgag gcttcgggaa | 900 |
| ggagccgctc caggggctgc tcgacccact gcacccaatg cccagacccc cagccacttg | 960 |
| ggagctacat tgcctgtagg acagcctgtt ggggagatc cagaagtccg caaacagatg | 1020 |
| ccacctccac caccctgtcc agcaggcaga gagcttttttg atgatccctc ctatgtcaac | 1080 |
| gtccagaacc tagacaaggc ccggcaagca gtgggtggtg ctgggccccc caatcctgct | 1140 |
| atcaatggca gtgcaccccg ggacctgttt gacatgaagc ccttcgaaga tgctcttcgc | 1200 |
| gtgcctccac ctcccagtc ggtgtccatg gctgagcagc tccgagggga gccctggttc | 1260 |
| catgggaagc tgagccggcg ggaggctgag gcactgctgc agctcaatgg ggacttcctg | 1320 |
| gtacgggaga gcacgaccac acctggccag tatgtgctca ctggcttgca gagtgggcag | 1380 |
| cctaagcatt tgctactggt ggaccctgag ggtgtggttc ggactaagga tcaccgcttt | 1440 |
| gaaagtgtca gtcaccttat cagctaccac atggacaatc acttgcccat catctctgcg | 1500 |

```
ggcagcgaac tgtgtctaca gcaacctgtg gagcggaaac tgtgatctgc cctagcgctc      1560
tcttccagaa gatgccctcc aatcctttcc accctattcc ctaactctcg ggacctcgtt      1620
tgggagtgtt ctgtgggctt ggccttgtgt cagagctggg agtagcatgg actctgggtt      1680
tcatatccag ctgagtgaga gggtttgagt caaaagcctg ggtgagaatc ctgcctctcc      1740
ccaaacatta atcaccaaag tattaatgta cagagtggcc cctcacctgg gccttttcctg     1800 tgccaacctg atgcccttc cccaagaagg tgagtgcttg tcatggaaaa tgtcctgtgg       1860
tgacaggccc agtggaacag tcacccttct gggcaagggg gaacaaatca cacctctggg      1920
cttcagggta tcccagaccc ctctcaacac ccgccccccc catgtttaaa ctttgtgcct      1980
ttgaccatct cttaggtcta atgatatttt atgcaaacag ttcttggacc cctgaattca      2040
atgacaggga tgccaacacc ttcttggctt ctggacctg tgttcttgct gagcaccctc       2100
tccggtttgg gttgggataa cagaggcagg agtggcagct gtccctctc cctggggata      2160 tgcaacccttt agagattgcc ccagagcccc actcccggcc aggcgggaga tggacccctc    2220
ccttgctcag tgcctcctgg ccggggcccc tcaccccaag gggtctgtat atacatttca     2280
taaggcctgc cctcccatgt tgcatgccta tgtactctac gccaaagtgc agcccttcct     2340
cctgaagcct ctgccctgcc tccctttctg ggagggcggg gtgggggtga ctgaatttgg     2400
gcctcttgta cagttaactc tcccaggtgg attttgtgga ggtgagaaaa ggggcattga     2460
gactataaag cagtagacaa tccccacata ccatctgtag agttggaact gcattctttt    2520
aaagttttat atgcatatat tttagggctg tagacttact ttcctatttt cttttccatt    2580
gcttattctt gagcacaaaa tgataatcaa ttattacatt tatacatcac ctttttgact   2640
tttccaagcc ctttacagc tcttggcatt ttcctcgcct aggcctgtga ggtaactggg    2700
atcgcacctt ttataccaga gacctgaggc agatgaaatt tatttccatc taggactaga    2760
aaaacttggg tctcttaccg cgagactgag aggcagaagt cagcccgaat gcctgtcagt    2820
ttcatggagg ggaaacgcaa aacctgcagt tcctgagtac cttctacagg cccggcccag    2880
cctaggcccg gggtggccac accacagcaa gccggccccc cctcttttgg ccttgtggat    2940
aagggagagt tgaccgtttt catcctggcc tccttttgct gtttggatgt ttccacgggt    3000
ctcacttata ccaaagggaa aactcttcat taaagtccgt atttcttcta aaaaaaaaa     3060 aaaaaaaaaa aaaaaa                                                     3076
```

<210> SEQ ID NO 98
<211> LENGTH: 4
<212> TYPE: PRT
<213> ORGANISM: homo sapiens

<400> SEQUENCE: 98

Asn Ser Gly Ser
1

<210> SEQ ID NO 99
<211> LENGTH: 2261
<212> TYPE: DNA
<213> ORGANISM: homo sapiens

<400> SEQUENCE: 99

```
gaaatcaggc tccgggccgg ccgaagggcg caactttccc ccctcggcgc cccaccggct       60
cccgcgcgcc tcccctcgcg cccgagcttc gagccaagca gcgtcctggg gagcgcgtca      120
tggccttacc agtgaccgcc ttgctcctgc cgctggcctt gctgctccac gccgccaggc      180
```

```
cgagccagtt ccgggtgtcg ccgctggatc ggacctggaa cctgggcgag acagtggagc      240
tgaagtgcca ggtgctgctg tccaacccga cgtcgggctg ctcgtggctc ttccagccgc      300
gcggcgccgc cgccagtccc accttcctcc tatacctctc ccaaaacaag cccaaggcgg      360
ccgaggggct ggacacccag cggttctcgg caagaggtt gggggacacc ttcgtcctca      420
ccctgagcga cttccgccga gagaacgagg gctactattt ctgctcggcc ctgagcaact      480
ccatcatgta cttcagccac ttcgtgccgg tcttcctgcc agcgaagccc accacgacgc      540
cagcgccgcg accaccaaca ccggcgccca ccatcgcgtc gcagcccctg tccctgcgcc      600
cagaggcgtg ccgccagcg gcgggggggcg cagtgcacac gaggggggctg gacttcgcct      660 gtgatatcta catctgggcg cccttggccg ggacttgtgg ggtccttctc ctgtcactgg      720
ttatcaccct ttactgcaac cacaggaacc gaagacgtgt ttgcaaatgt cccccggcctg     780 tggtcaaatc gggagacaag cccagccttt cggcgagata cgtctaaccc tgtgcaacag      840
ccactacatt acttcaaact gagatccttc cttttgaggg agcaagtcct ccctttcat      900 ttttcccagt cttcctccct gtgtattcat tctcatgatt attatttag tggggcggg       960 gtgggaaaga ttactttttc tttatgtgtt tgacggaaa caaaactagg taaaatctac     1020
agtacaccac aagggtcaca atactgttgt gcgcacatcg cggtagggcg tggaaagggg     1080
caggccagag ctacccgcag agttctcaga atcatgctga gagagctgga ggcacccatg     1140
ccatctcaac ctcttccccg cccgttttac aaaggggggag gctaaagccc agagacagct     1200
tgatcaaagg cacacagcaa gtcagggttg gagcagtagc tggagggacc ttgtctccca     1260
gctcagggct ctttcctcca caccattcag gtctttcttt ccgaggcccc tgtctcaggg     1320
tgaggtgctt gagtctccaa cggcaaggga acaagtactt cttgatacct gggatactgt     1380
gcccagagcc tcgaggaggt aatgaattaa agaagagaac tgcctttggc agagttctat     1440
aatgtaaaca atatcagact tttttttttt ataatcaagc ctaaaattgt atagacctaa     1500
aataaaatga agtggtgagc ttaaccctgg aaaatgaatc cctctatctc taaagaaaat     1560
ctctgtgaaa cccctatgtg gaggcggaat tgctctccca gcccttgcat tgcagagggg     1620
cccatgaaag aggacaggct accccttttac aaatagaatt tgagcatcag tgaggttaaa     1680
ctaaggccct cttgaatctc tgaatttgag atacaaacat gttcctggga tcactgatga     1740 cttttttatac tttgtaaaga caattgttgg agagccccct cacacagccct ggcctctgct     1800 caactagcag atacagggat gaggcagacc tgactctctt aaggaggctg agagcccaaa     1860
ctgctgtccc aaacatgcac ttccttgctt aaggtatggt acaagcaatg cctgcccatt     1920
ggagagaaaa aacttaagta gataaggaaa taagaaccac tcataattct tcaccttagg     1980
aataatctcc tgttaatatg gtgtacattc ttcctgatta ttttctacac atacatgtaa     2040
aatatgtctt tctttttttaa atagggttgt actatgctgt tatgagtggc tttaatgaat     2100
aaacatttgt agcatcctct ttaatgggta aacagcaaaa aaaaaaaaaa aaaaaaaaa      2160 aaaaaaaaaa aaaaaaaaaa aaaaaaaaaa aaaaaaaaaa aaaaaaaaaa aaaaaaaaaa     2220
aaaaaaaaaa aaaaaaaaaa aaaaaaaaaa aaaaaaaaa a                          2261

<210> SEQ ID NO 100
<211> LENGTH: 6450
<212> TYPE: DNA
<213> ORGANISM: homo sapiens

<400> SEQUENCE: 100
gagttgtgcc tggagtgatg tttaagccaa tgtcagggca aggcaacagt ccctggccgt       60
```

```
cctccagcac ctttgtaatg catatgagct cgggagacca gtacttaaag ttggaggccc    120
gggagcccag gagctggcgg agggcgttcg tcctgggagc tgcacttgct ccgtcgggtc    180
gccggcttca ccggaccgca ggctcccggg gcagggccgg ggccagagct cgcgtgtcgg    240
cgggacatgc gctgcgtcgc ctctaacctc gggctgtgct cttttccag gtggcccgcc     300 ggtttctgag ccttctgccc tgcggggaca cggtctgcac cctgcccgcg gccacggacc    360
atgaccatga ccctccacac caaagcatct gggatggccc tactgcatca gatccaaggg    420
aacgagctgg agcccctgaa ccgtccgcag ctcaagatcc ccctggagcg gccccctgggc   480 gaggtgtacc tggacagcag caagcccgcc gtgtacaact accccgaggg cgccgcctac    540
gagttcaacg ccgcggccgc cgccaacgcg caggtctacg gtcagaccgg cctcccctac    600
ggccccgggt ctgaggctgc ggcgttcggc tccaacggcc tgggggttt cccccccactc    660 aacagcgtgt ctccgagccc gctgatgcta ctgcacccgc cgccgcagct gtcgcctttc    720
ctgcagcccc acggccagca ggtgccctac tacctggaga cgagcccag cggctacacg     780 gtgcgcgagg ccggcccgcc ggcattctac aggccaaatt cagataatcg acgccagggt    840
ggcagagaaa gattggccag taccaatgac aagggaagta tggctatgga atctgccaag    900
gagactcgct actgtgcagt gtgcaatgac tatgcttcag gctaccatta tggagtctgg    960
tcctgtgagg gctgcaaggc cttcttcaag agaagtattc aaggacataa cgactatatg   1020
tgtccagcca ccaaccagtg caccattgat aaaaacagga ggaagagctg ccaggcctgc   1080
cggctccgca aatgctacga agtgggaatg atgaaaggtg ggatacgaaa agaccgaaga   1140
ggagggagaa tgttgaaaca caagcgccag agagatgatg gggagggcag gggtgaagtg   1200
gggtctgctg gagacatgag agctgccaac ctttggccaa gccgctcat gatcaaacgc    1260 tctaagaaga acagcctggc cttgtccctg acggccgacc agatggtcag tgccttgttg   1320
gatgctgagc cccccatact ctattccgag tatgatccta ccagacccct tcagtgaagct   1380 tcgatgatgg gcttactgac caacctggca gacagggagc tggttcacat gatcaactgg   1440
gcgaagaggg tgccaggctt tgtggatttg accctccatg atcaggtcca ccttctagaa   1500
tgtgcctggc tagagatcct gatgattggt ctcgtctggc gctccatgga gcacccagtg   1560
aagctactgt ttgctcctaa cttgctcttg gacaggaacc agggaaaatg tgtagagggc   1620
atggtggaga tcttcgacat gctgctggct acatcatctc ggttccgcat gatgaatctg   1680
cagggagagg agtttgtgtg cctcaaatct attattttgc ttaattctgg agtgtacaca   1740
tttctgtcca gcaccctgaa gtctctgaa gagaaggacc atatccaccg agtcctggac    1800
aagatcacag acactttgat ccacctgatg gccaaggcag gcctgaccct gcagcagcag   1860
caccagcggc tggcccagct cctcctcatc ctctcccaca tcaggcacat gagtaacaaa   1920
ggcatggagc atctgtacag catgaagtgc aagaacgtgg tgccctcta tgacctgctg   1980 ctggagatgc tggacgccca ccgcctacat gcgcccacta gccgtggagg ggcatccgtg   2040
gaggagacgg accaaagcca cttggccact gcgggctcta cttcatcgca ttccttgcaa   2100
aagtattaca tcacggggga ggcagagggt ttccctgcca cagtctgaga gctccctggc   2160
tcccacacgg ttcagataat ccctgctgca ttttaccctc atcatgcacc actttagcca   2220
aattctgtct cctgcataca ctccggcatg catccaacac caatggcttt ctagatgagt   2280
ggccattcat ttgcttgctc agttcttagt ggcacatctt ctgtcttctg ttgggaacag   2340
ccaaagggat tccaaggcta aatctttgta acagctctct ttccccttg ctatgttact    2400 aagcgtgagg attcccgtag ctcttcacag ctgaactcag tctatgggtt ggggctcaga   2460
```

```
taactctgtg catttaagct acttgtagag acccaggcct ggagagtaga catttttgcct    2520
ctgataagca cttttttaaat ggctctaaga ataagccaca gcaaagaatt taaagtggct    2580
cctttaattg gtgacttgga gaaagctagg tcaagggttt attatagcac cctcttgtat    2640
tcctatggca atgcatcctt ttatgaaagt ggtacaccctt aaagctttta tatgactgta    2700
gcagagtatc tggtgattgt caattcactt cccctatag gaatacaagg ggccacacag     2760
ggaaggcaga tccctagtt ggccaagact tatttaact tgatacactg cagattcaga      2820
gtgtcctgaa gctctgcctc tggctttccg gtcatgggtt ccagttaatt catgcctccc    2880
atggacctat ggagagcaac aagttgatct tagttaagtc tccctatatg agggataagt    2940
tcctgatttt tgttttttatt tttgtgttac aaaagaaagc cctccctccc tgaacttgca   3000
gtaaggtcag cttcaggacc tgttccagtg ggcactgtac ttggatcttc ccggcgtgtg    3060
tgtgccttac acaggggtga actgttcact gtggtgatgc atgatgaggg taaatggtag    3120
ttgaaaggag caggggccct ggtgttgcat ttagccctgg ggcatggagc tgaacagtac    3180
ttgtgcagga ttgttgtggc tactagagaa caagagggaa agtagggcag aaactggata    3240
cagttctgag cacagccaga cttgctcagg tggccctgca caggctgcag ctacctagga    3300
acattccttg cagaccccgc attgcctttg ggggtgccct gggatccctg gggtagtcca    3360
gctcttattc atttcccagc gtggcccctgg ttggaagaag cagctgtcaa gttgtagaca   3420
gctgtgttcc tacaattggc ccagcaccct ggggcacggg agaagggtgg ggaccgttgc    3480
tgtcactact caggctgact ggggcctggt cagattacgt atgcccttgg tggtttagag    3540
ataatccaaa atcagggttt ggtttgggga agaaaatcct ccccccttcct cccccgcccc   3600
gttccctacc gcctccactc ctgccagctc atttccttca atttcctttg acctataggc    3660
taaaaaagaa aggctcattc cagccacagg gcagccttcc ctgggccttt gcttctctag    3720
cacaattatg ggttacttcc tttttcttaa caaaaaagaa tgtttgattt cctctgggtg    3780
accttattgt ctgtaattga aaccctattg agaggtgatg tctgtgttag ccaatgaccc    3840
aggtagctgc tcgggcttct cttggtatgt cttgtttgga aaagtggatt tcattcattt    3900
ctgattgtcc agttaagtga tcaccaaagg actgagaatc tgggagggca aaaaaaaaa    3960
aaaaagtttt tatgtgcact taaatttggg gacaattttta tgtatctgtg ttaaggatat   4020
gcttaagaac ataattcttt tgttgctgtt tgtttaagaa gcaccttagt ttgtttaaga    4080
agcaccttat atagtataat atatattttt ttgaaattac attgcttgtt tatcagacaa    4140
ttgaatgtag taattctgtt ctggatttaa tttgactggg ttaacatgca aaaaccaagg    4200
aaaaatattt agttttttttt tttttttttg tatactttttc aagctacctt gtcatgtata   4260
cagtcattta tgcctaaagc ctggtgatta ttcatttaaa tgaagatcac atttcatatc    4320
aactttgta tccacagtag acaaaatagc actaatccag atgcctattg ttggatattg     4380
aatgacagac aatcttatgt agcaaagatt atgcctgaaa aggaaaatta ttcagggcag    4440
ctaattttgc ttttaccaaa atatcagtag taatattttt ggacagtagc taatgggtca    4500
gtgggttctt tttaatgttt atacttagat tttcttttaa aaaattaaa ataaaacaaa     4560
aaaaatttct aggactagac gatgtaatac cagctaaagc caaacaatta tacagtggaa    4620
ggttttacat tattcatcca atgtgttttct attcatgtta agatactact acatttgaag    4680
tgggcagaga acatcagatg attgaaatgt tcgcccaggg gtctccagca actttggaaa    4740
tctcttttgta ttttttacttg aagtgccact aatggacagc agatatttttc tggctgatgt   4800
tggtattggg tgtaggaaca tgatttaaaa aaaaaactct tgcctctgct ttcccccact    4860
```

```
ctgaggcaag ttaaaatgta aaagatgtga tttatctggg gggctcaggt atggtgggga    4920
agtggattca ggaatctggg gaatggcaaa tatattaaga agagtattga aagtatttgg    4980
aggaaaatgg ttaattctgg gtgtgcacca aggttcagta gagtccactt ctgccctgga    5040
gaccacaaat caactagctc catttacagc catttctaaa atggcagctt cagttctaga    5100
gaagaaagaa caacatcagc agtaaagtcc atggaatagc tagtggtctg tgtttctttt    5160
cgccattgcc tagcttgccg taatgattct ataatgccat catgcagcaa ttatgagagg    5220
ctaggtcatc caaagagaag accctatcaa tgtaggttgc aaaatctaac ccctaaggaa    5280
gtgcagtctt tgatttgatt tccctagtaa ccttgcagat atgtttaacc aagccatagc    5340
ccatgccttt tgagggctga acaaataagg gacttactga taatttactt ttgatcacat    5400
taaggtgttc tcaccttgaa atcttataca ctgaaatggc cattgattta ggccactggc    5460
ttagagtact ccttcccctg catgacactg attacaaata ctttcctatt catactttcc    5520
aattatgaga tggactgtgg gtactgggag tgatcactaa caccatagta atgtctaata    5580
ttcacaggca gatctgcttg gggaagctag ttatgtgaaa ggcaaataaa gtcatacagt    5640
agctcaaaag gcaaccataa ttctctttgg tgcaagtctt gggagcgtga tctagattac    5700
actgcaccat tcccaagtta atcccctgaa aacttactct caactggagc aaatgaactt    5760
tggtcccaaa tatccatctt ttcagtagcg ttaattatgc tctgtttcca actgcatttc    5820
ctttccaatt gaattaaagt gtggcctcgt ttttagtcat ttaaaattgt tttctaagta    5880
attgctgcct ctattatggc acttcaattt tgcactgtct tttgagattc aagaaaaatt    5940
tctattcatt tttttgcatc caattgtgcc tgaactttta aaatatgtaa atgctgccat    6000
gttccaaacc catcgtcagt gtgtgtgttt agagctgtgc accctagaaa caacatactt    6060
gtcccatgag caggtgcctg agacacagac ccctttgcat tcacagagag gtcattggtt    6120
atagagactt gaattaataa gtgacattat gccagtttct gttctctcac aggtgataaa    6180
caatgctttt tgtgcactac atactcttca gtgtagagct cttgttttat gggaaaaggc    6240
tcaaatgcca aattgtgttt gatggattaa tatgcccttt tgccgatgca tactattact    6300
gatgtgactc ggttttgtcg cagctttgct ttgtttaatg aaacacactt gtaaacctct    6360
tttgcacttt gaaaagaat ccagcgggat gctcgagcac ctgtaaacaa ttttctcaac    6420
ctatttgatg ttcaaataaa gaattaaact                                    6450

<210> SEQ ID NO 101
<211> LENGTH: 2011
<212> TYPE: DNA
<213> ORGANISM: homo sapiens

<400> SEQUENCE: 101
tttcagtttc tccagctgct ggcttttttgg acacccactc ccccgccagg aggcagttgc      60
aagcgcggag gctgcgagaa ataactgcct cttgaaactt gcagggcgaa gagcaggcgg     120
cgagcgctgg gccggggagg gaccacccga gctgcgacgg gctctggggc tgcggggcag     180
ggctggcgcc cggagcctga gctgcaggag gtgcgctcgc tttcctcaac aggtggcggc     240
ggggcgcgcg ccgggagacc cccctaatg cgggaaaagc acgtgtccgc attttagaga     300
aggcaaggcc ggtgtgttta tctgcaagcc attatacttg cccacgaatc tttgagaaca     360
ttataatgac ctttgtgcct cttcttgcaa ggtgttttct cagctgttat ctcaagacat     420
ggatataaaa aactcaccat ctagccttaa ttctccttcc tcctacaact gcagtcaatc     480
catcttaccc ctggagcacg gctccatata catacccttcc tcctatgtag acagccacca     540
```

```
tgaatatcca gccatgacat tctatagccc tgctgtgatg aattacagca ttcccagcaa    600
tgtcactaac ttggaaggtg ggcctggtcg gcagaccaca agcccaaatg tgttgtggcc    660
aacacctggg cacctttctc ctttagtggt ccatcgccag ttatcacatc tgtatgcgga    720
acctcaaaag agtccctggt gtgaagcaag atcgctagaa cacaccttac ctgtaaacag    780
agagacactg aaaaggaagg ttagtgggaa ccgttgcgcc agccctgtta ctggtccagg    840
ttcaaagagg gatgctcact tctgcgctgt ctgcagcgat tacgcatcgg gatatcacta    900
tggagtctgg tcgtgtgaag gatgtaaggc cttttttaaa agaagcattc aaggacataa    960
tgattatatt tgtccagcta caaatcagtg tacaatcgat aaaaaccggc gcaagagctg   1020
ccaggcctgc cgacttcgga agtgttacga agtgggaatg gtgaagtgtg gctcccggag   1080
agagagatgt gggtaccgcc ttgtgcggag acagagaagt gccgacgagc agctgcactg   1140
tgccggcaag gccaagagaa gtggcggcca cgcgccccga gtgcgggagc tgctgctgga   1200
cgccctgagc cccgagcagc tagtgctcac cctcctggag gctgagccgc cccatgtgct   1260
gatcagccgc cccagtgcgc ccttcaccga ggcctccatg atgatgtccc tgaccaagtt   1320
ggccgacaag gagttggtac acatgatcag ctgggccaag aagattcccg gctttgtgga   1380
gctcagcctg ttcgaccaag tgcggctctt ggagagctgt tggatggagg tgttaatgat   1440
ggggctgatg tggcgctcaa ttgaccaccc cggcaagctc atctttgctc cagatcttgt   1500
tctggacagg gatgagggga aatgcgtaga aggaattctg gaaatctttg acatgctcct   1560
ggcaactact tcaaggtttc gagagttaaa actccaacac aaagaatatc tctgtgtcaa   1620
ggccatgatc ctgctcaatt ccagtatgta ccctctggtc acagcgaccc aggatgctga   1680
cagcagccgg aagctggctc acttgctgaa cgccgtgacc gatgctttgg tttgggtgat   1740
tgccaagagc ggcatctcct cccagcagca atccatgcgc ctggctaacc tcctgatgct   1800
cctgtcccac gtcaggcatg cgagtaacaa gggcatggaa catctgctca acatgaagtg   1860
caaaaatgtg gtcccagtgt atgacctgct gctggagatg ctgaatgccc acgtgcttcg   1920
cgggtgcaag tcctccatca cggggtccga gtgcagcccg gcagaggaca gtaaaagcaa   1980
agagggctcc cagaacccac agtctcagtg a                                  2011
```

METHOD FOR ASSAYING PROTEIN-PROTEIN INTERACTION

RELATED APPLICATIONS

This is a divisional application of application Ser. No. 10/888,313 filed Jul. 9, 2004, now U.S. Pat. No. 7,049,076, which claims the benefit of priority under 35 U.S.C. §119(e) to Application No. 60/566,113 filed Apr. 27, 2004, Application No. 60/511,918 filed Oct. 15, 2003, Application No. 60/485,968 filed Jul. 9, 2003, each of which are incorporated by reference in its entirety.

FIELD OF THE INVENTION

This invention relates to methods for determining interaction between molecules of interest. More particularly, it relates to determining if a particular substance referred to as the test compound modulates the interaction of two or more specific proteins of interest, via determining activation of a reporter gene in a cell, where the activation, or lack thereof, results from the modulation or its absence. The determination occurs using transformed or transfected cells, which are also a feature of the invention, as are the agents used to transform or transfect them.

BACKGROUND AND RELATED ART

The study of protein/protein interaction, as exemplified, e.g., by the identification of ligands for receptors, is an area of great interest. Even when a ligand or ligands for a given receptor are known, there is interest in identifying more effective or more selective ligands. GPCRs will be discussed herein as a non-exclusive example of a class of proteins which can be studied in this way.

The G-protein coupled receptors, or "GPCRs" hereafter, are the largest class of cell surface receptors known for humans. Among the ligands recognized by GPCRs are hormones, neurotransmitters, peptides, glycoproteins, lipids, nucleotides, and ions. They also act as receptors for light, odors, pheromones, and taste. Given these various roles, it is perhaps not surprising that they are the subject of intense research, seeking to identify drugs useful in various conditions. The success rate has been phenomenal. Indeed, Howard, et al., *Trends Pharmacol. Sci.*, 22:132-140 (2001) estimate that over 50% of marketed drugs act on such receptors. "GPCRs" as used herein, refers to any member of the GPCR superfamily of receptors characterized by a seven-transmembrane domain (7TM) structure. Examples of these receptors include, but are not limited to, the class A or "rhodopsin-like" receptors; the class B or "secretin-like" receptors; the class C or "metabotropic glutamate-like" receptors; the Frizzled and Smoothened-related receptors; the adhesion receptor family or EGF-7TM/LNB-7TM receptors; adiponectin receptors and related receptors; and chemosensory receptors including odorant, taste, vomeronasal and pheromone receptors. As examples, the GPCR superfamily in humans includes but is not limited to those receptor molecules described by Vassilatis, et al., *Proc. Natl. Acad. Sci. USA*, 100:4903-4908 (2003); Takeda, et al., *FEBS Letters*, 520:97-101 (2002); Fredricksson, et al., *Mol. Pharmacol.*, 63:1256-1272 (2003); Glusman, et al., *Genome Res.*, 11:685-702 (2001); and Zozulya, et al., *Genome Biol.*, 2:0018.1-0018.12 (2001), all of which are incorporated by reference.

The mechanisms of action by which GPCRs function has been explicated to some degree. In brief, when a GPCR binds a ligand, a conformational change results, stimulating a cascade of reactions leading to a change in cell physiology. It is thought that GPCRs transduce signals by modulating the activity of intracellular, heterotrimeric guanine nucleotide binding proteins, or "G proteins". The complex of ligand and receptor stimulates guanine nucleotide exchange and dissociation of the G protein heterotrimer into α and βγ subunits.

Both the GTP-bound α subunit and the βγ dimer can act to regulate various cellular effector proteins, including adenylyl cyclase and phospholipase C (PLC). In conventional cell based assays for GPCRs, receptor activity is monitored by measuring the output of a G-protein regulated effector pathway, such as the accumulation of cAMP that is produced by adenylyl cyclase, or the release of intracellular calcium, which is stimulated by PLC activity.

Conventional G-protein based, signal transduction assays have been difficult to develop for some targets, as a result of two major issues.

First, different GPCRs are coupled to different G protein regulated signal transduction pathways, and G-protein based assays are dependent on knowing the G-protein specificity of the target receptor, or require engineering of the cellular system, to force coupling of the target receptor to a particular effect or pathway. Second, all cells express a large number of endogenous GPCRs, as well as other signaling factors. As a result, the effector pathways that are measured may be modulated by other endogenous molecules in addition to the target GPCR, potentially leading to false results.

Regulation of G-protein activity is not the only result of ligand/GPCR binding. Luttrell, et al., *J. Cell Sci.*, 115:455-465 (2002), and Ferguson, *Pharmacol. Rev.*, 53:1-24 (2001), both of which are incorporated by reference, review other activities which lead to termination of the GPCR signal. These termination processes prevent excessive cell stimulation, and enforce temporal linkage between extracellular signal and corresponding intracellular pathway.

In the case of binding of an agonist to GPCR, serine and threonine residues at the C terminus of the GPCR molecule are phosphorylated. This phosphorylation is caused by the GPCR kinase, or "GRK," family. Agonist complexed, C-terminal phosphorylated GPCRs interact with arrestin family members, which "arrest" receptor signaling. This binding inhibits coupling of the receptor to G proteins, thereby targeting the receptor for internalization, followed by degradation and/or recycling. Hence, the binding of a ligand to a GPCR can be said to "modulate" the interaction between the GPCR and arrestin protein, since the binding of ligand to GPCR causes the arrestin to bind to the GPCR, thereby modulating its activity. Hereafter, when "modulates" or any form thereof is used, it refers simply to some change in the way the two proteins of the invention interact, when the test compound is present, as compared to how these two proteins interact, in its absence. For example, the presence of the test compound may strengthen or enhance the interaction of the two proteins, weaken it, inhibit it, or lessen it in some way, manner or form which can then be detected.

This background information has led to alternate methods for assaying activation and inhibition of GPCRs. These methods involve monitoring interaction with arrestins. A major advantage of this approach is that no knowledge of G-protein pathways is necessary.

Oakley, et al., *Assay Drug Dev. Technol.*, 1:21-30 (2002) and U.S. Pat. Nos. 5,891,646 and 6,110,693, incorporated by reference, describe assays where the redistribution of fluorescently labelled arrestin molecules in the cytoplasm to activated receptors on the cell surface is measured. These methods rely on high resolution imaging of cells, in order to measure arrestin relocalization and receptor activation. It will be recognized by the skilled artisan that this is a complex, involved procedure.

Various other U.S. patents and patent applications dealing with these points have issued and been filed. For example, U.S. Pat. No. 6,528,271 to Bohn, et al., deals with assays for screening for pain controlling medications, where the inhibitor of β-arrestin binding is measured. Published U.S. patent applications, such as 2004/0002119, 2003/0157553, 2003/0143626, and 2002/0132327, all describe different forms of assays involving GPCRs. Published application 2002/0106379 describes a construct which is used in an example which follows; however, it does not teach or suggest the invention described herein.

It is an object of the invention to develop a simpler assay for monitoring and/or determining modulation of specific protein/protein interactions, where the proteins include but are not limited to, membrane bound proteins, such as receptors, GPCRs in particular. How this is accomplished will be seen in the examples which follow.

SUMMARY OF THE INVENTION

Thus, in accordance with the present invention, there is provided a method for determining if a test compound modulates a specific protein/protein interaction of interest comprising contacting said compound to a cell which has been transformed or transfected with (a) a nucleic acid molecule which comprises, (i) a nucleotide sequence which encodes said first test protein, (ii) a nucleotide sequence encoding a cleavage site for a protease or a portion of a protease, and (iii) a nucleotide sequence which encodes a protein which activates a reporter gene in said cell, and (b) a nucleic acid molecule which comprises, (i) a nucleotide sequence which encodes a second test protein whose interaction with said first test protein in the presence of said test compound is to be measured, and (ii) a nucleotide sequence which encodes a protease or a portion of a protease which is specific for said cleavage site, and determining activity of said reporter gene as a determination of whether said compound modulates said protein/protein interaction.

The first test protein may be a membrane bound protein, such as a transmembrane receptor, and in particular a GPCR. Particular transmembrane receptors include β2-adrenergic receptor (ADRB2), arginine vasopressin receptor 2 (AVPR2), serotonin receptor 1a (HTR1A), m2 muscarinic acetylcholine receptor (CHRM2), chemokine (C-C motif) receptor 5 (CCR5), dopamine D2 receptor (DRD2), kappa opioid receptor (OPRK), or α1a-adregenic receptor (ADRA1A) although it is to be understood that in all cases the invention is not limited to these specific embodiments. For example, molecules such as the insulin growth factor-1 receptor (IGF-R), which is a tyrosine kinase, and proteins which are not normally membrane bound, like estrogen receptor 1 (ESR1) and estrogen receptors 2 (ESR2). The protease or portion of a protease may be a tobacco etch virus nuclear inclusion A protease. The protein which activates said reporter gene may be a transcription factor, such as tTA or GAL4. The second protein may be an inhibitory protein, such as an arrestin. The cell may be a eukaryote or a prokaryote. The reporter gene may be an exogenous gene, such as β-galactosidase or luciferase.

The nucleotide sequence encoding said first test protein may be modified to increase interaction with said second test protein. Such modifications include but are not limited to replacing all or part of the nucleotide sequence of the C-terminal region of said first test protein with a nucleotide sequence which encodes an amino acid sequence which has higher affinity for said second test protein than the original sequence. For example, the C-terminal region may be replaced by a nucleotide sequence encoding the C-terminal region of AVPR2, AGTRL1, GRPR, F2RL1, CXCR2/IL-8b, CCR4, or GRPR.

The method may comprise contacting more than one test compound to a plurality of samples of cells, each of said samples being contacted by one or more of said test compounds, wherein each of said cell samples have been transformed or transfected with the aforementioned nucleic acid molecules, and determining activity of reporter genes in said plurality of said samples to determine if any of said test compounds modulate a specific, protein/protein interaction. The method may comprise contacting each of said samples with one test compound, each of which differs from all others, or comprise contacting each of said samples with a mixture of said test compounds.

In another embodiment, there is provided a method for determining if a test compound modulates one or more of a plurality of protein interactions of interest, comprising contacting said test compound to a plurality of samples of cells, each of which has been transformed or transfected with (a) a first nucleic acid molecule comprising, (i) a nucleotide sequence which encodes a first test protein, a nucleotide sequence encoding a cleavage site for a protease, and (ii) a nucleotide sequence which encodes a protein which activates a reporter gene in said cell, (b) a second nucleic acid molecule which comprises, (i) a nucleotide sequence which encodes a second test protein whose interaction with said first test protein in the presence of said test compound of interest is to be measured, (ii) a nucleotide sequence which encodes a protease or a protease which is specific for said cleavage site, wherein said first test protein differs from other first test proteins in each of said plurality of samples, and determining activity of said reporter gene in at one or more of said plurality of samples as a determination of modulation of one or more protein interactions of interest.

The second test protein may be different in each sample or the same in each sample. All of said samples may be combined in a common receptacle, and each sample comprises a different pair of first and second test proteins. Alternatively, each sample may be tested in a different receptacle. The reporter gene in a given sample may differ from the reporter gene in other samples. The mixture of test compounds may comprise or be present in a biological sample, such as cerebrospinal fluid, urine, blood, serum, pus, ascites, synovial fluid, a tissue extract, or an exudate.

In yet another embodiment, there is provided a recombinant cell, transformed or transfected with (a) a nucleic acid molecule which comprises, (i) a nucleotide sequence which encodes said first test protein, (ii) a nucleotide sequence encoding a cleavage site for a protease or a portion of a protease, and (iii) a nucleotide sequence which encodes a protein which activates a reporter gene in said cell, and (b) a nucleic acid molecule which comprises, (i) a nucleotide sequence which encodes a second test protein whose interaction with said first test protein in the presence of said test compound is to be measured, and (ii) a nucleotide sequence which encodes a protease or a portion of a protease which is specific for said cleavage site.

One or both of said nucleic acid molecules may be stably incorporated into the genome of said cell. The cell also may have been transformed or transfected with said reporter gene. The first test protein may be a membrane bound protein, such as a transmembrane receptor, and in particular a GPCR. Particular transmembrane receptors include ADRB2, AVPR2, HTR1A, CHRM2, CCR5, DRD2, OPRK, or ADRA1A.

The protease or portion of a protease may be a tobacco etch virus nuclear inclusion A protease. The protein which activates said reporter gene may be a transcription factor, such as tTA or GAL4. The second protein may be an inhibitory protein. The cell may be a eukaryote or a prokaryote. The reporter gene may be an exogenous gene, such as β-galactosidase or luciferase. The nucleotide sequence encoding said first test protein may be modified to increase interaction with said second test protein, such as by replacing all or part of the nucleotide sequence of the C-terminal region of said first test protein with a nucleotide sequence which encodes an amino acid sequence which has higher affinity for said second test protein than the original sequence. The C-terminal region may be replaced by a nucleotide sequence encoding the C-terminal region of AVPR2, AGTRLI, GRPR, F2RL1, CXCR2/IL-8B, CCR4, or GRPR.

In still yet another embodiment, there is provided an isolated nucleic acid molecule which comprises, (i) a nucleotide sequence which encodes a test protein (ii) a nucleotide sequence encoding a cleavage site for a protease or a portion of a protease, and (iii) a nucleotide sequence which encodes a protein which activates a reporter gene in said cell. The test protein may be a membrane bound protein, such as is a transmembrane receptor. A particular type of transmembrane protein is a GPCR. Particular transmembrane receptors include ADRB2, AVPR2, HTR1A, CHRM2, CCR5, DRD2, OPRK, or ADRA1A. The protease or portion of a protease may be a tobacco etch virus nuclear inclusion A protease. The protein which activates said reporter gene may be a transcription factor, such as tTA or GAL4. As above, the invention is not to be viewed as limited to these specific embodiments.

In still a further embodiment, there is provided an expression vector comprising an isolated nucleic acid molecule which comprises, (i) a nucleotide sequence which encodes a test protein (ii) a nucleotide sequence encoding a cleavage site for a protease or a portion of a protease, and (iii) a nucleotide sequence which encodes a protein which activates a reporter gene in said cell, and further being operably linked to a promoter.

In still yet a further embodiment, there is provided an isolated nucleic acid molecule which comprises, (i) a nucleotide sequence which encodes a test protein whose interaction with another test protein in the presence of a test compound is to be measured, and (ii) a nucleotide sequence which encodes a protease or a portion of a protease which is specific for said cleavage site. The test protein may be an inhibitory protein, such as an arrestin.

Also provided is an expression vector comprising an isolated nucleic acid molecule which comprises, (i) a nucleotide sequence which encodes a test protein whose interaction with another test protein in the presence of a test compound is to be measured, and (ii) a nucleotide sequence which encodes a protease or a portion of a protease which is specific for said cleavage site, said nucleic acid further being operably linked to a promoter.

An additional embodiment comprises a fusion protein produced by expression of:
an isolated nucleic acid molecule which comprises, (i) a nucleotide sequence which encodes a test protein (ii) a nucleotide sequence encoding a cleavage site for a protease or a portion of a protease, and (iii) a nucleotide sequence which encodes a protein which activates a reporter gene in said cell, and further being operably linked to a promoter; or an isolated nucleic acid molecule which comprises, (i) a nucleotide sequence which encodes a test protein whose interaction with another test protein in the presence of a test compound is to be measured, and (ii) a nucleotide sequence which encodes a protease or a portion of a protease which is specific for said cleavage site In yet another embodiment, there is provided a test kit useful for determining if a test compound modulates a specific protein/protein interaction of interest comprising a separate portion of each of (a) a nucleic acid molecule which comprises, a nucleotide sequence which encodes said first test protein (i) a nucleotide sequence encoding a cleavage site for a protease or a portion of a protease, (ii) a nucleotide sequence which encodes a protein which activates a reporter gene in said cell, and (b) a nucleic acid molecule which comprises, (i) a nucleotide sequence which encodes a second test protein whose interaction with said first test protein in the presence of said test compound is to be measured, (ii) a nucleotide sequence which encodes a protease or a portion of a protease which is specific for said cleavage site, and container means for holding each of (a) and (b) separately from each other.

The first test protein may be a membrane bound protein, such as a transmembrane receptor. A particular type of transmembrane receptor is a GPCR. A particular transmembrane protein is a GPCR. Particular transmembrane receptors include ADRB2, AVPR2, HTR1A, CHRM2, CCR5, DRD2, OPRK, or ADRA1A. The protease or portion of a protease may be tobacco etch virus nuclear inclusion A protease. The protein which activates said reporter gene may be a transcription factor, such as tTA or GAL4. The second protein may be an inhibitory protein, such as an arrestin. The kit may further comprise a separate portion of an isolated nucleic acid molecule which encodes a reporter gene. The reporter gene may encode β-galactosidase or luciferase. The nucleotide sequence encoding said first test protein may be modified to increase interaction with said second test protein, such as by replacing all or part of the nucleotide sequence of the C-terminal region of said first test protein with a nucleotide sequence which encodes an amino acid sequence which has higher affinity for said second test protein than the original sequence. The nucleotide sequence of said C-terminal region may be replaced by a nucleotide sequence encoding the C-terminal region of AVPR2, AGTRLI, GRPR, F2RL1, CXCR2/IL-8B, CCR4, or GRPR.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF PREFERRED EMBODIMENTS

The present invention relates to methods for determining if a substance of interest modulates interaction of a first test protein, such as a membrane bound protein, like a receptor, e.g., a transmembrane receptor, with a second test protein, like a member of the arrestin family. The methodology involves cotransforming or cotransfecting a cell, which may be prokaryotic or eukaryotic, with two constructs. The first construct includes, a sequence encoding (i) the first test protein, such as a transmembrane receptor, (ii) a cleavage site for a protease, and (iii) a sequence encoding a protein which activates a reporter gene. The second construct includes, (i) a sequence which encodes a second test protein whose interaction with the first test protein is measured and/or determined, and (ii) a nucleotide sequence which encodes a protease or a portion of a protease sufficient to act on the cleavage site that is part of the first construct. In especially preferred embodiments, these constructs become stably integrated into the cells.

Figure 1:
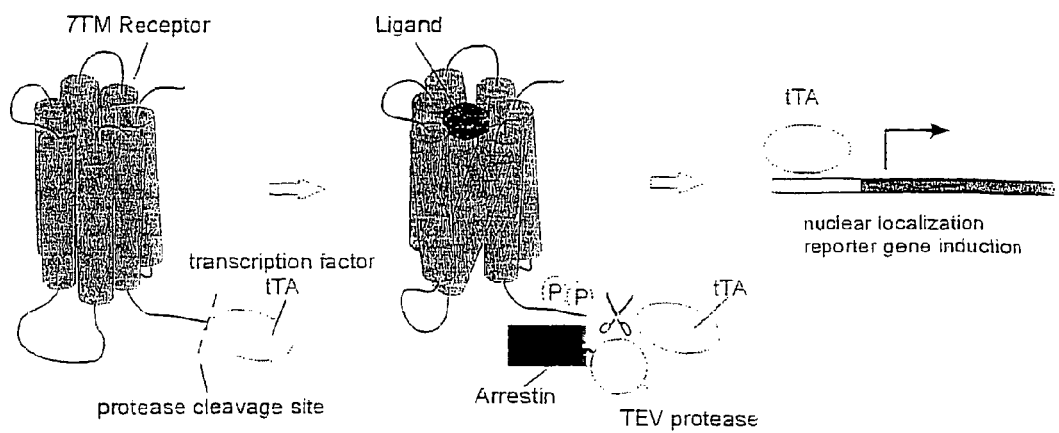
FIG. 1 shows the conceptual underpinnings of the invention, pictorially, using ligand-receptor binding as an example.

The features of an embodiment of the invention are shown, pictorially, in FIG. 1. In brief, first, standard techniques are employed to fuse DNA encoding a transcription factor to DNA encoding a first test protein, such as a transmembrane receptor molecule, being studied. This fusion is accompanied by the inclusion of a recognition and cleavage site for a protease not expressed endogenously by the host cell being used in the experiments.

DNA encoding this first fusion protein is introduced into and is expressed by a cell which also contains a reporter gene sequence, under the control of a promoter element which is dependent upon the transcription factor fused to the first test protein, e.g., the receptor. If the exogenous protease is not present, the transcription factor remains tethered to the first test protein and is unable to enter the nucleus to stimulate expression of the reporter gene.

Recombinant techniques can also be used to produce a second fusion protein. In the depicted embodiment, DNA encoding a member of the arrestin family is fused to a DNA molecule encoding the exogenous protease, resulting in a second fusion protein containing the second test protein, i.e., the arrestin family member.

An assay is then carried out wherein the second fusion protein is expressed, together with the first fusion protein, and a test compound is contacted to the cells, preferably for a specific length of time. If the test compound modulates interaction of the two test proteins, e.g., by stimulating, promoting or enhancing the association of the first and second test proteins, this leads to release of the transcription factor, which in turn moves to the nucleus, and provokes expression of the reporter gene. The activity of the reporter gene is measured.

In an alternative system, the two test proteins may interact in the absence of the test compound, and the test compound may cause the two test proteins to dissociate, lessen or inhibit their interaction. In such a case, the level of free, functionally active transcription factor in the cell decreases in the presence of the test compound, leading to a decrease in proteolysis, and a measurable decrease in the activity of the reporter gene.

In the depicted embodiment, the arrestin protein, which is the second test protein, binds to the receptor in the presence of an agonist; however, it is to be understood that since receptors are but one type of protein, the assay is not dependent upon the use of receptor molecules, nor is agonist binding the only interaction capable of being involved. Any protein will suffice, although the interest in transmembrane proteins is clear. Further, agonist binding to a receptor is not the only type of binding which can be assayed. One can determine antagonists, per se and also determine the relative strengths of different antagonists and/or agonists in accordance with the invention.

Other details of the invention, include specific methods and technology for making and using the subject matter thereof, are described below.

I. EXPRESSION CONSTRUCTS AND TRANSFORMATION

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis, et al., Molecular Cloning, A Laboratory Manual (Cold Spring Harbor, 1990) and Ausubel, et al., 1994, Current Protocols In Molecular Biology (John Wiley & Sons, 1996), both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleotide sequences that serve other functions as well and are described infra.

In certain embodiments, a plasmid vector is contemplated for use to in cloning and gene transfer. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-1 may be utilized in making a recombinant phage vector which can be used to transform host cells, such as, for example, *E. coli* LE392.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

Many prokaryotic vectors can also be used to transform eukaryotic host cells. However, it may be desirable to select vectors that have been modified for the specific purpose of expressing proteins in eukaryotic host cells. Expression systems have been designed for regulated and/or high level expression in such cells. For example, the insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Regulatory Signals

The construct may contain additional 5' and/or 3' elements, such as promoters, poly A sequences, and so forth. The elements may be derived from the host cell, i.e., homologous to the host, or they may be derived from distinct source, i.e., heterologous.

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid molecule, as may be obtained by isolating the 5' non-coding sequences located upstream of the coding segment and/or exon. Such a promoter can be referred to as "endogenous." Similarly, an enhancer may be one naturally associated with a nucleic acid molecule, located either downstream or upstream of that sequence. Alternatively, certain advantages will be gained by positioning the coding nucleic acid segment under the control of a recombinant or heterologous promoter, which refers to a promoter that is not normally associated with a nucleic acid molecule in its natural environment. A recombinant or heterologous enhancer refers also to an enhancer not normally associated with a nucleic acid molecule in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook, et al., 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, Nature, 334:320-325 (1988)). IRES elements from two members of the picornavirus family (polio and encephalomyocarditis) have been described (Pelletier and Sonenberg, supra), as well an IRES from a mammalian message (Macejak and Sarnow, Nature, 353:90-94 (1991))1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Other Vector Sequence Elements

Vectors can include a multiple cloning site (MCS), which is a nucleic acid region that contains multiple restriction enzyme sites, any of which can be used in conjunction with standard recombinant technology to digest the vector (see, for example, Carbonelli, et al., FEMS Microbiol. Lett., 172(1): 75-82 (1999), Levenson, et al., Hum. Gene Ther. 9(8):1233-1236 (1998), and Cocea, Biotechniques, 23(5):814-816 (1997)), incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler, et al., 1997, herein incorporated by reference).

The vectors or constructs of the present invention will generally comprise at least one termination signal. A "termination signal" or "terminator" comprises a DNA sequence involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 adenosine residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not being limited to, for example, the termination sequences of genes, such as the bovine growth hormone terminator, viral termination sequences, such as the SV40 terminator. In certain embodiments, the termination signal may be a lack of transcribable or translatable sequence, such as an untranslatable/untranscribable sequence due to a sequence truncation.

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, both of which are convenient, readily available, and known to function well in various target cells. Polyadenylation may increase the stability of the transcript or may facilitate cytoplasmic transport.

In order to propagate a vector in a host cell, it may contain one or more origins of replication (often termed "ori"), sites which are specific nucleotide sequences at which replication is initiated. Alternatively, an autonomously replicating sequence (ARS) can be employed if the host cell is yeast.

Transformation Methodology

Suitable methods for nucleic acid delivery for use with the current invention are believed to include virtually any method by which a nucleic acid molecule (e.g., DNA) can be introduced into a cell as described herein or as would be known to one of ordinary skill in the art. Such methods include, but are not limited to, direct delivery of DNA such as by ex vivo transfection (Wilson, et al., *Science,* 244:1344-1346 (1989), Nabel et al, *Science,* 244:1342-1344 (1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, *J. Cell Biol.,* 101(3):1094-1099 (1985); U.S. Pat. No. 5,789,215, incorporated herein by reference); by electroporation (U.S. Pat. No. 5,384,253, incorporated herein by reference; Tur-Kaspa, et al., *Mol. Cell Biol.,* 6:716-718 (1986); Potter, et al., *Proc. Natl. Acad. Sci. USA,* 81:7161-7165 (1984); by calcium phosphate precipitation (Graham and Van Der Eb, *Virology,* 52:456-467 (1973); Chen and Okayama, *Mol. Cell Biol.,* 7(8):2745-2752 (1987); Rippe, et al., *Mol. Cell Biol.,* 10:689-695 (1990); by using DEAE-dextran followed by polyethylene glycol (Gopal, *Mol. Cell Biol.,* 5:1188-190 (1985); by direct sonic loading (Fechheimer, et al., *Proc. Natl. Acad. Sci. USA,* 89(17):8463-8467 (1987); by liposome mediated transfection (Nicolau and Sene, *Biochem. & Biophys. Acta.,* 721:185-190 (1982); Fraley, et al., *Proc. Natl. Acad. Sci. USA,* 76:3348-3352 (1979); Nicolau, et al., *Meth. Enzym.,* 149:157-176 (1987); Wong, et al., *Gene,* 10:879-894 (1980); Kaneda, et al., *Science,* 243: 375-378 (1989); Kato, et al., *J. Biol. Chem.,* 266:3361-3364 (1991) and receptor-mediated transfection (Wu and Wu, *J. Biol. Chem.,* 262:4429-4432 (1987); Wu and Wu, 1988); by PEG-mediated transformation of protoplasts (Omirulleh, et al., *Plant Mol. Biol.,* 21(3):415-428 (1987); U.S. Pat. Nos. 4,684,611 and 4,952,500, each incorporated herein by reference); by desiccation/inhibition-mediated DNA uptake (Potrykus, et al. *Mol. Gen. Genet.,* 199(2):169-177 (1985), and any combination of such methods.

II. COMPONENTS OF THE ASSAY SYSTEM

As with the method described herein, the products which are features of the invention have preferred embodiments. For example, in the "three part construct," i.e., that contain sequences encoding a test protein, the cleavage site, and the activator protein, the test protein is preferably a membrane bound protein, such as a transmembrane receptor, e.g., a member of the GPCR family. These sequences can be modified so that the C terminus of the proteins they encode have better and stronger interactions with the second protein. The modifications can include, e.g., replacing a C-terminal encoding sequence of the test protein, such as a GPCR, with the C terminal coding region for AVPR2, AGTRLI, GRPR, F2PL1, CCR4, CXCR2/IL-8, CCR4, or GRPR, all of which are defined supra.

The protein which activates the reporter gene may be a protein which acts within the nucleus, like a transcription factor (e.g., tTA, GAL4, etc.), or it may be a molecule that sets a cascade of reactions in motion, leading to an intranuclear reaction by another protein. The skilled artisan will be well versed in such cascades.

The second construct, as described supra, includes a region which encodes a protein that interacts with the first protein, leading to some measurable phenomenon. The protein may be an activator, an inhibitor, or, more, generically, a "modulator" of the first protein. Members of the arrestin family are preferred, especially when the first protein is a GPCR, but other protein encoding sequences may be used, especially when the first protein is not a GPCR. The second part of these two part constructs encodes the protease, or portion of a protease, which acts to remove the activating molecule from the fusion protein encoded by the first construct.

However, these preferred embodiments do not limit the invention, as discussed in the following additional embodiments.

Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. The host cells generally will have been engineered to express a screenable or selectable marker which is activated by the transcription factor that is part of a fusion protein, along with the first test protein.

In the context of expressing a heterologous nucleic acid sequence, "host cell" refers to a prokaryotic or eukaryotic cell that is capable of replicating a vector and/or expressing a heterologous gene encoded by a vector. When host cells are "transfected" or "transformed" with nucleic acid molecules, they are referred to as "engineered" or "recombinant" cells or host cells, e.g., a cell into which an exogenous nucleic acid sequence, such as, for example, a vector, has been introduced. Therefore, recombinant cells are distinguishable from naturally-occurring cells which do not contain a recombinantly introduced nucleic acid.

Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F-, lambda-, prototrophic, ATCC No. 273325), DH5α, JM109, and KC8, bacilli such as *Bacillus subtilis*; and other enterobacteriaceae such as *Salmonella typhimurium, Serratia marcescens,* various *Pseudomonas* specie, as well as a number of commercially available bacterial hosts such as SURE® Competent Cells and SOLOPACK™ Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, COS, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Test Proteins

The present invention contemplates the use of any two proteins for which a physical interaction is known or suspected. The proteins will exist as fusions proteins, a first test protein fused to a transcription factor, and the second test protein fused to a protease that recognizes a cleavage site in the first fusion protein, cleavage of which releases the transcription factor. The only requirements for the test proteins/fusions are (a) that the first test protein cannot localize to the nucleus prior to cleavage, and (b) that the protease must remain active following both fusion to the second test protein and binding of the first test protein to the second test protein.

With respect to the first construct, the first test protein may be, e.g., a naturally membrane bound protein, or one which has been engineered to become membrane bound, via standard techniques. The first test protein may be, e.g., a transmembrane receptor such as any of the GPCRs, or any other transmembrane receptor of interest, including, but not being limited to, receptor tyrosine kinases, receptor serine threonine kinases, cytokine receptors, and so forth. Further, as it is well known that portions of proteins, will function in the same manner as the full length first test protein, such active portions of a first test protein are encompassed by the definition of protein herein.

As will be evident to the skilled artisan, the present invention may be used to assay for interaction with any protein, and is not limited in its scope to assaying membrane bound receptor, like the GPCRs. For example, the activity of other classes of transmembrane receptors, including but not limited to: receptor tyrosine kinases (RTKs), such as IGF1R, such as the epidermal growth factor receptor (EGFR), ErbB2/HER2/Neu or related RTKs; receptor serine/threonine kinases, such as Transforming Growth Factor-beta (TGFβ), activin, or Bone Morphogenetic Protein (BMP) receptors; cytokine receptors, such as receptors for the interferon family for interleukin, erythropoietin, G-CSF, GM-CSF, tumor necrosis factor (TNF) and leptin receptors; and other receptors, which are not necessarily normally membrane bound, such as estrogen receptor 1 (ESR1), and estrogen receptor 2 (ESR2). In each case, the method involves transfecting a cell with a modified receptor construct that directs the expression of a chimeric protein containing the receptor of interest, to which is appended, a protease cleavage site followed by a nucleic acid molecule encoding a transcription factor. The cell is co-transfected with a second construct that directs the expression of a chimeric protein consisting of an interacting protein fused, to the protease that recognizes and cleaves the site described supra. In the case of RTKs, such as the EGFR, this interacting protein may consist of a SH2 (Src homology domain 2) containing protein or portion thereof, such as phospholipase C (PLC) or Src homology 2 domain containing transforming protein 1 (SHC1). In the case of receptor serine/threonine kinases, such as TGFβ, activin, BMP receptors, this interacting protein may be a Smad protein or portion thereof. In the case of cytokine receptors, such as interferon-α/β or interferon-γ gamma receptors, this interacting protein may be a signal transducer and activator of transcription (STAT) protein such as, but not being limited to, Stat1, Stat2; Janus kinase (JAK) proteins Jak1, Jak2, or Tyk2; or portions thereof. In each case, the transfected cell contains a reporter gene that is regulated by the transcription factor fused to the receptor. An assay is then performed in which the transfected cells are treated with a test compound for a specific period and the reporter gene activity is measured at the end of the test period. If the test compound activates the receptor of interest, interactions between the receptor of interest and the interacting protein are stimulated, leading to cleavage of the protease site and release of the fused transcription factor, which is in turn measurable as an increase in reporter gene activity.

Other possible test protein pairs include antibody-ligands, enzyme-substrates, dimerizing proteins, components of signal transduction cascades, and other protein pairs well known to the art.

Reporters

The protein which activates a reporter gene may be any protein having an impact on a gene, expression or lack thereof which leads to a detectable signal. Typical protein reporters include enzymes such as chloramphenicol acetyl transferase (CAT), β-glucuronidase (GUS) or β-galactosidase. Also contemplated are fluorescent and chemilluminescent proteins such as green fluorescent protein, red fluorescent protein, cyan fluorescent protein luciferase, beta lactamase, and alkaline phosphatase.

Transcriptions Factors and Repressors

In accordance with the present invention, transcription factors are used to activate expression of a reporter gene in an engineered host cell. Transcription factors are typically classified according to the structure of their DNA-binding domain, which are generally (a) zinc fingers, (b) helix-turn-helix, (c) leucine zipper, (d) helix-loop-helix, or (e) high mobility groups. The activator domains of transcription factors interact with the components of the transcriptional apparatus (RNA polymerase) and with other regulatory proteins, thereby affecting the efficiency of DNA binding.

The Rel/Nuclear Factor kB (NF-kB) and Activating Protein-1 (AP-1) are among the most studied transcription factor families. They have been identified as important components of signal transduction pathways leading to pathological outcomes such as inflammation and tumorogenesis. Other transcription factor families include the heat shock/E2F family, POU family and the ATF family. Particular transcription factors, such as tTA and GAL4, are contemplated for use in accordance with the present invention.

Though transcription factors are one class of molecules that can be used, the assays may be modified to accept the use of transcriptional repressor molecules, where the measurable signal is downregulation of a signal generator, or even cell death.

Proteases and Cleavage Sites

Proteases are well characterized enzymes that cleave other proteins at a particular site. One family, the Ser/Thr proteases, cleave at serine and threonine residues. Other proteases include cysteine or thiol proteases, aspartic proteases, metalloproteinases, aminopeptidases, di & tripeptidases, carboxypeptidases, and peptidyl peptidases. The choice of these is left to the skilled artisan and certainly need not be limited to the molecules described herein. It is well known that enzymes have catalytic domains and these can be used in place of full length proteases. Such are encompassed by the invention as well. A specific embodiment is the tobacco etch virus nuclear inclusion A protease, or an active portion thereof. Other specific cleavage sites for proteases may also be used, as will be clear to the skilled artisan.

Modification of Test Proteins

The first test protein may be modified to enhance its binding to the interacting protein in this assay. For example, it is known that certain GPCRs bind arrestins more stably or with greater affinity upon ligand stimulation and this enhanced interaction is mediated by discrete domains, e.g., clusters of serine and threonine residues in the C-terminal tail (Oakley, et al., *J. Biol. Chem.*, 274:32248-32257, 1999 and Oakley, et al., *J. Biol. Chem.*, 276:19452-19460, 2001). Using this as an example, it is clear that the receptor encoding sequence itself may be modified, so as to increase the affinity of the membrane bound protein, such as the receptor, with the protein to which it binds. Exemplary of such modifications are modifications of the C-terminal region of the membrane bound protein, e.g., receptor, such as those described supra, which involve replacing a portion of it with a corresponding region of another receptor, which has higher affinity for the binding protein, but does not impact the receptor function. Examples 16 and 20, supra, show embodiments of this feature of the invention.

In addition, the second test protein may be modified to enhance its interaction with the first test protein. For example, the assay may incorporate point mutants, truncations or other variants of the second test protein, e.g., arrestin that are known to bind agonist-occupied GPCRs more stably or in a phosphorylation-independent manner (Kovoor, et al., *J. Biol. Chem.*, 274:6831-6834, 1999).

III. ASSAY FORMATS

As discussed above, the present invention, in one embodiment, offers a straightforward way to assess the interaction of two test proteins when expressed in the same cell. A first construct, as described supra, comprises a sequence encoding a first protein, concatenated to a sequence encoding a cleavage site for a protease or protease portion, which is itself concatenated to a sequence encoding a reporter gene activator. By "concatenated" is meant that the sequences described are fused to produce a single, intact open reading frame, which may be translated into a single polypeptide which contains all the elements. These may, but need not be, separated by additional nucleotide sequences which may or may not encode additional proteins or peptides. A second construct inserted into the recombinant cells is also as described supra, i.e., it contains both a sequence encoding a second protein, and the protease or protease portion. Together, these elements constitute the basic assay format when combined with a candidate agent whose effect on target protein interaction is sought.

However, the invention may also be used to assay more than one membrane bound protein, such as a receptor, simultaneously by employing different reporter genes, each of which is stimulated by the activation of a protein, such as the classes of proteins described herein. For example, this may be accomplished by mixing cells transfected with different receptor constructs and different reporter genes, or by fusing different transcription factors to each test receptor, and measuring the activity of each reporter gene upon treatment with the test compound. For example, it may be desirable to determine if a molecule of interest activates a first receptor and also determine if side effects should be expected as a result of interaction with a second receptor. In such a case one may, e.g., involve a first cell line encoding a first receptor and a first reporter, such as lacZ, and a second cell line encoding a second receptor and a second reporter, such as GFP. Preferred embodiments of such a system are seen in Examples 17 and 18. One would mix the two cell lines, add the compound of interest, and look for a positive effect on one, with no effect on the other.

It is contemplated that the invention relates both to assays where a single pair of interacting test proteins is examined, but more preferably, what will be referred to herein as "multiplex" assays are used. Such assays may be carried out in various ways, but in all cases, more than one pair of test proteins is tested simultaneously. This may be accomplished, e.g., by providing more than one sample of cells, each of which has been transformed or transfected, to test each interacting pair of proteins. The different transformed cells may be combined, and tested simultaneously, in one receptacle, or each different type of transformant may be placed in a different well, and then tested.

The cells used for the multiplex assays described herein may be, but need not be, the same. Similarly, the reporter system used may, but need not be, the same in each sample.

After the sample or samples are placed in receptacles, such as wells of a microarray, one or more compounds may be screened against the plurality of interacting protein pairs set out in the receptacles.

The fusion proteins expressed by the constructs are also a feature of the invention. Other aspects of the invention which will be clear to the artisan, are antibodies which can identify the fusion proteins as well as various protein based assays for determining the presence of the protein, as well as hybridization assays, such as assays based on PCR, which determine expression of the gene.

IV. KITS

Any of the compositions described herein may be comprised in a kit. The kits will thus comprise, in suitable container means for the vectors or cells of the present invention, and any additional agents that can be used in accordance with the present invention.

The kits may comprise a suitably aliquoted compositions of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit will also generally contain a second, third or other additional container into which the additional components may be separately placed. However, various combinations of components may be comprised in a vial. The kits of the present invention also will typically include a means for containing reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

V. EXAMPLES

Specific embodiments describing the invention will be seen in the examples which follow, but the invention should not be deemed as limited thereto.

Example 1

A fusion construct was created, using DNA encoding human β2 adrenergic receptor, referred to hereafter as "ADRB2", in accordance with standard nomenclature. Its nucleotide sequence can be found at GenBank, under Accession Number NM_000024 (SEQ ID NO: 1). The tetracycline controlled transactivator tTA, described by Gossen, et al., *Proc. Natl. Acad. Sci. USA,* 87:5547-5551 (1992), incorporated by reference, was also used. A sequence encoding the recognition and cleavage site for tobacco etch virus nuclear inclusion A protease, described by Parks, et al., *Anal. Biochem.,* 216:413-417 (1994), incorporated by reference, is inserted between these sequences in the fusion coding gene. The CMV promoter region was placed upstream of the ADRB2 coding region, and a poly A sequence was placed downstream of the tTA region.

A fusion construct was prepared by first generating a form of ADRB2 which lacked internal BamHI and BglII restriction sites. Further, the endogenous stop codon was replaced with a unique BamHI site.

Overlapping PCR was used to do this. To elaborate, a 5' portion of the coding region was amplified with:

```
gattgaagat ctgccttctt gctggc,     (SEQ ID NO: 2)
and gcagaacttg aagacctgc ggagtcc,     (SEQ ID NO: 3)
``` while a 3' portion of the coding region was amplified with:

```
ggactccgca ggtcttccaa gttctgc,    (SEQ ID NO: 4)
and ttcggatcct agcagtgagt catttgt.    (SEQ ID NO: 5)
```

The resulting PCR products have 27 nucleotides of overlapping sequence and were purified via standard agarose gel electrophoresis. These were mixed together, and amplified with SEQ ID NO: 2, and SEQ ID NO: 5.

PCR was also used to modify the coding region of tTA so that the endogenous start codon was replaced with a TEV NIa-Pro cleavage site. The cleavage site, defined by the seven amino acid sequence ENLYFQS (SEQ ID NO: 6), is taught by Parks, et al., *Anal. Biochem.*, 216:413-417 (1994), incorporated by reference. The seventh amino acid is known as P1' position, and replacing it with other amino acids is known to reduce the efficiency of cleavage by TEV NIa-Pro. See Kapust, et al., *Biochem. Biophys. Res. Commun.*, 294:949-955 (2002).

Variants where the seventh amino acid was changed to Tyr, and where it was changed to Leu, were produced. These resulted in intermediate and low efficiency cleavage sites, as compared to the natural high efficiency site.

A DNA sequence encoding the natural high efficiency site was added to the tTA coding region in two steps. Briefly, BamHI and XbaI restriction sites were added to the 5' end and a XhoI restriction site was added to the 3' end of the tTA coding region by PCR with

```
                                  (SEQ ID NO: 7)
    ccggatcctc tagattagat aaaagtaaag tg
    and (SEQ ID NO: 8)
    gactcgagct agcagtatcc tcgcgccccc taccc,
``` and the TEV NIa-Pro cleavage site was added to the 5' end by ligating an oligonucleotide with the sequence

```
    gagaacctgt acttccag        (SEQ ID NO: 9)
``` between the BamHI and XbaI sites.

This DNA sequence was modified to encode the intermediate and low efficiency cleavage sites by PCR using:

```
                                  (SEQ ID NO: 10)
    ggatccgaga acctgtactt ccagtacaga tta,
    and (SEQ ID NO: 11)
    ctcgagagat cctcgcgccc cctacccacc.
``` for ENLYFQY (SEQ ID NO: 12), and

```
                                  (SEQ ID NO: 13)
    ggatccgaga acctgtactt ccagctaaga tta,
    and (SEQ ID NO: 11)
    ctcgagagat cctcgcgccc cctacccacc
    for (SEQ ID NO: 14)
    ENLYFQL.
```

These PCR steps also introduced a BamHI restriction site 5' to the sequence encoding each cleavage site, and an XhoI restriction site 3' to tTA stop codon.

The thus modified ADRB2 coding region was digested with PstI, which cuts at nucleotide position 260 in the coding region, and BamHI. This 3' fragment was ligated with the three variants of tTA modified with the TEV NIa-Pro cleavage sites, that had been digested with BamHI and XhoI, and the resulting complexes were cloned into pBlueScript II, which had been digested with PstI and XhoI.

A NotI restriction site was introduced 5' to the start codon of the ADRB2 coding region, again via PCR, using

```
                                  (SEQ ID NO: 15)
    gcggccgcca ccatgaacgg taccgaaggc cca,
    and (SEQ ID NO: 16)
    ctggtgggtg gccggtacc a.
```

The 5' fragment of modified ADRB2 coding region was isolated, via digestion with NotI and PstI and was ligated into each of the constructs of the 3' fragment of ADRB2-TEV-NIa-Pro-cleavage site tTA fusions that had been digested previously, to produce three, full length constructs encoding fusion proteins.

Each construct was digested with NotI and XhoI, and was then inserted into the commercially available expression vector pcDNA 3, digested with NotI and XhoI.

Example 2

A second construct was also made, whereby the coding sequence for "β arrestin 2 or ARRB2" hereafter (GenBank, NM_004313) (SEQ ID NO: 17), was ligated to the catalytic domain of the TEV NIa protease (i.e., amino acids 189-424 of mature NIa protease, residues 2040-2279) in the TEV protein. To do this, a DNA sequence encoding ARRB2 was modified, so as to add a BamHI restriction site to its 5' end. Further, the sequence was modified to replace the endogenous stop codon with a BamHI site. The oligonucleotides

```
                                  (SEQ ID NO: 18)
    caggatcctc tggaatgggg gagaaacccg ggacc,
    and (SEQ ID NO: 19)
    ggatccgcag agttgatcat catagtcgtc
``` were used. The resulting PCR product was cloned into the commercially available vector pGEM-T EASY (Promega). The multiple cloning site of the pGEM-T EASY vector includes an EcoRI site 5' to the start codon of ARRB2.

The TEV NIa-Pro coding region was then modified to replace the endogenous start codon with a BglII site, and to insert at the 3' end a sequence which encodes influenza hemagluttinin epitope YPYDVPDYA (SEQ ID NO: 20) in accordance with Kolodziej, et al., *Meth. Enzymol.*, 194:508-519

(1991), followed by a stop codon, and a NotI restriction site. This was accomplished via PCR, using

```
                                          (SEQ ID NO: 21)
   agatctagct tgtttaaggg accacgtg,
   and
```

```
                                          (SEQ ID NO: 22)
   gcggccgctc aagcgtaatc tggaacatca tatgggtacg
   agtacaccaa ttcattcatg ag.
```

The resulting, modified ARRB2 coding region was digested with EcoRI and BamHI, while the modified TEV coding region was cleaved with BglII and NotI. Both fragments were ligated into a commercially available pcDNA3 expression vector, digested with EcoRI and NotI.

Example 3

Plasmids encoding ADRB2-TEV-NIa-Pro cleavage site-tTA and the ARRB2-TEV-NIa protease fusion proteins were transfected into HEK-293T cells, and into "clone 41," which is a derivative of HEK-293T, that has a stably integrated β-galactosidase gene under control of a tTA dependent promoter. About $5 \times 10^4$ cells were plated in each well of a 24 well plate, in DMEM medium supplemented with 10% fetal bovine serum, 2 mM L-glutamine, 100 units/ml penicillin, 100 μg/ml G418, and 5 μg/ml purimycin. Cells were grown to reach 50% confluency the next day, and were then transfected, using 0.4 μg plasmid DNA, and 2 μl Fugene (a proprietary transfection reagent containing lipids and other material). The mix was combined in 100 μl of DMEM medium, and incubated for 15 minutes at room temperature prior to adding cells. Transfected cells were incubated for 8-20 hours before testing by adding drugs which are known agonists for the receptor, and then 16-24 hours after drug addition.

Example 4

The levels of β-galactosidase activity in the cells were first measured by staining the cells with a chromogenic substance, i.e., "X-gal," as taught by MacGregor, et al., *Somat. Cell Mol. Genet.*, 13:253-265 (1987), incorporated by reference. Following culture, cells were washed, twice, in D-PBS with calcium and magnesium, fixed for 5 minutes in 4% paraformaldehyde, and then washed two additional times with D-PBS, calcium and magnesium, for 10 minutes each time. Fixed cells were incubated with 5 mM potassium ferricyanide, 5 mM potassium ferrocyanide, 2 mM $MgCl_2$, 0.1% X-Gal, that had been prepared from a 1:40 dilution of 4% X-Gal stock in dimethylformamide, in D-PBS with calcium and magnesium.

The reaction was incubated in the dark at room temperature for from 3-4 hours, to overnight. Substrate solution was removed, and cells were mounted under glass coverslips with mowiol mounting medium (10% mowiol, 0.1% 1.4-diazabicyclo[2.2.2]octane, 24% glycerol).

The results indicated that cells transfected with either the ADRB2-TEV-NIa-Pro cleavage site-tTA plasmid alone or the ARRB2-TEV-NIa protease plasmid alone did not express β-galactosidase. A small fraction of cells transfected with both plasmids did express β-galactosidase, probably due to basal levels of interaction between unstimulated ADRB2 and ARRB2. About 3-5 fold more cells expressed the reporter gene after treatment with either 10 μM isoproterenol, or 10 μM epinephrine, both of which are ADRB2 agonists.

When the cells were pretreated for 5 minutes with the ADRB2 antagonist alprenolol (10 μM), the agonist induced increase in β-galactosidase expressing cells was blocked, and treatment with alprenolol alone had no apparent effect;

These results show that one can link agonist binding and GPCR stimulation to transcriptional activation of a reporter gene.

Example 5

A set of experiments were carried out in order to quantify the level of reporter gene activity in the cells more precisely and to maximize the signal-to-background ratio of the assay. This was accomplished by measuring the level of reporter gene induction using a commercially available chemiluminescence assay for β-galactosidase activity. Clone 41 cells were transfected with the ADRB2-tTA fusion constructs, containing either the high, medium or low efficiency cleavage sites, and the ARRB2-TEV-NIa protease expression plasmid described supra. Cells were either untreated or treated with 1 μM isoproterenol 20 hours after the transfection, and the luminescence assay was carried out 24 hours after the drug addition. In brief, following cell culture, the medium was removed, and 50 μl of lysis buffer (100 mM potassium phosphate, pH7.8, 0.2% Triton X-100) was added to each well. The cells were lysed via incubation for 5 minutes, at room temperature, with mild agitation. Lysates were collected and analyzed via commercially available products.

In all cases, treatment with agonist increased levels of β-galactosidase activity. However, the background level of reporter gene activity in untreated cells was lowest with the low efficiency cleavage site, relative to the medium and high efficiency sites. Further, agonist treatment resulted in a 4.8-fold stimulation of reporter gene activity in cells transfected with the low efficiency cleavage site, compared to 2.8-fold for the medium efficiency cleavage site and 1.2-fold for the high efficiency cleavage site. Thus, the highest signal-to-background ratio is obtained by using the low efficiency protease cleavage site.

Example 6

These experiments were designed to verify that the agonist stimulated increase in reporter gene expression is dependent on binding and activation of the receptor by the agonist.

To do this, variants of the ADRB2-tTA fusion constructs were generated following the protocols supra, except each contained a mutant form of the receptor with a single amino acid change from D to S at position 113, which results in a greatly reduced affinity for the agonist isoproterenol. See Strader, et al., *J. Biol. Chem.*, 266:5-8 (1991). Three forms of the mutant receptor-tTA fusion construct with each of the different cleavage sites were formed.

The levels of β-galactosidase activity were measured in clone 41 cells co-transfected with the ADRB2-tTA fusion constructs containing the D113S point mutation and the ARRB2-TEV-NIa protease expression plasmid described previously. The activity tests were carried out exactly as described, supra. The results indicated that the agonist isoproterenol did not stimulate reporter gene expression in cells expressing the mutant ADRB2-tTA fusion contructs.

Example 7

These experiments were designed to examine whether the agonist stimulated increase in reporter gene expression is dependent on fusion of TEV NIa-Pro to ARRB2.

To do this, the levels of β-galactosidase activity were measured in clone 41 cells co-transfected with the ADRB2-tTA fusion construct containing the low efficiency cleavage site and either the ARRB2-TEV-NIa protease expression plasmid described supra, or a control TEV-NIa protease fusion to the SH2 domain of phospholipase C. The activity tests were carried out exactly as described, supra. The results indicated that agonist-stimulated increase in reporter gene expression was detected only when the TEV protease was fused to ARRB2 and not when fused to an unrelated polypeptide.

Example 8

These experiments were designed to determine if gene expression is induced selectively by agonists of the target receptor, or if it can be stimulated by other molecules.

ATP is an agonist for G protein coupled receptors P2Y1 and P2Y2, which are expressed endogenously by HEK-293T cells.

Experiments were carried out using clone 41 cells which were cotransfected with the ADRB2-tTA fusion construct containing the low efficiency cleavage site and the arrestin-TEV-NIa protease fusion as described supra, which were treated with isoproterenol, ATP, or untreated. The assays were carried out as described, supra.

The results indicated that induction of reporter gene activity was specific to activation of target receptor. Stimulation of another GPCR pathway was irrelevant.

Example 9

Figure 2A:
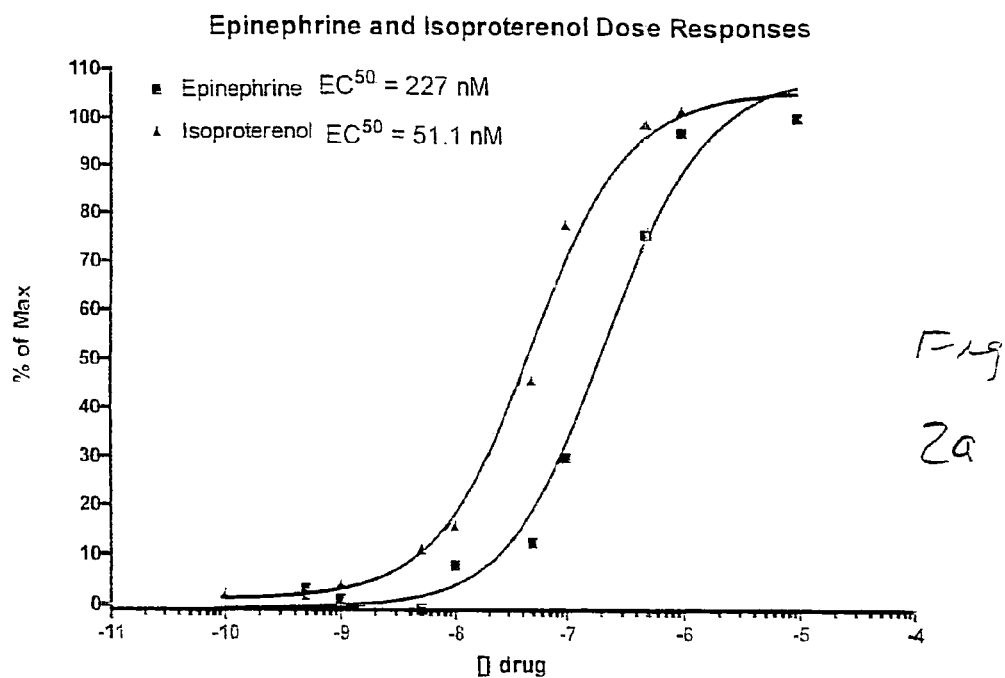
FIGS. 2a and 2b show that the response of targets in assays in accordance with the invention is dose dependent, both for agonists and antagonists.

A set of experiments were carried out using clone 41 cells which were cotransfected with the ADRB2-tTA fusion construct containing the low efficiency cleavage site and the ARRB2-TEV-NIa protease fusion as described supra, which were treated with varying amounts of one of the adrenergic receptor agonists isoproterenol and epinephrine. The assays were carried out as described, supra. The results presented in FIG. 2a show a dose-response curve for the stimulation of reporter gene expression by these two ligands. Each point represents the mean value obtained from three experiments.

Figure 2B:
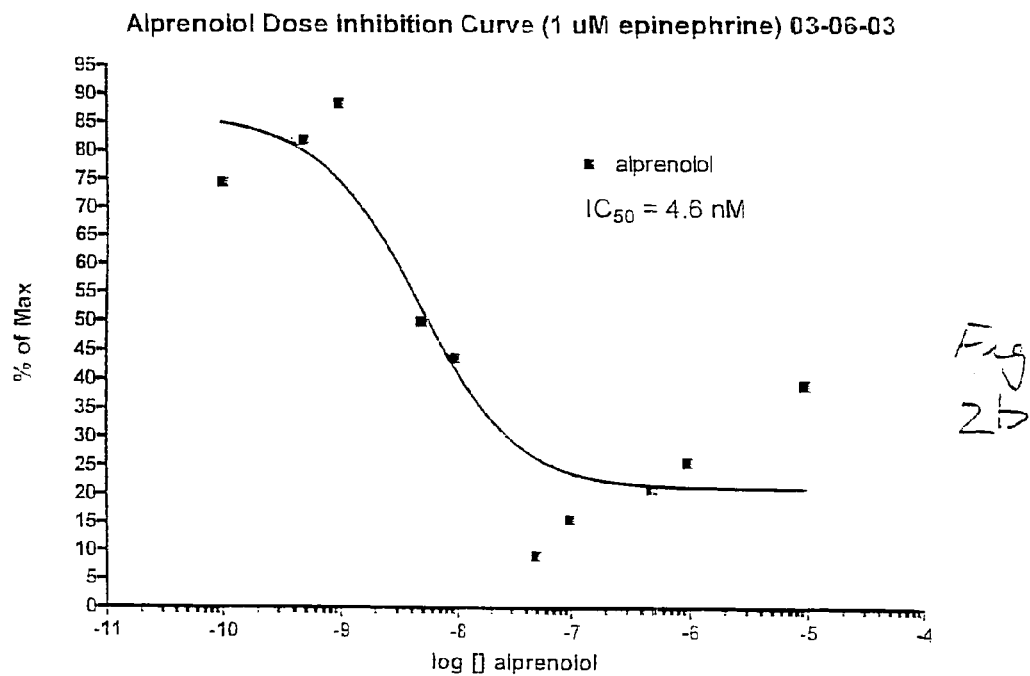

A set of experiments were carried out as described supra, in which the co-transfected clone 41 cells were pretreated with varying concentrations of the adrenergic receptor antagonist alprenolol for 15 minutes, followed by treatment with 1 µM epinephrine. The results shown in FIG. 2b indicate a dose-inhibition curve for this antagonist.

Example 10

A similar set of constructs were made to establish an assay for the G protein coupled arginine vasopressin receptor 2 (AVPR2). The AVPR2 coding region (Genbank Accession Number: NM_000054) (SEQ ID NO: 23) was modified to place an EcoRI site at the 5' end and replace the stop codon with a BamHI site using PCR with the primers

```
                                    (SEQ ID NO: 24)
    gaattcatgc tcatggcgtc caccac
    and (SEQ ID NO: 25)
    ggatcccgat gaagtgtcct tggccag.
```

The modified AVPR2 coding region was ligated into the three ADRB2-tTA constructs described supra, which had been cut with EcoRI and BamHI. This replaced the entire coding sequence of the ADRB2 with the coding sequence of AVPR2.

Figure 3:
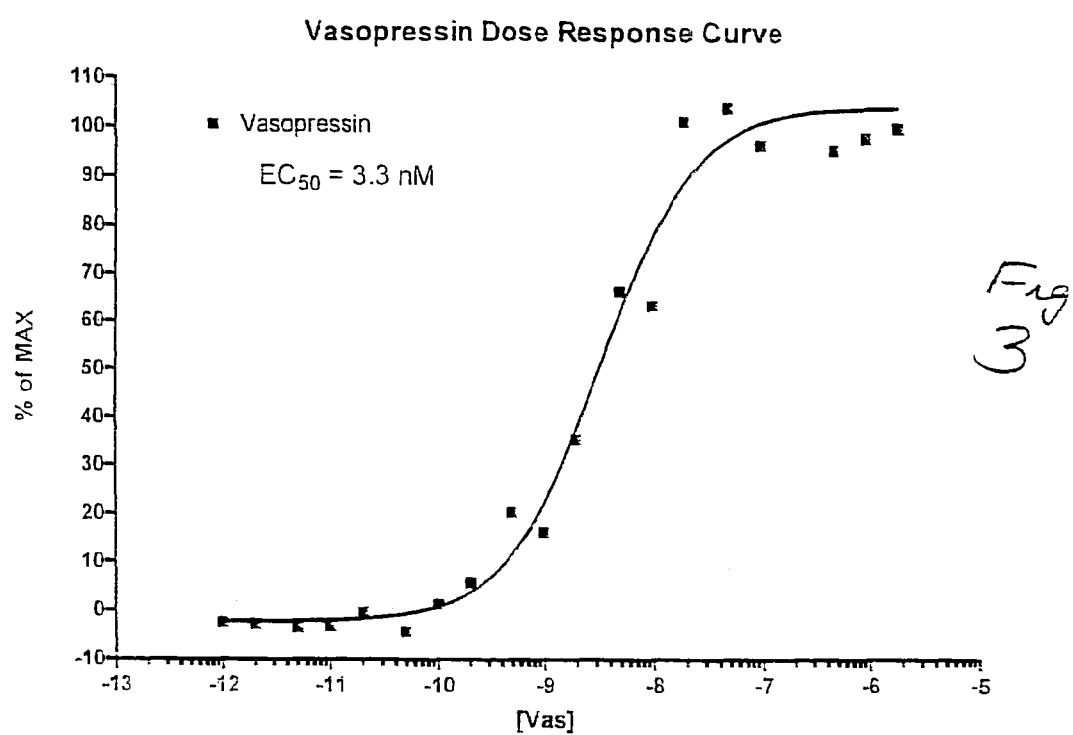
FIG. 3 shows that a dose response curve results with a different target and a different agonist as well.

Clone 41 cells were co-transfected with the AVPR2-tTA fusion construct containing the low efficiency cleavage site and the ARRB2-TEV-NIa protease fusion described supra, and assays were carried out using varying concentrations (1 pM to 2 µM) of [Arg8] vasopressin, an agonist for AVPR2. The data, presented in FIG. 3, shows a dose-response curve for this agonist, with an EC50 of 3.3 nM, which agrees with previously published data (Oakley, R., et. al., *Assay and Drug Development Technologies*, 1:21-30, (2002)). The maximal response resulted in an approximately 40-fold induction of reporter gene expression over the background level.

Example 11

A similar set of constructs were made to establish an assay for the G protein coupled serotonin receptor 1a (HTR1A). The HTR1A coding region (Genbank Accession Number: NM_000524) (SEQ ID NO: 26) was modified to place an EcoRI site at the 5' end and replace the stop codon with a BamHI site using PCR with the primers

```
    gaattcatgg atgtgctcag ccctgg     (SEQ ID NO: 27)
    and ggatccctgg cggcagaact tacac.     (SEQ ID NO: 28)
```

The modified HTR1A coding region was ligated into the AVPR2-tTA constructs described supra, which had been cut with EcoRI and BamHI. This replaced the entire coding sequence of AVPR2 with the coding sequence of HTR1A. The resulting construct will be referred to as "HTR1A-tTA" hereafter.

Clone 41 cells were co-transfected with the HTR1A-tTA fusion construct containing the low efficiency cleavage site and the ARRB2-TEV-NIa protease fusion construct described supra, and assays were carried out using 10 µM 8-hydroxy-DPAT HBr (OH-DPAT), an agonist for the HTR1A, as well as with 10 µM serotonin, a natural agonist for HTR1A. The assays were carried out as described, supra. The maximal response to OH-DPAT resulted in a 6.3-fold induction of reporter gene expression over background level and the maximal response to serotonin resulted in a 4.6-fold induction of reporter gene expression over background level.

Example 12

Similar constructs were made to establish an assay for the G protein coupled m2 muscarinic acetylcholine receptor (CHRM2). The CHRM2 coding region (Genbank Accession Number: NM_000739) (SEQ ID NO: 29) was modified to place an EcoRI site at the 5' end and replace the stop codon with a BglII site using PCR with the primers

```
    gaattcatga ataactcaac aaactcc     (SEQ ID NO: 30)
    and agatctcctt gtagcgccta tgttc.      (SEQ ID NO: 31)
```

The modified CHRM2 coding region was ligated into the AVPR2-tTA constructs described supra, which had been cut with EcoRI and BamHI. This replaced the entire coding sequence of AVPR2 with the coding sequence of CHRM2.

Clone 41 cells were co-transfected with the CHRM2-tTA fusion construct containing the high efficiency cleavage site and the ARRB2-TEV-NIa protease fusion described supra, where the ARRB2-protease fusion protein was expressed under the control of the Herpes Simplex Virus thymidine kinase (HSV-TK) promoter, and assays were carried out using 10 μM carbamylcholine Cl (carbochol), an agonist for CHRM2, as described supra. The maximal response to carbochol resulted in a 7.2-fold induction of reporter gene expression over background.

Example 13

α Constructs were also made to establish an assay for the G protein coupled chemokine (C-C motif) receptor 5 (CCR5). The CCR5 coding region (Genbank Accession Number: NM_000579) (SEQ ID NO: 32) was modified to place Not I site at the 5' end and replace the stop codon with a BamHI site using PCR with the primers

```
gcggccgcat ggattatcaa gtgtcaagtc c  (SEQ ID NO: 33)
and ggatccctgg cggcagaact tacac.         (SEQ ID NO: 34)
```

The CCR5 coding region was also modified to place a BsaI site at the 5' end which, when cut, leaves a nucleotide overhang which is compatible with EcoRI cut DNA using the primers

```
                                     (SEQ ID NO: 35)
    ggtctccaat tcatggatta tcaagtgtca agt
    and (SEQ ID NO: 36)
    gacgacagcc aggtacctat c.
```

The first modified coding region was cut with ClaI and BamHI and the second was cut with BsaI and ClaI. Both fragments were ligated into the AVPR2-tTA constructs described supra, which had been cut with EcoRI and BamHI. This replaced the entire coding sequence of AVPR2 with the coding sequence of CCR5.

The CCR5-tTA fusion construct containing the low efficiency cleavage site was transfected into "clone 34" cells, which are a derivative of the HEK cell line "clone 41" described supra, but which contain a stably integrated ARRB2-TEV-NIa protease fusion gene under the control of the CMV promoter. Assays were carried out using 1 μg/ml "Regulated on Activation, Normal T-Cell Expressed and Secreted" (RANTES), a known agonist for CCR5. The maximal response to RANTES, measured as described supra resulted in an approximately 40-fold induction of reporter gene expression over the background.

Example 14

Next, a set of constructs were made to establish an assay for the G protein coupled dopamine 2 receptor (DRD2). The DRD2 coding region (Genbank Accession Number: NM_000795) (SEQ ID NO: 37) was modified to place an EcoRI site at the 5' end and replace the stop codon with a BglII site using PCR with the primers

```
    gaattcatgg atccactgaa tctgtcc     (SEQ ID NO: 38)
    and agatctgcag tggaggatct tcagg.      (SEQ ID NO: 39)
```

The modified DRD2 coding region was ligated into the AVPR2-tTA constructs described supra, cut with EcoRI and BamHI. This replaced the entire coding sequence of AVPR2 with the coding sequence of DRD2.

Clone 41 cells were co-transfected with the DRD2-tTA fusion construct containing the medium efficiency cleavage site and the ARRB2-TEV-NIa protease fusion described supra, and assays were carried out using 10 μM dopamine HCl (dopamine), an agonist for DRD2. Results were measured as in the assays described supra. The maximal response to dopamine resulted in a 2.7-fold induction of reporter gene expression over the background.

Example 15

These experiments were designed to demonstrate enhancements of the assay using arrestin variants that bind agonist-occupied GPCRs more stably. First, a fusion of the TEV NIa protease to β-arrestin-1 (ARRB1) was constructed. The coding region of ARRB1 (Genbank Accession Number: NM_004041) (SEQ ID NO: 40) was modified to place an Asp718 site at the 5' end and replace the stop codon with a BamHI site using PCR with the primers

```
                                     (SEQ ID NO: 41)
    ggtaccatgg gcgacaaagg gacgcgagtg
    and (SEQ ID NO: 42)
    ggatcctctg ttgttgagct gtggagagcc tgtaccatcc
    tcctcttc.
```

The resulting modified ARRB1 coding region was cut with Asp718 and EcoRI and with EcoRI and BamHI, while the modified TEV NIa-Pro coding region described supra was cut with BglII and NotI. All three fragments were ligated into a commercially available pcDNA3 expression vector, which had digested with Asp718 and NotI.

Clone 41 cells were co-transfected with the DRD2-tTA fusion construct containing the medium efficiency cleavage site and the ARRB1-TEV-NIa protease fusion, and assays were carried out using 10 μM dopamine HCl (dopamine), an agonist for the D2 receptor, as described supra. The maximal response to dopamine resulted in a 2.1-fold induction of reporter gene expression over the background.

Truncation of ARRB1 following amino acid 382 has been reported to result in enhanced affinity for agonist-bound GPCRs, independent of GRK-mediated phosphorylation (Kovoor A., et. al., *J. Biol. Chem.*, 274(11):6831-6834 (1999)). To demonstrate the use of such a "constitutively active" arrestin in the present assay, the coding region of β-arrestin-1 was modified to place an Asp718 site at the 5' end and a BamHI site after amino acid 382 using PCR with SEQ ID NO: 41, supra and

```
ggatccattt gtgtcaagtt ctatgag.       (SEQ ID NO: 43)
```

This results in a an ARRb1 coding region which is 36 amino acids shorter than the full-length coding region. The resulting modified ARRB1 coding region, termed "ARRB1 (Δ383)", was cut with Asp718 and EcoRI and with EcoRI and BamHI, while the modified TEV NIa-Pro coding region described supra was cut with BglII and NotI. All three fragments were ligated into a commercially available pcDNA3 expression vector, digested with Asp718 and NotI.

Clone 41 cells were co-transfected with the DRD2-tTA fusion construct containing the medium efficiency cleavage site and the ARRB1 (Δ383)-TEV-NIa protease fusion, and assays were carried out using 10 μM dopamine HCl (dopamine), an agonist for the DRD2 receptor, as described supra.

The maximal response to dopamine resulted in an 8.3-fold induction of reporter gene expression over the background.

To examine the effect of a comparable truncation of the ARRB2 coding region the coding region of ARRB2 was modified to place an Asp718 site at the 5' end and replaced 81 nucleotides at the 3' end with a BamHI site using PCR with the primers

```
ggtaccatgg gggagaaacc cgggacc      (SEQ ID NO: 44)
and ggatcctgtg gcatagttgg tatc.        (SEQ ID NO: 45)
```

This results in a ARRB2 coding region which is 27 amino acids shorter than the full-length coding region. The resulting modified ARRB2 coding region was cut with Asp718 and BamHI, while the modified TEV NIa-Pro coding region described supra was cut with BglII and NotI. Both fragments were ligated into a commercially available pcDNA3 expression vector, digested with Asp718 and NotI.

Clone 41 cells were co-transfected with the DRD2-tTA fusion construct containing the medium efficiency cleavage site and the ARRB2 (Δ383)-TEV-NIa protease fusion, and assays were carried out using 10 μM dopamine HCl (dopamine), an agonist for the DRD2 receptor, as described supra. The maximal response to dopamine resulted in a 2.1-fold induction of reporter gene expression over the background.

Figure 4:
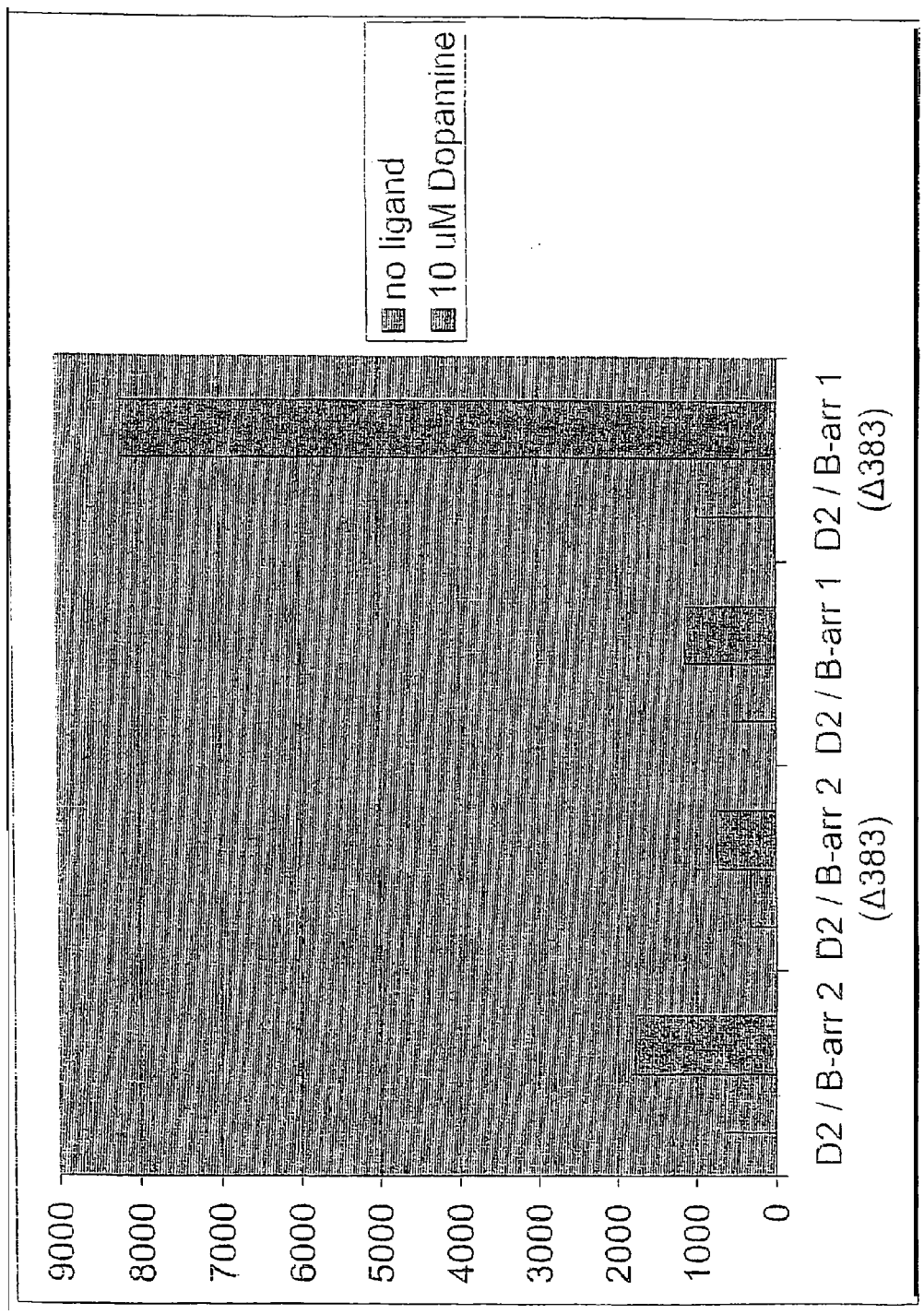
FIG. 4 depicts results obtained in accordance with the invention, using the D2 dopamine receptor.

These results, presented in FIG. 4, demonstrate that DRD2 dopamine receptor assay shows the highest signal-to-background ratio using the arrestin variant ARRB1 (Δ383).

Example 16

This set of experiments was carried out to demonstrate enhancements of the assay using receptor modifications that are designed to increase affinity for the interacting protein. In this example, the C-terminal tail domain of a test receptor was replaced with the corresponding tail domain from AVPR2, a receptor known to bind arrestins with high affinity. In these examples the fusion junction was made 15-18 amino acids after the conserved NPXXY motif at the end of the seventh transmembrane helix, which typically corresponds to a position immediately after a putative palmitoylation site in the receptor C-terminus.

First, PCR was used to produce a DNA fragment encoding the C-terminal 29 amino acids from AVPR2, followed by the low efficiency TEV cleavage site and tTA transcription factor. The fragment was also designed such that the first two amino acids (Ala, A and Arg, R) are encoded by the BssHII restriction site GCGCGC. This was accomplished by amplifying the AVPR2-tTA construct with the low efficiency cleavage site described supra with the primers

```
                                   (SEQ ID NO: 46)
tgtgcgcgcg gacgcacccc acccagcctg ggt
and (SEQ ID NO: 11)
ctcgagagat cctcgcgccc cctacccacc.
```

Next, the coding region of the DRD2 was modified to place an EcoRI site at the 5' end and to insert a BssHII site after the last amino acid in the coding region (Cys-443). This was done using PCR with the primers

```
                                   (SEQ ID NO: 47)
gaattcatgg atccactgaa tctgtcc
and (SEQ ID NO: 48)
tgtgcgcgcg cagtggagga tcttcaggaa ggc.
```

The resulting modified D2 coding region was cut with EcoRI and BssHII and the resulting AVPR2 C-terminal tail-low efficiency cleavage site-tTA fragment was cut with BssHII and BamHI. Both fragments were ligated into the AVPR2-low efficiency cleavage site-tTA construct described supra, cut with EcoRI and BamHI.

Clone 41 cells were co-transfected with the DRD2-AVPR2 Tail-tTA fusion construct containing the low efficiency TEV cleavage site and the ARRB2-TEV-NIa protease fusion described supra, and assays were carried out using 10 μM dopamine HCl (dopamine), an agonist for the DRD2 receptor. The maximal response to dopamine resulted in an approximately 60-fold induction of reporter gene expression over the background.

A construct was made which modified the ADRB2 receptor coding region by inserting an Asp718 site at the 5' end and by placing a BssHII site after Cys-341. This was done using PCR with the primers

```
                                   (SEQ ID NO: 49)
gcggccgcca ccatgaacgg taccgaaggc cca
and (SEQ ID NO: 50)
tgtgcgcgcg cacagaagct cctggaaggc.
```

The modified ADRB2 receptor coding region was cut with EcoRI and BssHII and the AVPR2 C-terminal tail-low efficiency cleavage site-tTA fragment was cut with BssHII and BamHI. Both fragments were ligated into the AVPR2-low efficiency cleavage site-tTA construct described supra cut, with EcoRI and BamHI. The resulting construct is "ADRB2-AVPR2 Tail-tTA." (Also see published application U.S. 2002/0106379, supra, SEQ ID NO: 3 in particular.)

Clone 41 cells were co-transfected with the ADRB2-AVPR2 Tail-tTA fusion construct containing the low efficiency TEV cleavage site and the ARRB2-TEV-NIa protease fusion described supra, and assays were carried out using 10 μM isoproterenol, an agonist for the ADRB2 receptor. The maximal response to isoproterenol resulted in an approximately 10-fold induction of reporter gene expression over the background.

A construct was made which modified the kappa opioid receptor (OPRK; Genbank Accession Number: NM_000912) (SEQ ID NO: 51) coding region by placing a BssHII site after Cys-345. This was done using PCR with the primers

```
ggtctacttg atgaattcct ggcc         (SEQ ID NO: 52)
and gcgcgcacag aagtccggga aacaccg      (SEQ ID NO: 53)
```

The modified OPRK receptor coding region was cut with EcoRI and BssHII and AVPR2 C-terminal tail-low efficiency cleavage site-tTA fragment was cut with BssHII and XhoI. Both fragments were ligated into a plasmid containing the modified OPRK receptor sequence, cloned into pcDNA3.1+ at Asp718 (5') and XhoI (3'), which had been digested with EcoRI and XhoI.

Clone 41 cells were co-transfected with the OPRK-AVPR2 Tail-tTA fusion construct containing the low efficiency cleavage site and the ARRB2-TEV-NIa protease fusion described supra, and assays were carried out using 10 μM U-69593, an agonist for the OPRK. The maximal response to U-69593 resulted in an approximately 12-fold induction of reporter gene expression over the background.

Example 17

This experiment was designed to demonstrate the use of the assay to measure the activity of two test receptors simultaneously using a multiplex format.

Clone 41 cells and "clone 1H10" cells, which are cells of an HEK-293T cell line containing a stable integration of the luciferase gene under the control of a tTA-dependent promoter, were each plated on 24-well culture dishes and were transiently transfected with the chimeric ADRB2-AVPR2 Tail-tTA or the DRD2-AVPR2 Tail-tTA fusion constructs described supra, respectively. Transient transfections were performed using 100 μl of media, 0.4 μg of DNA and 2 μl of FuGene reagent per well. After 24 hr of incubation, Clone 41 cells expressing ADRB2-AVPR2 Tail-tTA and clone 1H 10 cells expressing DRD2-AVPR2 Tail-tTA were trypsinized, mixed in equal amounts, and replated in 12 wells of a 96-well plate. Triplicate wells were incubated without drug addition or were immediately treated with 1 μM isoproterenol, 1 μM dopamine, or a mixture of both agonists at 1 μM. Cells were assayed for reporter gene activity approximately 24 hours after ligand addition. Medium was discarded, cells were lysed in 4011 lysis buffer [100 mM potassium phosphate pH 7.8, 0.2% Triton X-100] and the cell lysate was assayed for beta-galactosidase and for luciferase activity using commercially available luminescent detection reagents.

Figure 5A:
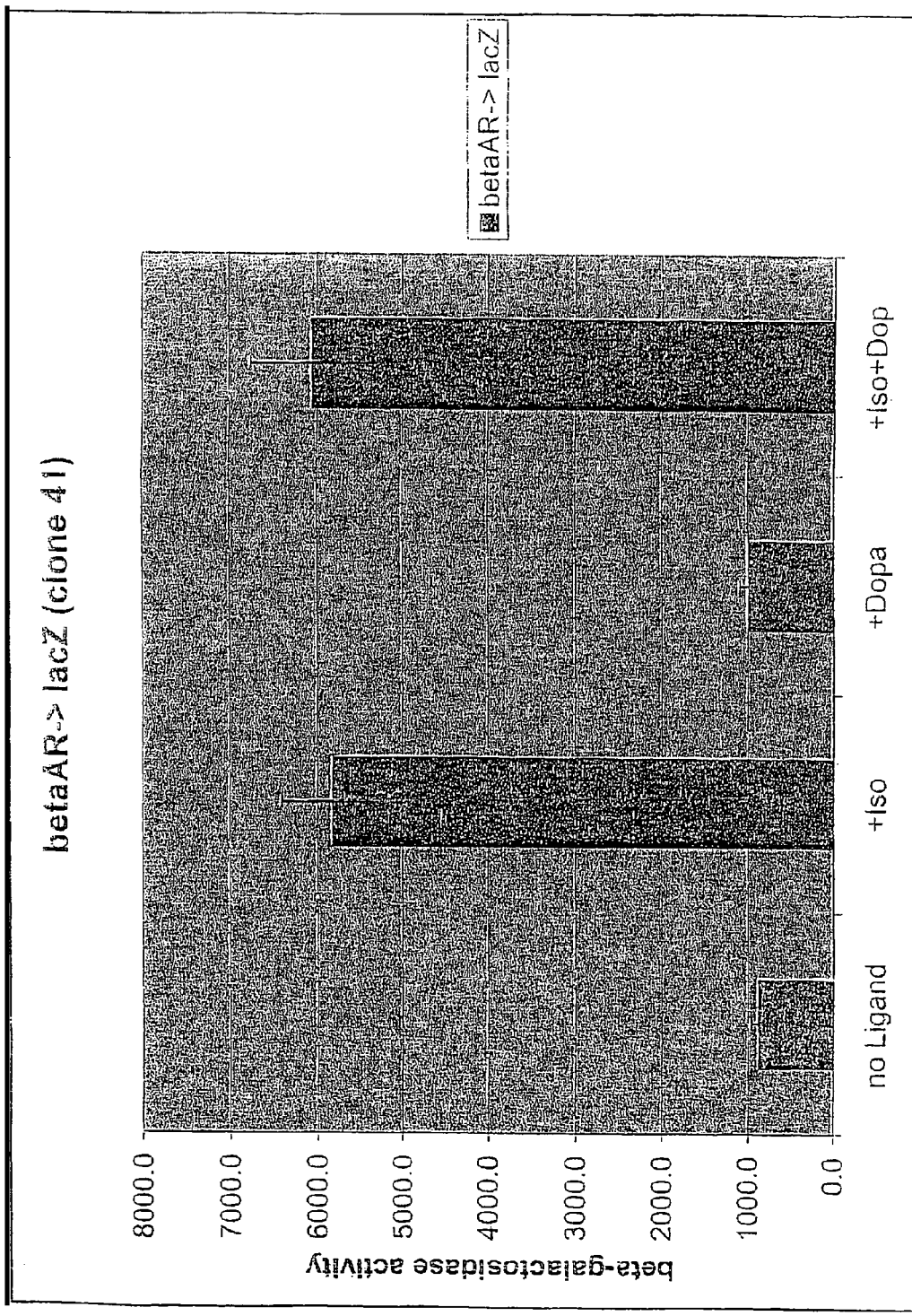
FIGS. 5a and 5b illustrate results of an assay which shows that two molecules can be studied simultaneously.
Figure 5B:
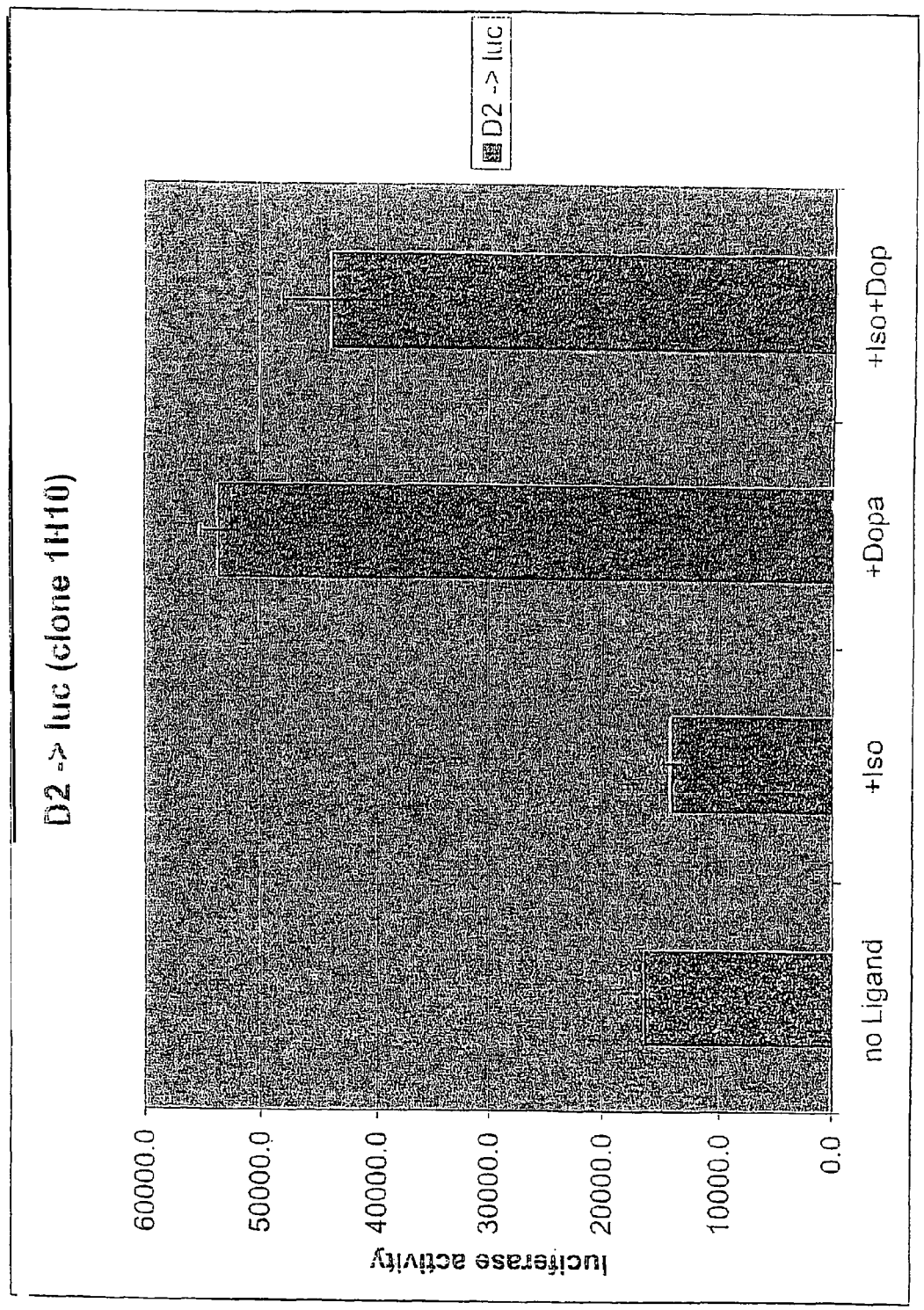

The results are presented in FIGS. 5A and 5B. Treatment with isoproterenol resulted in an approximately seven-fold induction of beta-galactosidase reporter gene activity, whereas luciferase activity remained unchanged. Treatment with dopamine resulted in a 3.5-fold induction of luciferase activity, while beta-galactosidase activity remained unchanged. Treatment with both isoproterenol and dopamine resulted in seven-fold and three-fold induction of beta-galactosidase and luciferase activity, respectively.

Example 18

This experiment was designed to demonstrate the use of the assay to measure the activity of two test receptors simultaneously using a multiplex format.

Figure 6:
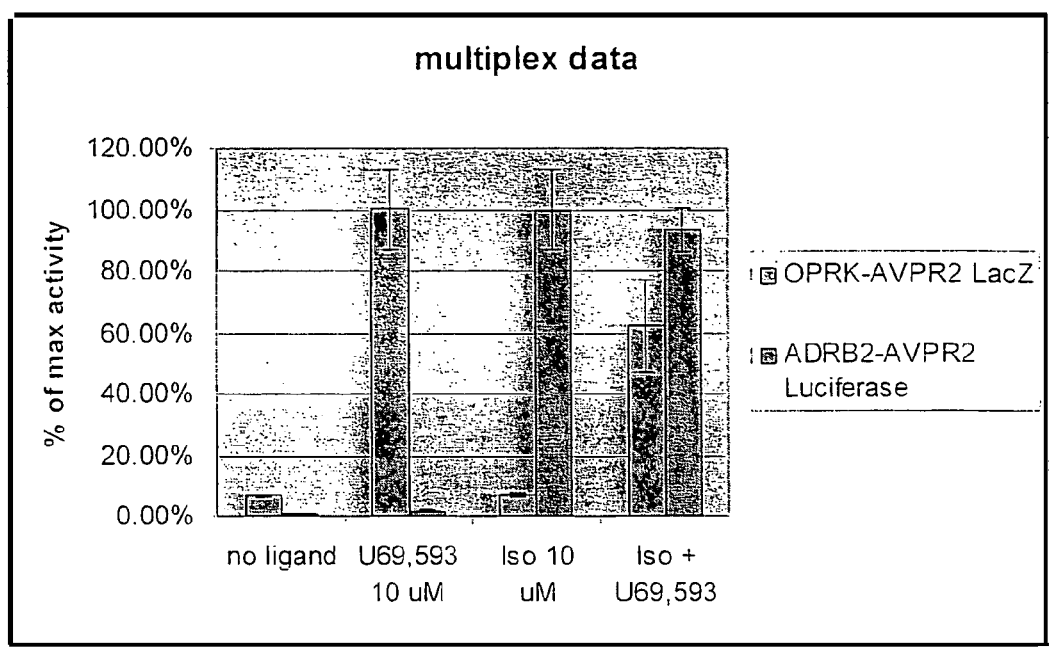
FIG. 6 sets forth the result of another "multiplex" assay, i.e., one where two molecules are studied simultaneously.

"Clone 34.9" cells, which are a derivative of clone 41 cells and containing a stably integrated ARRB2-TEV NIa protease fusion protein gene, were transiently transfected with the chimeric OPRK-AVPR2 Tail-TEV-NIa-Pro cleavage (Leu)-tTA fusion construct described supra. In parallel, "clone HTL 5B8.1" cells, which are an HEK-293T cell line containing a stable integrated luciferase gene under the control of a tTA-dependent promoter, were transiently transfected with the ADRB-AVPR2 Tail-TEV-NIa-Pro cleavage (Leu)-tTA fusion construct described supra. In each case 5×10⁵ cells were plated in each well of a 6-well dish, and cultured for 24 hours in DMEM supplemented with 10% fetal bovine serum, 2 mM L-Glutamine, 100 units/ml penicillin, 500 μg/ml G418, and 3 μg/ml puromycin. Cells were transiently transfected with 100 μl of DMEM, 0.5 μg of OPRK-AVPR2 Tail-TEV-NIa-Pro cleavage (Leu)-tTA DNA, and 2.5 μl Fugene ("clone 34.9 cells") or with 100 μl of DMEM, 0.5 μg of ADRB2-AVPR2 Tail-TEV-NIa-Pro cleavage (Leu)-tTA DNA, 0.5 μg of ARRB2-TEV NIa Protease DNA and 5 μl Fugene ("clone HTL 5B8.1 cells"). Transiently transfected cells were cultured for about 24 hours, and were then trypsinized, mixed in equal amounts and replated in wells of a 96 well plate. Cell were incubated for 24 hours before treatment with 10 μM U-69593, 10 μM isoproterenol or a mixture of both agonists at 10 μM. Sixteen wells were assayed for each experimental condition. After 24 hours, cells were lysed and the activity of both beta-galactosidase and luciferase reporter genes were assayed as described supra. The results are presented in FIG. 6. Treatment with U-69593 resulted in an approximately 15-fold induction of beta-galactosidase reporter gene activity, whereas luciferase activity remained unchanged. Treatment with isoproterenol resulted in a 145-fold induction of luciferase activity, while beta-galactosidase activity remained unchanged. Treatment with both U-69593 and isoproterenol resulted in nine-fold and 136-fold induction of beta-galactosidase and luciferase activity, respectively.

Example 19

This experiment was carried out to demonstrate the use of a different transcription factor and promoter in the assay of the invention.

A fusion construct was created, comprising DNA encoding AVPR2, fused in frame to a DNA sequence encoding the amino acid linker GSENLYFQLR (SEQ ID NO: 54) which included the low efficiency cleavage site for TEV NIa-Pro described supra, fused in frame to a DNA sequence encoding amino acids 2-147 of the yeast GAL4 protein (GenBank Accession Number P04386) (SEQ ID NO: 55) followed by a linker, i.e., of the sequence PELGSASAELTMVF (SEQ ID NO: 56), followed by amino acids 368-549 of the murine nuclear factor kappa-B chain p65 protein (GenBank Accession Number NM_009045) (SEQ ID NO: 57). The CMV promoter was placed upstream of the AVPR2 coding region and a polyA sequence was placed downstream of the GAL4-NFkB region. This construct was designated AVPR2-TEV-NIa-Pro cleavage (Leu)-GAL4.

HUL 5C1.1 is a derivative of HEK-293T cells, which contain a stably integrated luciferase reporter gene under the control of a GAL4 upstream activating sequence (UAS), commercially available pFR-LUC.

This AVPR2-TEV-NIa-Pro cleavage (Leu)-GAL4 plasmid was co-transfected along with the β-arrestin2-TEV N1a Protease described supra into HUL 5C1.1 cells. About 2.5×10⁴ cells were plated into each well of a 96 well-plate, in DMEM medium supplemented with 10% fetal bovine serum, 2 mM L-Glutamine, 100 units/ml penicillin, 500 μg/ml G418, and 3 μg/ml puromycin. Cells were grown to reach 50% confluency the next day and were transfected with 10 μl per well of a mixture consisting of 85 μl of DMEM, 0.1 μg of AVPR2-TEV-Nia-Pro cleavage (Leu)-GAL4 DNA, 0.1 μg of ARRB2-TEV N1a Protease DNA, and 1 μl Fugene, which had been incubated for 15 minutes at room temperature prior to addition to the cells. Transfected cells were cultured for about 16 hours before treatment with 10 μM vasopressin. After six hours, cells were lysed and luciferase activity was assayed as described supra. Under these conditions, treatment with vasopressin resulted in a 180-fold increase in reporter gene activity.

Example 20

This set of experiments were carried out to demonstrate enhancements of the assay using further receptor modifications that are designed to increase the affinity for the interacting protein. In this example, the C-terminal tail domain of the test receptor is replaced with the corresponding tail domain of one of the following receptors: apelin J receptor—AGTRL1 (accession number: NM_005161) (SEQ ID NO: 58), gastrin-releasing peptide receptor—GRPR (accession number: NM_005314) (SEQ ID NO: 59), proteinase-activated receptor 2—F2RL1 (accession number: NM_005242) (SEQ ID NO: 60), CCR4 (accession number: NM_005508) (SEQ ID NO: 61), chemokine (C-X-C motif) receptor 4-CXCR4 (accession number: NM_003467) (SEQ ID NO: 62), and interleukin 8 receptor, beta-CXCR2/IL8b (accession number: NM_001557) (SEQ ID NO: 63).

First PCR was used to produce a DNA fragment encoding the C-terminal tail of the above receptors. These fragments were designed such that the first two amino acids (Ala, A and Arg, R) are encoded by the BssHII restriction site.

The AGTRL1 C-terminal fragment was amplified with the primers

```
tgtgcgcgcg gccagagcag gtgcgca     (SEQ ID NO: 64)
and gaggatccgt caaccacaag ggtctc.     (SEQ ID NO: 65)
```

The GRPR C-terminal fragment was amplified with the primers

```
tgtgcgcgcg gcctgatcat ccggtct     (SEQ ID NO: 66)
and gaggatccga cataccgctc gtgaca.     (SEQ ID NO: 67)
```

The F2RL1 C-terminal fragment was amplified with the primers

```
tgtgcgcgca gtgtccgcac tgtaaagc    (SEQ ID NO: 68)
and gaggatccat aggaggtctt aacagt.     (SEQ ID NO: 69)
```

The CCR4 C-terminal fragment was amplified with the primers

```
tgtgcgcgcg gccttttttgt gctctgc    (SEQ ID NO: 70)
and gaggatccca gagcatcatg aagatc.     (SEQ ID NO: 71)
```

The CXCR2/IL8b C-terminal fragment was amplified with the primers

```
tgtgcgcgcg gcttgatcag caagggac    (SEQ ID NO: 72)
and gaggatccga gagtagtgga agtgtg.     (SEQ ID NO: 73)
```

The CXCR4 C-terminal fragment was amplified with the primers

```
tgtgcgcgcg ggtccagcct caagatc     (SEQ ID NO: 74)
and gaggatccgc tggagtgaaa acttga.     (SEQ ID NO: 75)
```

The resulting DNA fragments encoding the modified C-terminal tail domains of these receptors were cut with BssHII and BamHI and the fragments were ligated in frame to the OPRK receptor coding region, replacing the AVPR2-C-terminal tail fragment, in the OPRK-AVPR2 Tail-TEV-NIa-Pro cleavage (Leu)-tTA expression construct described supra.

HTL 5B8.1 cells described supra were co-transfected with each of the above modified OPRK coding region—TEV-NIa-Pro cleavage (Leu) tTA constructs and the β-arrestin 2—TEV NIa protease fusion described supra. About $2.5 \times 10^4$ cells per well were plated onto a 96 well-plate, in DMEM medium supplemented with 10% fetal bovine serum, 2 mM L-Glutamine, 100 units/ml penicillin, 500 µg/ml G418, and 3 µg/ml puromycin. Cells were grown to reach 50% confluency the next day and were transfected with 10 µl per well of a mixture consisting of 85 µl of DMEM, 0.25 µg of AVPR2-TEV-NIa-Pro cleavage (Leu)-GAL4 DNA, 0.25 µg of ARRB2-TEV NIa protease DNA, and 2.5 µl Fugene (a proprietary transfection reagent containing lipids and other material), which had been incubated for 15 minutes at room temperature prior to addition to the cells. Transfected cells were cultured for about 16 hours before treatment 10 µM U-69593. After six hours, cells were lysed and luciferase activity was assayed as described supra. Under these conditions, treatment with U-69593 resulted in the following relative increases in reporter gene activity for each of the modified OPRK receptors: OPRK-AGTRL1 C-terminal tail—30 fold; OPRK-GRPR C-terminal tail—312 fold; OPRK-F2RL1 C-terminal tail—69.5 fold; OPRK-CCR4 C-terminal tail—3.5 fold; OPRK-CXCR4 C-terminal tail—9.3 fold; OPRK-IL8b C-terminal tail—113 fold.

Example 21

This experiment was designed to produce a cell line that stably expressed the ARRB2-TEV NIa protease fusion protein described supra.

A plasmid was made which expressed the ARRB2-TEV NIa protease fusion protein under the control of the EF1α promoter and also expressed the hygromycin resistance gene under the control of the thymidine kinase (TK) promoter.

This plasmid was transfected into HTL 5B8.1, and clones containing a stable genomic integration of the plasmid were selected by culturing in the presence of 100 µg/ml hygromycin. Resistant clones were isolated and expanded and were screened by transfection of the ADRB2-AVPR2 Tail-TEV-NIa-Pro cleavage (Leu)-tTA plasmid described supra. Three cell lines that were selected using this procedure were designated "HTLA 4C2.10", "HTLA 2C11.6" and "HTLA 5D4". About $2.5 \times 10^4$ cells per well were plated onto a 96 well-plate, in DMEM medium supplemented with 10% fetal bovine serum, 2 mM L-Glutamine, 100 units/ml penicillin, 500 µg/ml G418, 3 µg/ml puromycin, and 100 µg/ml hygromycin. Cells were grown to reach 50% confluency the next day and were transfected with 10 µl per well of a mixture consisting of 85 µl of DMEM, 0.25 µg of ADRB2-AVPR2-TEV-NIa-Pro cleavage (Leu)-GAL4 DNA and 0.5 µl Fugene, which had been incubated for 15 minutes at room temperature prior to addition to the cells. Transfected cells were cultured for about 16 hours before treatment 10 µM isoproterenol. After six hours, cells were lysed and luciferase activity was assayed as described supra. Under these conditions, treatment with isoproterenol resulted in a 112-fold ("HTLA 4C2.10"), 56-fold ("HTLA 2C11.6") and 180-fold ("HTLA 5D4") increase in reporter gene activity in the three cell lines, respectively.

Example 22

This experiment was designed to produce a cell line that stably expressed the ARRB2-TEV NIa protease and the ADRB2-AVPR2 Tail-TEV-NIa-Pro cleavage (Leu)-tTA fusion proteins described supra.

The ARRB2-TEV NIa protease plasmid containing the hygromycin resistance gene was transfected together with the ADRB2-AVPR2 Tail-TEV-NIa-Pro cleavage (Leu)-tTA fusion protein plasmid described supra into HTL 5B8.1 cells and clones containing stable genomic integration of the plasmids were selected by culturing in the presence of 100 μg/ml hygromycin. Resistant clones were isolated and expanded, and were screened by treating with 10 μM isoproterenol and measuring the induction of reporter gene activity as described supra. Three cell lines that were selected using this procedure were designated "HTLAR 1E4", "HTLAR 1C10" and "HTLAR 2G2". Treatment with isoproterenol for 6 hours resulted in a 208-fold ("HTLAR 1E4"), 197-fold ("HTLAR 1C10") and 390-fold ("HTLAR 2G2") increase in reporter gene activity in the three cell lines, respectively.

Example 23

This experiment was designed to demonstrate the use of the assay to measure the activity of the receptor tyrosine kinase epidermal growth factor receptor (EGFR).

A first fusion construct was created, comprising DNA encoding the human EGFR, which can be found at GenBank under the Accession Number NM_005228 (SEQ ID NO: 76), fused in frame to a DNA sequence encoding amino acids 3-335 of the tetracycline-controlled transactivator tTA, described supra. Inserted between these sequences is a DNA sequence encoding the amino acid sequence GGSGSENLYFQL (SEQ ID NO: 77) which includes the low efficiency cleavage site for TEV NIa-Pro, ENLYFQL (SEQ ID NO: 14), described supra. The CMV promoter was placed upstream of the Epidermal Growth Factor Receptor coding region, and a polyA sequence was placed downstream of the tTA region. This construct is designated EGFR-TEV-NIa-Pro cleavage (Leu)-tTA.

A second fusion construct was created, comprising DNA encoding the two SH2 domains of human Phospholipase C Gamma 1, corresponding to amino acids 538-759 (GeneBank accession number NP_002651.2) (SEQ ID NO: 78) fused in frame to a DNA sequence encoding the catalytic domain of mature TEV NIa protease, described supra, corresponding to amino acids 2040-2279 (GeneBank accession number AAA47910) (SEQ ID NO: 79). Inserted between these sequences is a linker DNA sequence encoding the amino acids NSSGGNSGS (SEQ ID NO: 80). The CMV promoter was placed upstream of the PLC-Gamma SH2 domain coding sequence and a polyA sequence was placed downstream of the TEV NIa protease sequence. This construct is designated PLC Gamma1-TEV.

Figure 7:
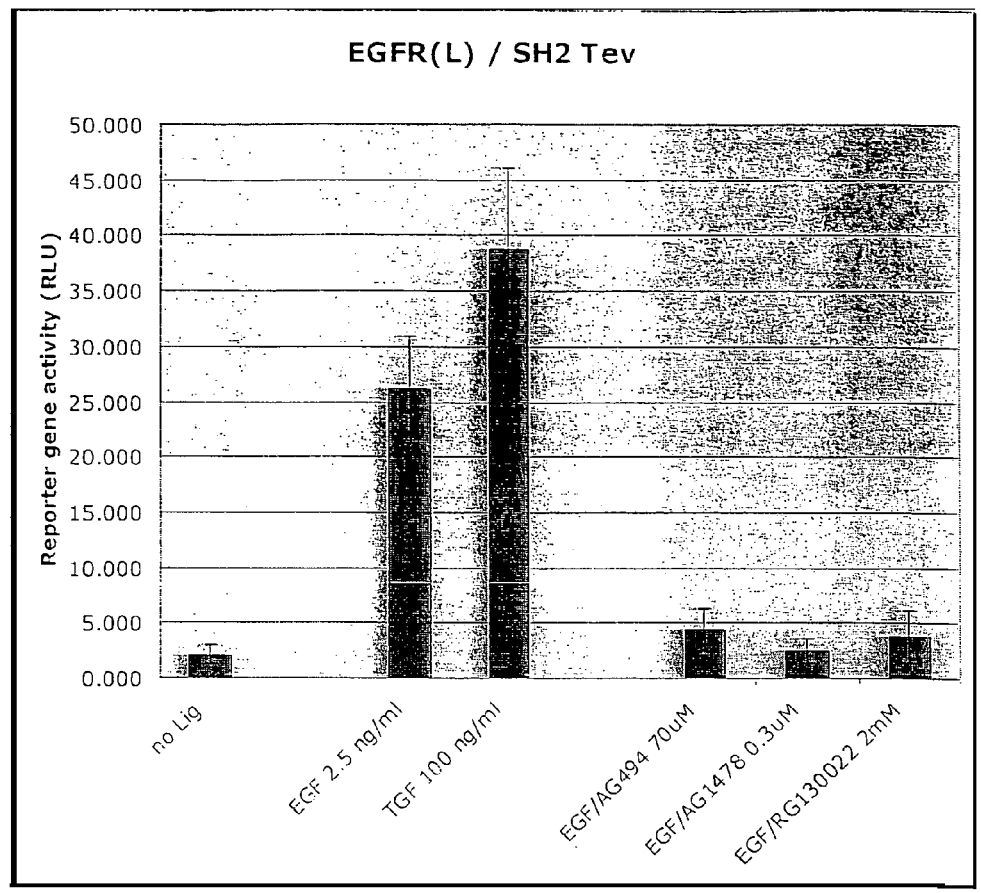
FIG. 7 presents data obtained from assays measuring EGFR activity.

The EGFR-TEV-NIa-Pro cleavage (Leu)-tTA and PLC Gamma1-TEV fusion constructs were transfected into clone HTL5B8.1 cells described supra. About 2.5×10$^4$ cells were plated into each well of a 96 well-plate, in DMEM medium supplemented with 10% fetal bovine serum, 2 mM L-Glutamine, 100 units/ml penicillin, 500 μg/ml G418, and 3 μg/ml puromycin. Cells were grown to reach 50% confluency the next day and were transfected with 15 μl per well of a mixture consisting of 100 μl of DMEM, 0.4 μg of pcDNA3 DNA ("carrier" vector DNA), 0.04 μg of EGFR-TEV-NIa-Pro cleavage (Leu)-tTA DNA, 0.04 μg of PLC Gamma1-TEV DNA, and 2 μl Fugene (a proprietary transfection reagent containing lipids and other material), which had been incubated for 15 minutes at room temperature prior to addition to the cells. Transfected cells were cultured for about 16 hours before treatment with specified receptor agonists and inhibitors. After six hours, cells were lysed and luciferase activity was assayed as described supra. Results are shown in FIG. 7.

The addition of 2.5 ng/ml human Epidermal Growth Factor (corresponding to the EC80 for this ligand) resulted in a 12.3 fold increase of luciferase reporter gene activity, while addition of 100 ng/ml human Transforming Growth Factor—Alpha resulted in an 18.3 fold increase. Prior treatment with tyrosine kinase inhibitors (70 μM AG-494; 0.3 μM AG-1478; 2 mM RG-130022) before addition of human Epidermal Growth Factor blocked the induction of reporter gene activity.

Example 24

This experiment was designed to demonstrate the use of the assay to measure the activity of the human Type I Interferon Receptor.

A fusion construct was created, comprising DNA encoding human Interferon Receptor I (IFNAR1) (557 amino acids), which can be found in Genbank under Accession Number NM_000629 (SEQ ID NO: 81), fused in frame to a DNA sequence encoding amino acids 3-335 of the tetracycline controlled transactivator tTA, described supra. Inserted between these sequences is a DNA sequence encoding the amino acid sequence GSENLYFQL (SEQ ID NO: 82) which includes the low efficiency cleavage site for TEV NIa-Pro, ENLYFQL (SEQ ID NO: 14), described supra. The CMV promoter was placed upstream of the Human Interferon Receptor I (IFNAR1) coding region, and a poly A sequence was placed downstream of the tTA region. This construct is designated IFNAR1-TEV-NIa-Pro cleavage (L)-tTA.

A second fusion construct was created, using DNA encoding Human Interferon Receptor 2, splice variant 2 (IFNAR2.2) (515 amino acids), which can be found at Genbank, under Accession Number L41942 (SEQ ID NO: 83), fused in frame to a DNA sequence encoding the catalytic domain of the TEV NIa protease, described supra, corresponding to amino acids 2040-2279 (GenBank accession number AAA47910) (SEQ ID NO: 84). Inserted between these sequences is a DNA sequence encoding the amino acid sequence RS (Arg-Ser). The CMV promoter region was placed upstream of the Human Interferon Receptor 2 (IFNAR2.2) coding region, and a poly A sequence was placed downstream of the TEV region. This construct is designated IFNAR2.2-TEV.

Expression constructs were also generated in which the genes for Human Signal Transducer and Activator of Transcription 1 (STAT1), found in Genbank, under Accession Number NM_007315 (SEQ ID NO: 85), Human Signal Transducer and Activator of Transcription 2 (STAT2) found in Genbank, under Accession Number NM_005419 (SEQ ID NO: 86), were expressed under the control of the CMV promoter region. These constructs were designated CMV-STAT1 and CMV-STAT2 respectively.

Figure 8:
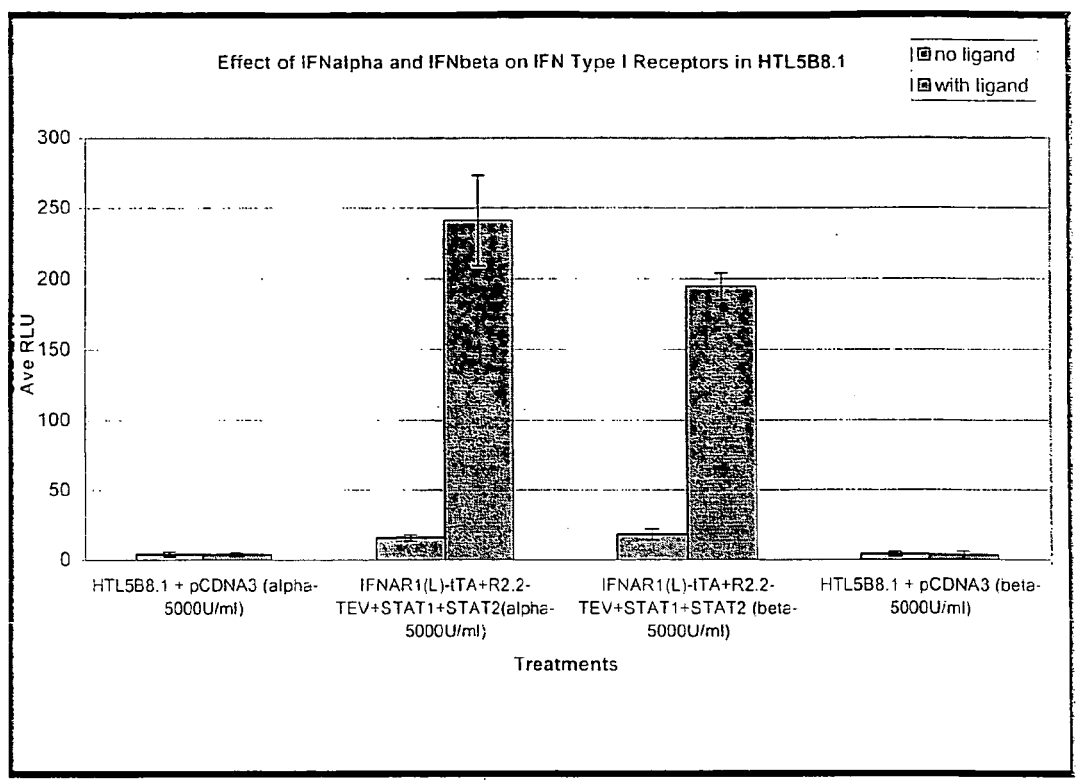
FIG. 8 presents data obtained from assays in accordance with the invention, designed to measure the activity of human type I interferon receptor.
Figure 9:
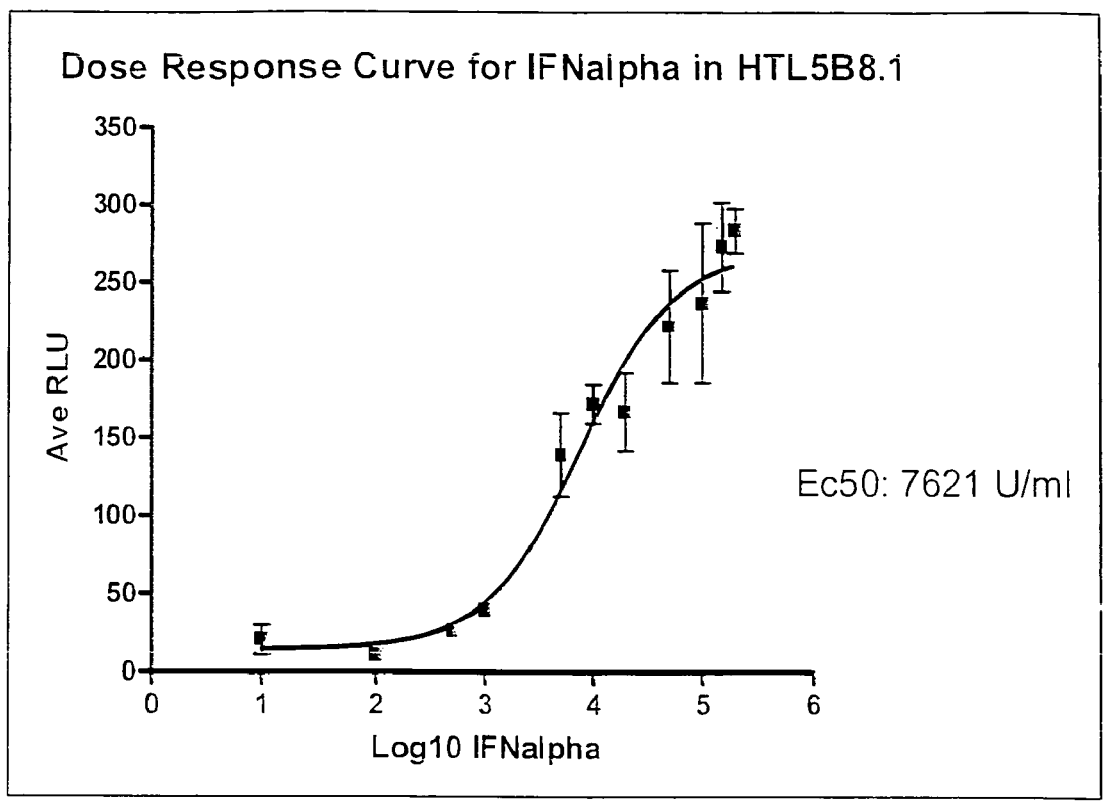
FIG. 9 elaborates on the results in FIG. 7, showing a dose response curve for IFN-α in the cells used to generate FIG. 7.

The IFNAR1-TEV-NIa-Pro cleavage (L)-tTA and IFNAR2.2-TEV fusion constructs, together with CMV-STAT1 and CMV-STAT2 were transiently transfected into HTL5B8.1 cells described supra. About 2.5×10$^4$ cells were seeded in each well of a 96 well plate and cultured in DMEM medium supplemented with 10% fetal bovine serum, 2 mM L-glutamine, 100 units/ml penicillin, 100 μg/ml G418, and 5 μg/ml puromycin. After 24 hours of incubation, cells were transfected with 15 ng of each IFNAR1-TEV-NIa-Pro cleavage (L)-tTA, IFNAR2.2-TEV, CMV-STAT1 and CMV-STAT2 DNA, or with 60 ng control pcDNA plasmid, together with 0.3 μl Fugene per well. Transfected cells were cultured for 8-20 hours before treatment with 5000 U/ml human interferon-alpha or 5000 U/ml human interferon-beta. At the time of interferon addition, medium was aspirated and replaced with 293 SFM II media supplemented with 2 mM L-glutamine, 100 units/ml penicillin, 3 µg/ml puromycin and 500 µg/ml of G418. Interferon-treated cells were cultured for an additional 18-20 hours before they were assayed for luciferase reporter gene activity as described supra. Results are shown in FIG. 8. Treatment with 5000 U/ml IFN-α resulted in 15-fold increase in reporter gene activity, while treatment with 5000 U/ml IFN-β resulted in a 10-fold increase. Interferon treatment of HTL5B8.1 cells transfected with the control plasmid pcDNA3 had no effect on reporter gene activity. FIG. 9 shows a dose-response curve generated for IFN-α in HTL5B8.1 cells transfected with IFNAR1(EN-LYFQL(SEQ ID NO:14))-tTA, IFNAR2.2-TEV, STAT1 and STAT2 expression constructs as described supra.

Example 25

This experiment was designed to demonstrate the use of the assay to measure the activity of the human Type I Interferon Receptor using a different transcription factor and a different cell line.

A fusion construct was created, using DNA encoding Human Interferon Receptor I (IFNAR1), fused in frame to a DNA sequence encoding the GAL4-NF-κB-fusion, described supra. Inserted between these sequences is a DNA sequence encoding the amino acid sequence GSENLYFQL (SEQ ID NO: 87), which includes the low efficiency cleavage site for TEV NIa-Pro, ENLYFQL (SEQ ID NO: 14), described supra. The CMV promoter was placed upstream of the Human Interferon Receptor I (IFNAR1) coding region, and a poly A sequence was placed downstream of the GAL4-NF-κB region. This construct is designated IFNAR1-TEV-NIa-Pro cleavage (L)-GAL4-NF-κB.

Figure 10:
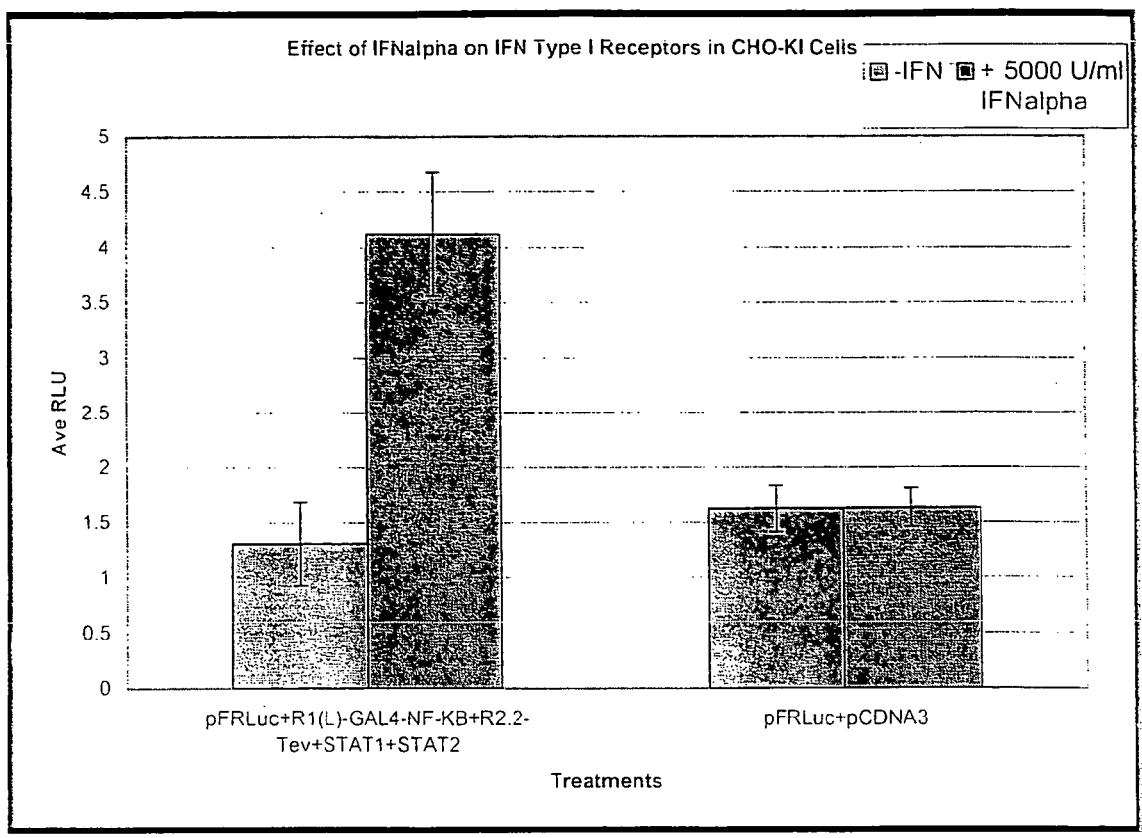
FIG. 10 shows the results of additional experiments where a different transcription factor, and a different cell line, were used.

CHO-K1 cells were then transiently transfected with a mixture of five plasmids: IFNAR1-TEV-NIa-Pro cleavage (L)-GAL4-NF-κB, IFNAR2.2-TEV, CMV-STAT1, CMV-STAT2 and pFR-Luc, a luciferase reporter gene plasmid under the control of a GAL4-dependent promoter. About $1.0 \times 10^4$ cells per well were seeded in a 96 well plate 24 hours prior to transfections in DMEM medium supplemented with 10% fetal bovine serum, 2 mM L-glutamine, 100 units/ml penicillin. Cells were transfected the following day with 10 ng of reporter plasmid (pFR-Luc), plus 20 ng of each of the expression constructs described supra or with 10 ng reporter plasmid plus 80 ng of control pcDNA3 plasmid, together with 0.3 µl Fugene per well. Transfected cells were cultured for 8-20 hours before treatment with 5000 U/ml human interferon-alpha. At the time of interferon addition, medium was aspirated and replaced with DMEM media supplemented with 2 mM L-glutamine, 100 units/ml penicillin. Interferon-treated cells were cultured for an additional 6 hours before they were assayed for luciferase reporter gene activity as described supra. Results are shown in FIG. 10. IFN-α treatment of CHO-K1 cells transfected with the reporter, IFNAR and STAT constructs resulted in 3-fold increase in reporter gene activity, while interferon treatment of cells transfected with the reporter and control plasmids had no effect on reporter gene activity.

Example 26

This set of experiments was carried out to demonstrate additional enhancements of the assay using receptor modifications designed to increase the affinity of the test receptor for the interacting protein. In these examples, the fusion junction between the test receptor and a C-terminal tail domain of GRPR (Genbank Accession Number: NM_005314) (SEQ ID NO: 59) was made 17-23 amino acids after the conserved NPXXY motif at the end of the seventh transmembrane helix.

First, PCR was used to produce a DNA fragment encoding the C-terminal 42 amino acids from GRPR beginning 2 amino acids after the putative palmitoylation site (hereafter referred to as GRPR 42aa). The fragment was designed such that the first amino acid of the C-terminal tail is preceded by two amino acids (Ser, S and Arg, R) which are encoded by the XbaI restriction site TCTAGA, and the stop codon is replaced by two amino acids (Gly, G and Ser, S) which are encoded by a BamHI restriction site GGATCC. This was accomplished by amplifying a plasmid containing the GRPR coding region with primers

```
tctagaggcctgatcatccggtctcac    (SEQ ID NO: 88)
and gaggatccgacataccgctcgtgaca     (SEQ ID NO: 67)
```

Next the coding region of OPRK (Genbank Accession Number: NM_000912) (SEQ ID NO: 51) was modified to place insert an XbaI site after Pro-347. This was done using PCR with the primers

```
ggtctacttgatgaattcctggcc       (SEQ ID NO: 52)
and tctagatggaaaacagaagtcccggaaac  (SEQ ID NO: 89)
```

In addition, the coding region of ADRA1A (Genbank Accession Number: NM_000680) (SEQ ID NO: 90) was modified to insert an XbaI site after Lys-349. This was done using PCR with the primers

```
ctcggatatctaaacagctgcatcaa     (SEQ ID NO: 91)
and tctagactttctgcagagacactggattc  (SEQ ID NO: 92)
```

In addition, the coding region of DRD2 (Genbank Accession Number: NM_000795) (SEQ ID NO: 37) was modified to insert two amino acids (Leu and Arg) and an XbaI site after Cys-343. This was done using PCR with the primers

```
gaattcatggatccactgaatctgtcc    (SEQ ID NO: 38)
and tctagatcgaaggcagtggaggatcttcagg (SEQ ID NO: 93)
```

The modified OPRK receptor coding region was cut with EcoRI and XbaI and the GRPR 42aa C-terminal tail fragment was cut with XbaI and BamHI. Both fragments were ligated into a plasmid containing the OPRK receptor with the AVPR2 C-terminal tail-low-efficiency cleavage site-tTA described supra which had been digested with EcoRI and BamHI.

The modified ADRA1A receptor coding region was cut with EcoRV and XbaI and the OPRK-GRPR 42aa Tail-tTA fusion construct containing the low efficiency cleavage site was cut with XbaI and XhoI. Both fragments were ligated into a plasmid containing the ADRA1A receptor which had been digested with EcoRV and XhoI.

The modified DRD2 receptor coding region was cut with EcoRI and XbaI and the OPRK-GRPR 42aa Tail-tTA fusion construct containing the low efficiency cleavage site was cut with XbaI and XhoI. Both fragments were ligated into a pcDNA6 plasmid digested with EcoRI and XhoI HTLA 2C11.6 cells, described supra, were transfected with OPRK-GRPR 42aa Tail-tTA fusion construct containing the low efficiency cleavage site and assays were carried out using 10 µM U-69593, an agonist for OPRK. The maximal response to U-69593 resulted in an approximately 200-fold increase in reporter gene activity.

HTLA 2C11.6 cells were transfected with ADRA1A-GRPR 42aa Tail-tTA fusion construct containing the low efficiency cleavage site and assays were carried out using 10 µM epinephrine, an agonist for ADRA1A. The maximal response to epinephrine resulted in an approximately 14-fold increase in reporter gene activity.

HTLA 2C11.6 cells were transfected with DRD2-GRPR 42aa Tail-tTA fusion construct containing the low efficiency cleavage site and assays were carried out using 10 µM dopamine, an agonist for DRD2. The maximal response to dopamine resulted in an approximately 30-fold increase in reporter gene activity.

Example 27

This set of experiments were carried out to demonstrate further enhancements of the assay using a different set of test receptor modifications designed to increase the affinity for the interacting protein. In these examples, the C-terminal domain of the test receptor was replaced with a portion of the endogenous C-terminal tail domain of GRPR.

First, PCR was used to produce a DNA fragment encoding the truncated GRPR tail, specifically a sequence encoding 23 amino acids from Gly-343 to Asn-365. The fragment was designed such that the first amino acid of the C-terminal tail is preceded by two amino acids (Ser, S and Arg, R) which are encoded by the XbaI restriction site TCTAGA, and the Ser-366 is replaced by two amino acids (Gly, G and Ser, S) which are encoded by a BamHI restriction site GGATCC. This was accomplished by amplifying a plasmid containing the GRPR coding region with primers

```
tctagaggcctgatcatccggtctcac    (SEQ ID NO: 94)
and cggatccgttggtactcttgagg        (SEQ ID NO: 95)
```

Next the truncated GRPR fragment (hereafter referred to as GRPR 23aa Tail) was cut with XbaI and BamHI and inserted into the OPRK-GRPR 42aa Tail-tTA fusion construct containing the low efficiency cleavage site described herein, digested with XbaI and BamHI.

Similarly, the GRPR 23aa Tail fragment was cut with XbaI and BamHI and inserted into the ADRA1A-GRPR 42aa Tail-tTA fusion construct containing the low efficiency cleavage site described herein, digested with XbaI and BamHI.

HTLA 2C11.6 cells were transfected with OPRK-GRPR 23aa Tail-tTA fusion construct containing the low efficiency cleavage site and assays were carried out using 10 µM U-69593, an agonist for OPRK. The maximal response to U-69593 resulted in an approximately 115-fold induction of reporter gene expression over the background.

HTLA 2C11.6 cells were transfected with ADRA1A-GRPR 23aa Tail-tTA fusion construct containing the low efficiency cleavage site and assays were carried out using 10 µM epinephrine, an agonist for ADRA1A. The maximal response to epinephrine resulted in an approximately 102-fold induction of reporter gene expression over the background.

Example 28

This experiment was designed to demonstrate the use of the assay to measure the activity of the receptor tyrosine kinase Insulin-like Growth Factor-1 Receptor (IGF1R), specifically by monitoring the ligand-induced recruitment of the intracellular signaling protein SHC1 (Src homology 2 domain-containing transforming protein 1).

A first fusion construct was created, comprising DNA encoding the human IGF-1R, which can be found at GenBank under the Accession Number NM_000875 (SEQ ID NO: 96), fused in frame to a DNA sequence encoding amino acids 3-335 of the tetracycline-controlled transactivator tTA, described supra. Inserted between these sequences is a DNA sequence encoding the amino acid sequence GSENLYFQL (SEQ ID NO: 82) which includes the low efficiency cleavage site for TEV NIa-Pro, ENLYFQL (SEQ ID NO: 14), described supra. The CMV promoter was placed upstream of the IGF1R coding region, and a polyA sequence was placed downstream of the tTA region. This construct is designated IGF1R-TEV-NIa-Pro cleavage (Leu)-tTA.

A second fusion construct was created, comprising DNA encoding the PTB domain of human SHC1, corresponding to amino acids 1-238 (GeneBank accession number BC014158) (SEQ ID NO: 97) fused in frame to a DNA sequence encoding the catalytic domain of mature TEV NIa protease, described supra, corresponding to amino acids 2040-2279 (GeneBank accession number AAA47910) (SEQ ID NO: 79). Inserted between these sequences is a linker DNA sequence encoding the amino acids NSGS (SEQ ID NO: 98). The CMV promoter was placed upstream of the SHC1 PTB domain coding sequence and a polyA sequence was placed downstream of the TEV NIa protease sequence. This construct is designated SHC1-TEV.

The IGF1R-TEV-NIa-Pro cleavage (Leu)-tTA and SHC1-TEV fusion constructs were transfected into clone HTL5B8.1 cells described supra. About $2.5 \times 10^4$ cells were plated into each well of a 96 well-plate, in DMEM medium supplemented with 10% fetal bovine serum, 2 mM L-Glutamine, 100 units/ml penicillin, 500 µg/ml G418, and 3 µg/ml puromycin. Cells were grown to reach 50% confluency the next day and were transfected with 15 µl per well of a mixture consisting of 100 µl of DMEM, 0.2 µg of IGF1R-TEV-NIa-Pro cleavage (Leu)-tTA DNA, 0.2 µg of SHC1-TEV DNA, and 2 µl Fugene (a proprietary transfection reagent containing lipids and other material), which had been incubated for 15 minutes at room temperature prior to addition to the cells. Transfected cells were cultured for about 16 hours before treatment with a specific receptor agonist. After 24 hours, cells were lysed and luciferase activity was assayed as described supra.

The addition of 1 µM human Insulin-like Growth Factor 1 resulted in a 90 fold increase of luciferase reporter gene activity.

Example 29

This experiment was designed to demonstrate the use of the assay to measure the interaction of two test proteins that are not normally membrane bound. In this example, the assay was used to measure the ligand-induced dimerization of the nuclear steroid hormone receptors, ESR1 (estrogen receptor 1 or ER alpha) and ESR2 (estrogen receptor 2 or ER beta). In this example, ESR1 is fused to the transcription factor tTA, where the cleavage site for the TEV NIa-Pro protease is inserted between the ESR1 and tTA sequences. This ESR1-tTA fusion is tethered to the membrane by a fusion to the intracellular, C-terminal end of the transmembrane protein CD8. CD8 essentially serves as an inert scaffold that tethers ESR1 to the cytoplasmic side of the cell membrane. The transcription factor fused thereto cannot enter the nucleus until interaction with ESR2 and protease. Any transmembrane protein could be used. This CD8-ESR1-TEV NIa Pro cleavage-tTA fusion protein is expressed together with a second fusion protein comprised of ESR2 and the TEV NIa-Pro protease in a cell line containing a tTA-dependent reporter gene. The estrogen-induced dimerization of ESR1 and ESR2 thereby triggers the release of the tTA transcription factor from the membrane bound fusion, which is detected by the subsequent induction in reporter gene activity.

A fusion construct was created, comprising DNA encoding human CD8 gene (235 amino acids), which can be found in Genbank under Accession Number NM_001768 (SEQ ID NO: 99), fused in frame to a DNA sequence encoding the human ESR1 (596 amino acids), which can be found in Genbank under Accession Number NM_000125 (SEQ ID NO: 100). Inserted between these sequences is a DNA sequence encoding the amino acid sequence GRA (Gly-Arg-Ala). The resulting construct is then fused in frame to a DNA sequence encoding amino acids 3-335 of the tetracycline controlled transactivator tTA, described supra. Inserted between these sequences is a DNA sequence encoding the amino acid sequence GSENLYFQL (SEQ ID NO: 82) which includes the low efficiency cleavage site for TEV NIa-Pro, ENLYFQL (SEQ ID NO: 14), described supra. The CMV promoter was placed upstream of the Human CD8 coding region, and a poly A sequence was placed downstream of the tTA region. This construct is designated CD8-ESR1-TEV-NIa-Pro cleavage (L)-tTA.

A second fusion construct was created, using DNA encoding Human Estrogen Receptor beta (ESR2) (530 amino acids), which can be found at Genbank, under Accession Number NM_001437 (SEQ ID NO: 101), fused in frame to a DNA sequence encoding the catalytic domain of the TEV NIa protease, described supra corresponding to amino acids 2040-2279 (GenBank accession number AAA47910) (SEQ ID NO: 84). Inserted between these sequences is a DNA sequence encoding the amino acid sequence RS (Arg-Ser). The CMV promoter region was placed upstream of the Human Estrogen Receptor beta (ESR2) coding region, and a poly A sequence was placed downstream of the TEV region. This construct is designated ESR2-TEV.

The CD8-ESR1-TEV-NIa-Pro cleavage (L)-tTA and ESR2-TEV fusion constructs, together with pcDNA3 were transiently transfected into HTL5B8.1 cells described supra. About $2.0 \times 10^4$ cells were seeded in each well of a 96 well plate and cultured in phenol-free DMEM medium supplemented with 10% fetal bovine serum, 2 mM L-glutamine, 100 units/ml penicillin, 100 µg/ml G418, and 5 µg/ml puromycin. After 24 hours of incubation, cells were transfected with a mixture of 5 ng of ESR1-TEV-NIa-Pro cleavage (L)-tTA, 15 ng of ESR2-TEV and 40 ng of pCDNA3, together with 0.3 µl Fugene per well. 6 hours after transfection, the cells were washed with PBS and incubated in 100 µl of phenol-free DMEM without serum for 24 hours before treatment with 50 nM 17-β Estradiol. Ligand-treated cells were cultured for an additional 18-20 hours before they were assayed for luciferase reporter gene activity as described supra. Treatment with 50 nM 17-β Estradiol resulted in a 16-fold increase in reporter gene activity.

Other features of the invention will be clear to the skilled artisan and need not be reiterated here.

We claim:

1. A recombinant cell, said recombinant cell comprising a reporter gene and:
   (a) a first nucleic acid molecule which encodes a first fusion protein, said first nucleic acid molecule comprising:
      (i) a nucleotide sequence which encodes a first test protein, wherein said test protein is a transmembrane receptor,
      (ii) a nucleotide sequence which encodes a proteolytic cleavage site for a protease or a portion of a protease not expressed endogenously in said cell, and
      (iii) a nucleotide sequence which encodes a protein capable of activating said reporter gene in said cell, and
   (b) a second nucleic acid molecule which encodes a second fusion protein, said second nucleic acid molecule comprising:
      (i) a nucleotide sequence which encodes a second test protein whose interaction with said first test protein in the presence of a test compound is to be measured, and
      (ii) a nucleotide sequence which encodes said protease or said portion of a protease capable of specific proteolytic cleavage of said cleavage site.

2. The recombinant cell of claim 1, wherein one or both of said nucleic acid molecules are stably incorporated into the genome of said cell.

3. The recombinant cell of claim 1, wherein said cell has been transformed or transfected with said reporter gene.

4. The recombinant cell of claim 1, wherein said transmembrane receptor is a GPCR.

5. The recombinant cell of claim 1, wherein said protease or portion of a protease is tobacco etch virus nuclear inclusion A protease.

6. The recombinant cell of claim 1, wherein said protein capable of activating said reporter gene is a transcription factor.

7. The recombinant cell of claim 1, wherein said first test protein is ADBR2, AVPR2, HTR1A, CHRM2, CCR5, DRD2, or OPRK.

8. The recombinant cell of claim 6, wherein said transcription factor is tTA or GAL4.

9. The recombinant cell of claim 1, wherein said second test protein is an inhibitory protein.

10. The recombinant cell of claim 9, wherein said inhibitory protein is an arrestin.

11. The recombinant cell of claim 1, wherein said cell is a eukaryote.

12. The recombinant cell of claim 1, wherein said cell is a prokaryote.

13. The recombinant cell of claim 1, wherein said reporter gene is an exogenous gene.

14. The recombinant cell of claim 1, wherein the nucleotide sequence encoding said first test protein is modified to increase interaction with said second test protein.

15. The recombinant cell of claim 14, wherein said modification comprises replacing all or part of the nucleotide sequence of the C-terminal region of said first test protein with a nucleotide sequence which encodes an amino acid sequence which has higher affinity for said second test protein than the original sequence.

16. The recombinant cell of claim 15, wherein the nucleotide sequence of said C-terminal region is replaced by a nucleotide sequence encoding the C-terminal region of AVPR2, AGTRLI, GRPR, F2PL1, CXCR2/IL-8B, or CCR4.

17. The recombinant cell of claim 13, wherein said exogenous gene encodes an enzyme.

18. The recombinant cell of claim 17, wherein said enzyme is β-galactosidase, luciferase, chloramphenicol acetyl transferase, beta-glucouronidase, or alkaline phosphatase.

19. The recombinant cell of claim 13, wherein said exogenous gene encodes a protein which provides a detectable signal when expressed and is a fluorescent or chemiluminescent protein.

20. The recombinant cell of claim 19, wherein said fluorescent protein is green fluorescent protein, red fluorescent protein, or cyan fluorescent protein.

21. The recombinant cell of claim 1, wherein the presence of said test compound enhances association of said first and second test proteins.

22. The recombinant cell of claim 1, wherein said test compound is a ligand of the first test protein.

23. The recombinant cell of claim 1, wherein said test compound is an agonist of said first test protein.

\* \* \* \* \*